(12) United States Patent
Liu

(10) Patent No.: US 12,378,521 B2
(45) Date of Patent: Aug. 5, 2025

(54) METHOD FOR ENHANCING PRODUCTION OF GENETICALLY ENGINEERED AUTOLOGOUS T CELLS

(71) Applicant: AMGEN INC., Thousand Oaks, CA (US)

(72) Inventor: Yijun Liu, Camarillo, CA (US)

(73) Assignee: AMGEN INC., Thousand Oaks, CA (US)

( * ) Notice: Subject to any disclaimer, the term of this patent is extended or adjusted under 35 U.S.C. 154(b) by 975 days.

(21) Appl. No.: 17/228,843

(22) Filed: Apr. 13, 2021

(65) Prior Publication Data

US 2021/0324333 A1    Oct. 21, 2021

Related U.S. Application Data

(63) Continuation-in-part of application No. 16/849,023, filed on Apr. 15, 2020.

(51) Int. Cl.
| | |
|---|---|
| *C12N 5/0783* | (2010.01) |
| *A61K 39/00* | (2006.01) |
| *A61K 40/11* | (2025.01) |
| *A61K 40/31* | (2025.01) |
| *A61K 40/32* | (2025.01) |
| *A61K 40/42* | (2025.01) |
| *C07K 14/725* | (2006.01) |
| *C12N 15/86* | (2006.01) |

(52) U.S. Cl.
CPC ............ *C12N 5/0636* (2013.01); *A61K 40/11* (2025.01); *A61K 40/31* (2025.01); *A61K 40/32* (2025.01); *A61K 40/42* (2025.01); *C07K 14/7051* (2013.01); *C12N 15/86* (2013.01); *C12N 2501/2302* (2013.01); *C12N 2501/515* (2013.01); *C12N 2510/00* (2013.01); *C12N 2527/00* (2013.01); *C12N 2740/15043* (2013.01)

(58) Field of Classification Search
CPC ............ C12N 2527/00; C12N 5/0636; C12N 2501/2302; C12N 2510/00; A61K 40/11
See application file for complete search history.

(56) References Cited

U.S. PATENT DOCUMENTS

| | | | |
|---|---|---|---|
| 5,792,655 | A | 8/1998 | Watanabe et al. |
| 6,692,964 | B1 | 2/2004 | June et al. |
| 6,887,466 | B2 | 5/2005 | June et al. |
| 6,905,680 | B2 | 6/2005 | June et al. |
| 7,381,405 | B2 | 6/2008 | Liu et al. |
| 7,977,095 | B2 | 7/2011 | Bonyhadi et al. |
| 10,131,876 | B2 | 11/2018 | Kaiser et al. |
| 10,577,585 | B2 | 3/2020 | Nguyen et al. |
| 10,584,354 | B2 | 3/2020 | Wilson |
| 2001/0031253 | A1 | 10/2001 | Gruenberg |
| 2002/0115214 | A1 | 8/2002 | June et al. |
| 2002/0182730 | A1 | 12/2002 | Gruenberg |
| 2006/0121005 | A1 | 6/2006 | Berenson et al. |
| 2008/0274091 | A1 | 11/2008 | Slepushkin et al. |
| 2009/0226404 | A1 | 9/2009 | Schuler et al. |
| 2013/0287748 | A1 | 10/2013 | June et al. |
| 2014/0271635 | A1 | 9/2014 | Brogdon et al. |
| 2016/0068811 | A1 | 3/2016 | Kokaji |
| 2017/0037368 | A1 | 2/2017 | Germeroth et al. |
| 2017/0051252 | A1 | 2/2017 | Morgan et al. |
| 2017/0137783 | A1 | 5/2017 | Bedoya et al. |
| 2017/0296584 | A1 | 10/2017 | Bank et al. |
| 2018/0305665 | A1 | 10/2018 | Cho et al. |
| 2018/0320133 | A1 | 11/2018 | Forman et al. |
| 2019/0125799 | A1 | 5/2019 | Konto et al. |
| 2019/0169572 | A1 | 6/2019 | Shi et al. |
| 2019/0367876 | A1 | 12/2019 | Frost et al. |
| 2021/0393691 | A1 | 12/2021 | Cooper et al. |

FOREIGN PATENT DOCUMENTS

| | | | | |
|---|---|---|---|---|
| WO | 2014/153270 | A1 | 9/2014 | |
| WO | 2015/120096 | A2 | 8/2015 | |
| WO | 2016/014565 | A2 | 1/2016 | |
| WO | 2016/189159 | A1 | 12/2016 | |
| WO | WO-2017015490 | A1 * | 1/2017 | ............ A61K 35/17 |
| WO | 2018/005712 | A1 | 1/2018 | |
| WO | 2018/129540 | A1 | 7/2018 | |
| WO | 2019/055853 | A1 | 3/2019 | |
| WO | 2019/084234 | A1 | 5/2019 | |
| WO | 2019/084288 | A1 | 5/2019 | |
| WO | 2019/157298 | A1 | 8/2019 | |
| WO | 2020/047527 | A2 | 3/2020 | |
| WO | WO-2021211104 | A1 * | 10/2021 | ............ A61K 35/14 |

OTHER PUBLICATIONS

Apel, et al, Integrated Clinical Scale Manufacturing System for Cellular Products Derived by Magnetic Cell Separation, Centrifugation and Cell Culture, Chemie Ingenieur Technik 2013, 85, No. 1-2, pp. 103-110.
Barry et al., Lentiviral and Murine Retroviral Transduction of T Cells for Expression of Human CD40 Ligand, Human Gene Therapy, 2000, 11, pp. 323-332.
Brentjens, er al, CD19-Targeted T Cells Rapidly Induce Molecular Remissions in Adults with Chemotherapy-Refractory Acute Lymphoblastic Leukemia, Science Translational Medicine 2013, 5 (177) pp. 1-11.
Dodo, et al, An Efficient Large-Scale Retroviral Transduction Method Involving Preloading the Vector into a Retro Nectin-Coated Bag with Low-Temperature Shaking, PLOS One 2014, 9 (1) pp. 1-12.
Dwarshuis, et al, Cells as advanced therapeutics: State-of-the-art, challenges, and opportunities in large scale biomanufacturing of high-quality cells for adoptive immunotherapies, Advanced Drug Delivery Reviews, 2017, 114, pp. 222-239.
Feucht, et al, Efficient Separation of Human T Lymphocytes From Venous Blood Using Pvp-Coated Colloidal Silica Particles (Percoll), Journal of Immunological Methods, 1980, 38 pp. 43-51.
Grievink, et al, Comparison of Three Isolation Techniques for Human Peripheral Blood Mononuclear Cells: Cell Recovery and Viability, Population Composition, and Cell Functionality, Biopreservation and Biobanking, 2016, 14 (5) pp. 410-418.

(Continued)

*Primary Examiner* — Peter J Reddig

(57) ABSTRACT

The present invention relates to a method for enhancing production of autologous genetically engineered T cells for use in cell therapy applications.

37 Claims, 54 Drawing Sheets

(56) References Cited

OTHER PUBLICATIONS

Hanenberg, et al, Colocalization of retrovirus and target cells on specific fibronectin fragments increases genetic transduction of mammalian cells, Nature Medicine, 1996, 2(8), pp. 876-882.

Hollyman et al, Manufacturing validation of biologically functional T cells targeted to CD19 antigen for autologous adoptive cell therapy, J Immunother. 2009; 32(2): pp. 169-180.

June, et al, Generating and Expanding Autologous Chimeric Antigen Receptor T Cells from Patients with Acute Myeloid Leukemia, Methods in Molecular Biology, 2017, 1633, pp. 267-276.

Jung et al. Induction of cytotoxicity in resting human T lymphocytes bound to tumor cells by antibody heteroconjugates, PNAS USA, 1987, 84: pp. 4611-4615.

Lyer, et al, Industrializing Autologous Adoptive Immunotherapies: Manufacturing Advances and Challenges, Frontiers in Medicine 2018, 5 (150) pp. 1-9.

Lock, et al, Automated Manufacturing of Potent CD20-Directed Chimeric Antigen Receptor T Cells for Clinical Use, Human Gene Therapy, 2017, 28 (10) pp. 914-927.

Lu, et al, A Rapid Cell Expansion Process for Production of Engineered Autologous CAR-T Cell Therapies, Human Gene Therapy Methods, 2016, 27 (6) pp. 209-218.

Sabatino et al., Generation of clinical-grade CD19-specific CAR-modified CD81 memory stem cells for the treatment of human B-cell malignancies, Blood, 2016, 128 (4): pp. 519-528.

Sadeghi, et al, Large-scale bioreactor expansion of tumor-infiltrating lymphocytes, Journal of Immunological Methods, 2011, 364 pp. 94-100.

Somerville, et al, Clinical scale rapid expansion of lymphocytes for adoptive cell transfer therapy in the WAVER® bioreactor, Journal of Translational Medicine 2012, 10:69, pp. 1-11.

Somerville, et al, Bioreactors get personal, OncoImmunology, 2012, 1:8, pp. 1435-1437.

Tang, et al, Third-generation CD28/4-1BB chimeric antigen receptor T cells for chemotherapy relapsed or refractory acute lymphoblastic leukaemia:a non-randomised, open-label phase I trial protocol, BMJ Open, 2016, 6, pp. 1-7.

Arakawa et al., J. Biochem 1996, 120: pp. 657-662, 1996.

\* cited by examiner

B cells ered autologous T cells for use in cell therapy appli-

METHOD FOR ENHANCING PRODUCTION OF GENETICALLY ENGINEERED AUTOLOGOUS T CELLS

This application is a continuation-in-part and claims the benefit of U.S. application Ser. No. 16/849,023, filed Apr. 15, 2020, which is hereby incorporated by reference.

FIELD OF DISCLOSURE

The present invention relates to production of autologous genetically engineered T cells for use in cell therapy applications.

BACKGROUND

Adoptive T-cell therapy makes use of genetically engineered T cells and has been shown to be an effective and powerful therapeutic treatment in certain hematological indications. Autologous T cells are genetically engineered to express one or more cell surface receptors, such as chimeric antigen receptors (CARs) or T-cell receptors (TCRs), that recognize proteins of interest associated with the surface of target cells, while retaining and/or enhancing their ability to recognize and kill the target cells. In addition to the genetically engineered T cells' ability to recognize and destroy the targeted cells, successful adoptive T-cell therapy benefits from the T cells' ability to persist in the patient and continue to proliferate in response to a target antigen. Genetically engineered autologous T cells have shown great success in treating a wide range of cancers.

For autologous T cell therapeutics, the product is a live cell from a specific patient that will be returned to that patient. As such, autologous cell production is more challenging than conventional biopharmaceutical processes because one lot is manufactured for one patient. Manufacturing can only start when a patient sample is received and care must be taken that the cells are returned to the patient without significant modifications that make the cells a risk rather than an efficacious treatment. Production is more hands on and labor intensive, and performed multiple times at a small scale, to produce cells at sufficient quantity and quality. Donor to donor variability increases the complexity, because the starting material is different for each new lot produced.

The specifications for assessing an autologous drug product are also different from a typical recombinant protein drug product. For autologous T-cell therapeutics, product purity, cell phenotype, percent engineered T cells, potency and specificity, are the parameters tested. Integrated closed process platforms using complex automated systems are being developed but carry a high capital investment. Developing an efficient, scalable, reliable, and cost-effective process remains one of the main challenges for the advancement of use of autologous cells as a therapeutic, which is for the most part a highly manual process.

There is a need for production processes for generating T-cell therapeutics, particularly autologous T-cell therapeutics, that reduce risk of contamination, cost, facility footprint, and the inefficiencies and complexity of current manufacturing processes. Autologous T-cell therapies are forecast to be in the range of $350,000 to $475,000 per patient, not including hospital-associated costs. If genetically engineered autologous T cells are to achieve their full clinical and commercial potential, the challenges facing production of clinical grade cells at commercially relevant quantities and quality must be overcome. The invention described herein meets this need by providing an efficient and effective method manufacture to genetically engineered T cells for autologous cell therapy.

BRIEF SUMMARY OF THE INVENTION

The invention provides a method for producing genetically engineered autologous T cells that have reduced background activation and target irrelevant toxicity, the method comprising a) adding culture media comprising about 300 IU per ml IL-2 to a closed single use bioreactor bag; b) inoculating the bioreactor bag with apheresed donor cells and one or more soluble T cell activators, wherein at least one soluble T-cell activator is bound to at least one donor cell at the time of inoculation and the bioreactor bag is part of a rocking bioreactor platform; c) culturing the cells in the closed single use bioreactor bag containing culture media comprising about 300 IU per ml IL-2 and continuously rocking the bag at a rate of 2 rpm at a 2° angle; d) transducing the cells in the bioreactor bag with at least one soluble viral vector comprising a polynucleotide which encodes a protein of interest, the bioreactor bag containing culture media comprising about 300 IU per ml IL-2 and continuously rocking the bioreactor bag at a rate of 2 rpm at a 2° angle; and e) expanding the cells in the bioreactor bag, feeding the culture with culture media comprising about 300 IU per ml IL-2 until Day 5 or Day 6 of the culture, after which the culture is fed with culture media comprising no IL-2, increasing the culture volume and the rocking rate as needed to maintain the culture until harvest, wherein the harvested cells have reduced background activation and target irrelevant toxicity compared to engineered autologous T cells expressing the same protein of interest from the same apheresed donor cells produced by the same method in which IL-2 is maintained in the culture media at a concentration of about 300 IU per ml until harvest. In one embodiment, the apheresed donor cells comprise cells from peripheral blood. In a related embodiment, the apheresed donor cells comprise nucleated and non-nucleated cells. In one embodiment the apheresed donor cells comprise leukocytes and erythrocytes. In a related embodiment the apheresed donor cells also comprise granulocytes and/or platelets. In one embodiment the apheresis is leukapheresis. In another embodiment the apheresed donor cells are washed and resuspended in a culture media. In another embodiment at least one T cell activator is an anti CD3 antibody or binding fragments thereof. In yet another embodiment the T cell activator comprises an anti CD3 antibody and an anti CD28 antibody, or binding fragments thereof. In another embodiment the T cell activator comprises at least an anti CD3 antibody, an anti CD28 antibody, and an anti CD2 antibody, or binding fragments thereof. In another embodiment the T cell activator comprises at least an anti-human CD3 monospecific tetrameric antibody complex, an anti-human CD28 monospecific tetrameric antibody complex, and an anti-human CD2 monospecific tetrameric antibody complex. In yet another embodiment the concentration of at least one soluble T cell activator is at least 0.001 μg/ml to at least 10 μg/ml. In a related embodiment the concentration of at least one soluble T cell activator is at least 0.1 μg/ml to at least 5 μg/ml. In one embodiment the number of nucleated cells within the apheresed donor cells is about 1.0E9 to about 1.4E9. In a related embodiment the number of nucleated cells within the apheresed donor cells is about 1.2E9 to about 1.4E9. In one embodiment the bioreactor bag contains at least 300 ml of culture media at inoculation. In another embodiment the apheresed donor cells are cultured in the bioreactor bag for about 12-24 hours. In another embodiment the viral vector is a retroviral vector. In another embodiment the viral vector is a lentiviral vector. In a related embodiment the lentiviral vector is added at a MOI of 0.25-10. In a related embodiment the lentiviral vector is added at a MOI of 1. In one embodiment the cells are transduced for about 20-24 hours. In one embodiment following transduction half of the culture media is removed from the bioreactor bag and replaced with an equal volume of fresh culture media. In a related embodiment the culture is incubated for about 12-24 hours. In one embodiment during expansion the culture is fed by fed batch and/or perfusion. In a related embodiment during expansion the culture is perfused at a rate is one half to double the bioreactor bag volume per day. In one embodiment during expansion the volume of the culture media in bioreactor is incrementally increased to 500 ml to maintain a cell density of at least 4E6 nucleated cells/ml. In one embodiment at harvest the volume of culture media in the single use closed bioreactor bag is 500 ml rocking at a rate of 4 rpm at a 4° angle to 6 rpm at a 6° angle. In one embodiment the expansion begins at a culture volume of about 300 ml of culture media at a rocking rate of about 2 rpm at a 2° angle until the cells reach a predetermined cell density, the cell expansion is continued at a second culture volume of about 400 ml of culture media at a rocking rate of about 5 rpm at a 5° angle until the cells reach a predetermined cell density, and the cell expansion is continued at a third culture volume of about 500 ml at a rocking rate of about 6 rpm at a 6° angle until the cells reach a predetermined cell density after which the culture is maintained until harvest. In one embodiment the predetermined cell density is 4E6 cells/ml. In one embodiment the cells are expanded for until they reach a target harvest cell density. In a related embodiment the target harvest cell density is about 10 billion cells. In one embodiment the culture, transduction, and/or expansion steps are performed at 34-37° C. In one embodiment the protein of interest is a cell surface receptor. In a related embodiment the cell surface receptor a T cell receptor, or chimeric antigen receptor. In a related embodiment the cell surface receptor recognizes an antigenic target associated with a target cell. In a related embodiment the target cell is a cancer cell. In one embodiment the genetically engineered autologous T cells are used to treat an indication in a patient in need. In one embodiment is provided a pharmaceutical composition comprising the genetically engineered autologous T cells from the method described above. In a related embodiment is provided a method of treating an indication in a patient in need, comprising administering to the patient the pharmaceutical composition described above.

The invention provides a method for producing genetically engineered autologous T cells expressing at least one protein of interest, the method comprising a) inoculating a closed single use bioreactor bag containing culture media with apheresed donor cells and one or more soluble T cell activators, wherein at least one soluble T-cell activator is bound to at least one donor cell at the time of inoculation and the bioreactor bag is part of a rocking bioreactor platform; b) culturing the cells in the closed single use bioreactor bag continuously rocking at a rate of about 2 rpm at a 2° angle; c) transducing the cells in the closed single use bioreactor bag with at least one soluble viral vector comprising a polynucleotide which encodes the protein of interest continuously rocking at a rate of about 2 rpm at a 2° angle; d) expanding the cells in the closed single use bioreactor bag at a first culture volume of about 300 ml of culture media at a first rocking rate of about 2 rpm at a 2° angle until the cells reach a predetermined cell density, then culturing the cells at a second culture volume of about 400 ml at a second rocking rate of about 5 rpm at a 5° angle until the cells reach a predetermined cell density, then culturing the cells at a third culture volume of about 500 ml at a third rocking rate of about 6 rpm at a 6° angle until the cells reach a predetermined cell density; and maintaining the culture until harvest. In one embodiment the closed single use bioreactor bag is inoculated with apheresed donor cells comprising 1.2E6 nucleated cells per ml.

The invention provides a method for enhancing transduction efficiency of genetically engineered autologous T cells expressing a protein of interest, the method comprising a) inoculating a closed single use bioreactor bag containing culture media with apheresed donor cells comprising 1.4E9 nucleated cells and one or more soluble T cell activators, wherein at least one soluble T-cell activator is bound to at least one donor cell at the time of inoculation and the bioreactor bag is part of a rocking bioreactor platform; b) culturing the apheresed donor cells in the closed single use bioreactor bag containing 200 ml culture media continuously rocking at a rate of about 2 rpm at a 2° angle; c) transducing the cells in the closed single use bioreactor bag with at least one soluble viral vector comprising a polynucleotide which encodes the protein of interest continuously rocking at a rate of about 2 rpm at a 2° angle; and d) expanding the cells in the closed single use bioreactor bag at a rocking rate of about 2 rpm at a 2° angle and increasing the culture volume and rocking the rate as needed to maintain the culture until harvest. In one embodiment is provided when the cell culture is expanded to a predetermined cell density, the cell expansion is continued at a second culture volume of about 300 ml of culture media at a second rocking rate of about 3 rpm at a 3° angle until the cells reach a predetermined cell density, then at a third culture volume of about 400 ml at the second rocking rate of about 3 rpm at a 3° angle until the cells reach a predetermined cell density, then at the third culture volume of about 400 ml at a third rocking rate of about 4 rpm at a 4° angle to about 6 rpm at a 6° angle until the cells reach a predetermined cell density after which the culture is maintained until harvest. In a related embodiment the predetermined cell density is about 4E6 cells/ml.

DETAILED DESCRIPTION OF THE INVENTION

Figure 1A:
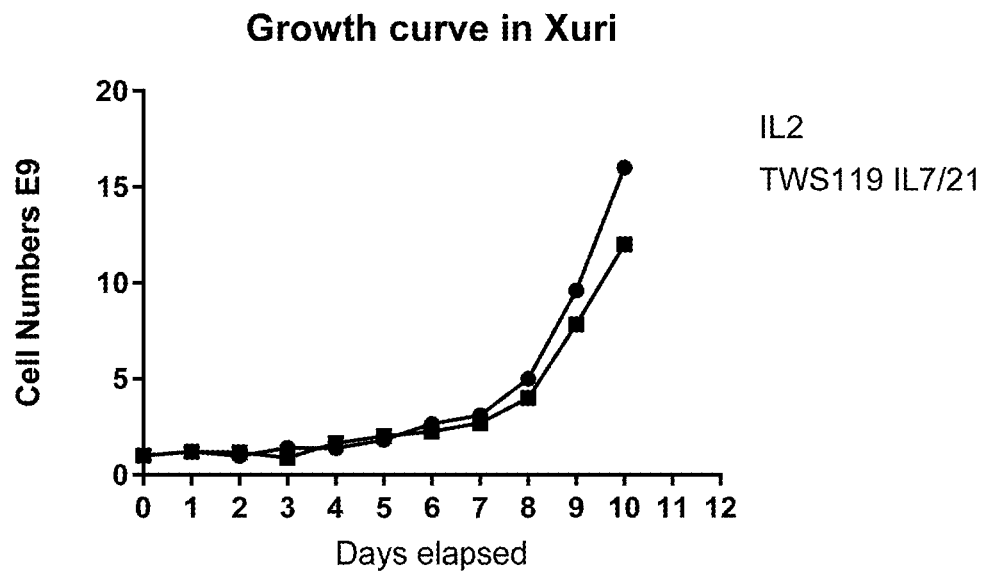
FIG. 1. (A) Growth curve of cell expansion in XURI® W25 bioreactor supplemented with IL-2 only or cocktail of IL7, IL-21, and TWS119. (B) Viability of cell expanded in XURI® W25 bioreactor supplemented with IL-2 only or IL7, IL-21, and TWS119 cocktail.

Autologous T-cell therapy is a personalized therapy, the genetically engineered T cells being derived from the patient's own cells, "autologous cells", which are manipulated and returned to the patient. T cell or T lymphocyte refers to a type of lymphocyte (others are B cells and NK cells) that actively participates in the body's immune response. While use of autologous cells reduces the risk of immunological responses, manufacturing a therapy at one lot per patient adds complexity and cost. Also, because autologous T-cell therapy is patient-centric, this treatment is unlike traditional biologic therapeutics, and is not suitable for large scale production and off-the-shelf use.

Autologous T-cell therapy involves treating patients with their own live T cells that have been engineered to express a protein of interest that recognizes a protein associated with a target cell. Autologous T cell manufacturing processes typically make use of multiple unit operations including semi-closed and/or closed steps, moving the patient's cells between multiple vessels such as plates, flasks, containers, bags, or other types of vessels, typically gas permeable vessels, over the course of production. These transfers may involve movement of fluid from one vessel to another by means such as syringes or pipettes, centrifuges, and the like that can put unnecessary stress on the cells through shear forces and expose the cells to contaminants and loss. In addition, such vessels require manual transfer into and between equipment, such as cell separators, biosafety cabinets, and incubators.

As described herein, a method for producing genetically engineered autologous T cells that express a protein of interest has been developed that produces T cells of high purity, greater than 98%, with high transgene expression, greater than 45% on CD8 T cells, generates cell yields of greater than 10 billion with a viability of greater than 90% in a 10-day completely closed and continuous process. Starting with an apheresed donor sample, the T cells are selectively expanded from about 50% when harvested to greater than 98% following genetic manipulation and expansion of the activated cells. The resulting T cells are less differentiated and remain in a more stem-cell or memory-like phenotype which increases persistence and over all efficacy. The resulting cells are more potent in killing target cells and resistant target cell challenge. In addition, withdrawal of IL-2 from the feed media during the expansion phase potently reduced activation marker CD25 expression and target irrelevant killing of T2 cells while not affecting T cell growth, viability, immunophenotypes, TCR surface expression, and specific target cell killing function.

While the growth rate and viability were equivalent to cells that were enriched prior to activation and transduction, the transduction was more efficient, and the function and efficacy of the cells produced directly from harvested donor cells were greater.

The genetically engineered autologous T cells were generated in a closed continuous rocking culture through the steps of activation, transduction, and expansion, using bioreactor capable of producing a rocking motion throughout. The rocking was tailored to the variances in bioreactor volume, (increasing to 1 liter by the end of expansion), and oxygen levels as the cell density increased during the process. This ensured a sufficient mass transfer of oxygen and nutrients to support the high-density cultures in contrast to methods using static culture which must be grown at low cell density (≤2E6 cells/ml) due to limitations of the culture media under static conditions. While the cells that were rocked in a bioreactor bag and a commonly used static G-Rex® gas permeable culture system both had efficient oxygen transport, the G-Rex® system lacked the convection flow that transfers nutrients to cells in a timely manner. Also, the bioreactor bags can take advantage of perfusion of fresh media which supports very high cell densities, up to 50E6 cells/ml in some cases.

Compared to cells generated in static, gas permeable vessels or cultures generated using a combination of static (activation and transduction operations) and rocking (expansion operations) systems, the method described herein eliminated more than 30% of the hands-on work and greatly reduced the cost. Incubators and other support equipment that is essential for preparing and maintaining static cultures in gas permeable vessels are not necessary, reducing the manufacturing footprint and risk of contamination of the cells and the equipment from the necessary handling and manipulation that these static cultures require. While the growth rate and viability of the cells generated by these systems were equivalent, the transgene expression, function and efficacy of the cells generated by the method described herein was greater than for the cells generated in cultures making use of gas permeable vessels in static or hybrid static/rocking cultures.

The combination of agitation and bioreactor volume promoted increased cell growth rate and led to a shorter expansion time and resulted in more desired T cell phenotypes. Enhanced agitation and reduced bioreactor volume showed higher level of T memory cells and lower levels of T enhancer cells compared to the control. A stepwise increase in culture volume from 0.3 L to 0.4 L to 0.5 L, and a stepwise increase in agitation and angle from 2 rpm at an angle of 2° to 5 rpm at an angle of 5° to 6 rpm at an angle of 6° over the course of a culture was found to achieve an improved growth rate, memory T cell phenotype, and transduction efficiency.

The donor may be any subject from which a sample of blood cells is needed for producing genetically engineered autologous T cells. The donor may be a patient in need of treatment with a population of cells generated by the method described herein (i.e., an autologous donor).

The donor cells may be harvested from the circulating peripheral blood by any suitable method used in the art such as extracorporeal methods, venipuncture, or other blood collection methods by which a sample of blood is typically obtained. In one embodiment, the donor cells are harvested by apheresis. Apheresis refers to the withdrawal of blood from a donor, which is separated into cellular and soluble components, removing certain desired components from the blood and then returning the remainder of the blood to the donor. Where T cells are a desired cell type, such as for cell therapy applications, leukapheresis, an apheresis process which preferentially removes white blood cells (leukocytes) from the peripheral blood of a donor, is most often used. The harvested leukapheresis sample may be provided in a Leukopak® container. Multiple blood volumes are processed from the same donor to generate a full Leukopak®.

Apheresis separates the incoming blood into the various blood components using methods such as differential centrifugation. However, because there is a close range in the density between blood components, this will not result in pure cell populations, there will be residual cells in any sample collected by an apheresis process, and the quantities of these residual cells will increase as the volume of blood processed during the apheresis procedure increases. Cells harvested by leukapheresis will comprise nucleated cells, such as leukocytes, including monocytes, dendritic cells, lymphocytes (T-, B-, and NK cells), and granulocytes, as well as megakaryocytes, and cells without a nucleus, such as erythrocytes and platelets. While the percentage of lymphocytes in the collected apheresed sample is more concentrated compared to whole blood, there will also be a significant number of other cells such as NK cells, red blood cells, platelets, and granulocytes in the sample as well.

Apheresed cells are frequently used as source for collecting blood-based cells, such as leukocytes and lymphocytes. However, since these samples include a mixture of blood cells, for example, LEUKOPACK®s containing apheresed cells can contain tens of billions of red blood cells making the collected cell sample visibly red. Red blood cells are known to have an impact further processing of the cells in the sample, such as by drastically lower transfection rates when using electroporation, for example "As there is inherent variability in the cell populations in these leukapheresis products, processes to remove unwanted cells or isolate specific populations of cells have been developed using a variety of technologies including physical separation via centrifugation, magnetic, fluorescent, as well as acoustic-based selection. Cells types can be separated based on size through centrifugation, with or without the use of density gradient media systems (such as Ficoll, for example), which enables removal of unwanted fractions of leukapheresis product such as granulocytes, platelets and remaining red blood cell contaminants." Iyer et al., (2018) Frontiers in Medicine, Vol. 5, 150. It is common practice in production of autologous and allogenic T cells to further isolate, select, and/or enrich for desired cell populations or phenotypes from the apheresed sample before using the cells in a particular method or application related to cell therapy. The purpose of this further processing is to obtain a more highly defined population of cells, such as PBMCs, or specific lymphocyte populations, for uses such as T cell activation or expansion, see for example, Stroncek et al. Journal of Translational Medicine 2014, 12:241-249.

Procedures for obtaining desired cell populations, such as enrichment of certain T cell phenotypes, are one of the most expensive unit operations in an autologous T cell manufacturing process, averaging around $10K per patient in a clinical setting using the CliniMACs Plus magnetic separation technique, for example. Even after enrichment, T cell purity only reaches 90-95% and some 10% of T cells may be lost in the negative fraction (flow-through).

The standard procedure for separation of red blood cells and granulocytes from the PBMCs and lymphocytes in a harvested blood sample, such as apheresed cells, is by use of density gradient centrifugation. The typical density gradient material used for this purpose is Ficoll®, a hydrophilic polysaccharide, that separates the components in blood samples, such as whole blood or blood collected via an apheresis process or other method. A Ficoll® density gradient separates mononuclear cells, dendritic cells and lymphocytes (T, B and NK cells) which are found in the buffy coat and separated from the red blood cells, platelets, and granulocytes which are found in the pellet. However, different Ficoll® separation media, protocols, operator skill, and the like, can affect the yield, viability, and function of the cells. In addition, in some processes the cells are manipulated in a hyperosmolar Ficoll® solution followed by resuspension in artificial media, which may have profound modifying effects on T cell function, see Mallone et al., Clinical and Experimental Immunology, 163: 33-49 (2010). Also, lymphocytes expressing high-avidity binding for autologous erythrocytes have been shown to lead to a loss of these T-rosetting cells during Ficoll® separation, see for example, Hokland et al. Scand. J. Immunol, 11, 353-356 (1980).

In addition, apheresed cells that are further isolated, selected and/or enhanced are subjected to additional manipulations, such as centrifugation as part of wash and separation processes, density gradients, and the like. This can lead to cell damage and loss due to the repeated shear forces experienced during these processes. In addition, each time the cells are handled, whether manually or as part of an automated process, there is an increased risk of exposure and contamination of the cells. For a manufacturing facility where a high volume of samples from different donors are processed for use in autologous cell therapy applications, contamination of a processed sample with foreign donor cells is a serious risk and danger to the donor patient.

The method described herein makes use of the entire apheresed sample without further isolation, separation, and/or enrichment for specific cell populations or phenotypes. The method starts with billions of cells harvested by leukapheresis which comprise nucleated cells, such as leukocytes, including monocytes, dendritic cells, lymphocytes (T-, B-, and NK cells), and granulocytes, as well as megakaryocytes, and cells without a nucleus, such as erythrocytes and platelets. While only about 30-60% of the cells in the apheresed sample are T cells, the other supporting cells have a positive effect on the outcome of the method, contributing to the overall health of the T cells from Day 0. The genetically engineered T cells derived from these apheresed samples grew faster, had higher transduction efficiencies, and maintained a more memory-like state when they are processed along with other cells in the apheresed sample, compared to the same apheresed cells that were further enriched for specific T cell populations.

It was found that further isolation, selection and/or enrichment for any subset of the apheresed cells, such as by cell type or phenotype, was not necessary to achieve genetically engineered T cells with a high degree of purity and viability, with high transgene expression, and starting with this mixed cell population, did not impact the capability of generating cell densities well over 10 billion in a 10-day process. The resulting T cells were less differentiated and remained in a more memory-like phenotype which increases persistence and over all efficacy, as well as being more potent in killing target cells upon challenge. Starting with the apheresed cells eliminates additional separation steps such as magnetic separation or other sedimentation to isolate cells of interest, resulting in a continuous minimal manipulation operation from apheresed donor cells to harvest of genetically engineered T cells. This drastically reduces the per patient footprint inside a manufacturing facility and the time for processing the harvested cells. In addition, eliminating the need for selection or enhancement of donor cells prior to activation, results in less manipulation of the donor sample, decreases exposure to unnecessary chemicals such as Ficoll®, reduces overall cell loss, overall cost, and the possibility of damage to cells, and greatly diminished the risk of contaminating the patient sample. Autologous cell samples come from patients with grievous diseases. There is always a risk when taking a cell sample from these patients and administering the resulting genetically engineered T cells back to the patient. Exposing the patient to additional unnecessary risks by excessive manipulation and exposure of the cells to unnecessary processing, mishandling during the intensive hands on processing, or administering contaminated cells back to the patient, is not a viable option.

The invention provides a method for producing genetically engineered autologous T cells expressing at least one protein of interest, the method comprising inoculating a closed single use bioreactor bag containing culture media with apheresed donor cells and one or more soluble T cell activators, wherein the bioreactor bag is part of a rocking bioreactor platform, culturing the cells in the closed single use bioreactor bag continuously rocking at a rate of about 2 rpm, transducing the cells in the closed single use bioreactor bag with at least one soluble viral vector comprising a polynucleotide which encodes the protein of interest continuously rocking at a rate of about 2 rpm, and expanding the cells in the closed single use bioreactor bag at a rocking rate of about 2 rpm and increasing the culture volume and rocking the rate as needed to maintain the culture until harvest.

In one embodiment the apheresed donor cells comprise cells from peripheral blood. In a related embodiment the apheresed donor cells comprise nucleated and non-nucleated cells. In one embodiment the apheresed donor cells comprise leukocytes and erythrocytes. In a related embodiment the apheresed donor cells also comprise granulocytes and/or platelets. In one embodiment the apheresis is leukapheresis. In a related embodiment the apheresed donor cells are provided in a Leukopak®.

The apheresed donor cells are not subjected to any further isolation, selection and/or enrichment for any cell population(s) or cell type(s) following apheresis, and prior to activating the apheresed donor cells.

As will be appreciated, the harvested cells may be washed to remove the plasma fraction and any apheresis buffers, and to place the harvested cells in an appropriate buffer or media for subsequent processing. Closed, automated processes are commercially available for this purpose and include Sepax C-Pro (GE Healthcare, Pittsburgh, PA), Cobe 2991 cell processor (Terumo BCT, Lakewood, CO), CellSaver 5 (Haemonetics, (Boston, MA)) and the like. In one embodiment the apheresed donor cells are washed and resuspended in a culture media prior to inoculation. No additional wash steps are performed until the expanded genetically engineered autologous T cells are harvested for formulation and cryopreservation.

T cell activation is an antigen-dependent process resulting in proliferation and differentiation of naïve T cells into effector cells. Activation is stimulated by primary and coactivating signals. With appropriate stimulation T cells will proliferate in vitro. T cells require two signals to become fully activated, the primary stimulation is antigen specific, from interaction of the T cell receptor with a peptide-HLA molecule on an antigen presenting cell. The second is non-antigen specific co-stimulatory signals from interaction between the membrane of the antigen presenting cell and the T cell.

As described herein, activation strength did not appear to correlate with better transduction efficiency. Bound activators did not yield high transduction rates despite providing the highest signal strength. Soluble activators, such as the mixtures of soluble CD3, CD28, and/or CD2 antibodies, particularly the combination of soluble CD3, CD28 and CD2 antibodies, had a signal strength falling between activators bound to bags and those bound to beads, however they activated T cells with the highest expression of GFP and the engineered TCR.

One or more soluble T cell activators may be used to produce a population of activated T cells. Such T cell activators include antibodies or functional fragment thereof that target T cell stimulator and/or co-stimulatory molecules. Such T cell activators include, but are not limited to, anti-CD3 antibodies or binding fragments, anti-CD28 antibodies or binding fragments, and anti-CD2 antibodies or binding fragments, or combinations thereof. Also included are anti-human CD3 monospecific tetrameric antibody complex, an anti-human CD28 monospecific tetrameric antibody complex, and an anti-human CD2 monospecific tetrameric antibody complex. Such T cell activators are commercially available from a variety of sources including Stem Cell Technologies, Vancouver, BC CA, among others.

In one embodiment at least one T cell activator is an anti CD3 antibody or binding fragments thereof. In one embodiment the T cell activator comprises an anti CD3 antibody and an anti CD28 antibody, or binding fragments thereof. In another embodiment the T cell activator comprises at least an anti CD3 antibody, an anti CD28 antibody, and an anti CD2 antibody, or binding fragments thereof. In another embodiment the T cell activator comprises at least an anti-human CD3 monospecific tetrameric antibody complex, an anti-human CD28 monospecific tetrameric antibody complex, and an anti-human CD2 monospecific tetrameric antibody complex.

In one embodiment the concentration of at least one soluble T cell activator is at least 0.001 µg/ml to at least 10 µg/ml. In a related embodiment the concentration is at least 0.01 µg/ml to at least 10 µg/ml. In a related embodiment the concentration is at least 0.1 µg/ml to at least 10 µg/ml. In a related embodiment the concentration is at least 1 µg/ml to at least 10 µg/ml. In a related embodiment the concentration is at least 5 µg/ml to at least 10 µg/ml. In one embodiment the concentration of at least one T cell activator is at least 0.001 µg/ml to at least 1 µg/ml. In a related embodiment the concentration of at least one T cell activator is at least 0.01 µg/ml to at least 1 µg/ml. In a related embodiment the concentration of at least one T cell activator is at least 0.1 µg/ml to at least 1 µg/ml. In one embodiment the concentration of at least one T cell activator is at least 0.001 µg/ml to at least 5 µg/ml. In a related embodiment the concentration of at least one T cell activator is at least 0.01 µg/ml to at least 5 µg/ml. In a related embodiment the concentration of at least one T cell activator is at least 0.1 µg/ml to at least 5 µg/ml. In a related embodiment the concentration of at least on T cell activator is at least 1 µg/ml to at least 5 µg/ml. In one embodiment the concentration is at least 0.001 µg/ml. In one embodiment the concentration is at least 0.01 µg/ml. In one embodiment the concentration is at least 0.1 µg/ml. In one embodiment the concentration is at least 1 µg/ml. In one embodiment the concentration is at least 5 µg/ml. In one embodiment the concentration is at least 10 µg/ml. In one embodiment the concentration greater than 10 µg/ml.

In one embodiment the wherein the culture media comprises at least one soluble cytokine. Cytokines, such as IL-1, IL-2, IL-4, IL-5, IL-7, IL-15, and/or IL-21, may also be used as soluble T cell stimulating agents.

In one embodiment the soluble cytokine selected from IL-2, IL-7, IL-15, or IL-21. In one embodiment the soluble cytokine is IL-7 in combination with IL-15 or IL-21. Such cytokines may be used at concentrations from at least 5 ng/ml to at least 30 ng/ml or more. In one embodiment, the concentration of at least one cytokine is at least 5 ng/ml to at least 25 ng/ml. In one embodiment the concentration of at least one cytokine is at least 5 ng/ml to at least 20 ng·ml. In one embodiment the concentration of at least one cytokine is at least 5 ng/ml to at least 15 ng/ml. In one embodiment the concentration of at least one cytokine is at least 5 ng/ml to at least 10 ng/ml. In one embodiment the concentration of at least one cytokine is at least 10 ng/ml to at least 20 ng/ml. In one embodiment the concentration of at least one cytokine is at least 5 ng/ml. In one embodiment the concentration of at least one cytokine is at least 10 ng/ml. In one embodiment the concentration of at least one cytokine is at least 15 ng/ml. In one embodiment the concentration of at least one cytokine is at least 20 ng/ml. In one embodiment the concentration of at least one cytokine is at least 25 ng/ml. In one embodiment the concentration of at least one cytokine is at least 30 ng/ml. In one embodiment the concentration of at least one cytokine is greater than 30 ng/ml. Other molecules that impact T cell activation or maturation may also be included, such as a WNT pathway activator. Such activators include 4,6-disubstituted pyrrolopyrimidine TWS119, an inhibitor of the serine/threonine kinase glycogen-synthase-kinase-3β (Gsk-3β), (Stemcell Technologies). In one embodiment the concentration of TWS119 is at least 5 µM to at least 20 µM or more. In one embodiment the concentration of TWS119 is at least 5 µM to at least 15 µM. In one embodiment the concentration of TWS119 is at least 5 µM to at least 10 µM. In one embodiment the concentration of TWS119 is at least 10 µM to at least 20 µM. In one embodiment the concentration of TWS119 is at least 5 µM. In one embodiment the concentration of TWS119 is at least 10 µM. In one embodiment the concentration of TWS119 is at least 15 µM. In one embodiment the concentration of TWS119 is at least 20 µM. In one embodiment the concentration of TWS119 is greater than 20 µM. In one embodiment the culture media comprises a mixture of soluble TWS117, IL-7, and IL-21.

In one embodiment at least one soluble cytokine is IL-2. In one embodiment the IL-2 is at a concentration of about 250 IU/ml to about 350 IU/ml. In one embodiment the soluble cytokine is IL-2 at a concentration of about 250 IU/ml to 300 IU/ml. In one embodiment the soluble cytokine is IL-2 at a concentration of about 300 IU/ml to 350 IU/ml. In one embodiment the soluble cytokine is IL-2 at a concentration of about 250 IU/ml, 300 IU/ml, or 350 IU/ml. In one embodiment the soluble cytokine is IL-2 at a concentration of about 250 IU/ml. In one embodiment the soluble cytokine is IL-2 at a concentration of about 300 IU/ml. In one embodiment the soluble cytokine is IL-2 at a concentration of about 350 IU/ml.

The invention provides a method for producing genetically engineered autologous T cells that have reduced background activation and target irrelevant toxicity, the method comprising adding culture media comprising about 300 IU per ml IL-2 to a closed single use bioreactor bag; inoculating the bioreactor bag with apheresed donor cells and one or more soluble T cell activators, wherein at least one soluble T-cell activator is bound to at least one donor cell at the time of inoculation and the bioreactor bag is part of a rocking bioreactor platform; culturing the cells in the bioreactor bag containing culture media comprising about 300 IU per ml IL-2 and continuously rocking the bioreactor bag at a rate of 2 RPM at an angle of 2°; transducing the cells in the bioreactor bag with at least one soluble viral vector comprising a polynucleotide which encodes a protein of interest, the bioreactor bag containing culture media comprising about 300 IU per ml IL-2 and continuously rocking the bag at a rate of 2 RPM at an angle of 2°, and expanding the cells in the bioreactor bag, feeding the culture with culture media comprising about 300 IU per ml IL-2 until Day 5 or Day 6 of the culture, after which the culture is fed with culture media comprising no IL-2, increasing the culture volume and the rocking rate as needed to maintain the culture until harvest, wherein the harvested cells have reduced background activation and target irrelevant toxicity compared to engineered autologous T cells expressing the same protein of interest from the same apheresed donor cells produced by the same method in which IL-2 is maintained in the culture media at a concentration of about 300 IU per ml until harvest.

"Reduced background activation" or "minimal activation signaling" are used interchangeably and refer to changes in the activation state of T cells elicited from cell expansion stimulation as determined by CD25 surface expression. In the case of IL-2 withdrawal from the perfusion media of T cell cultures, there was a reduction in the expression of activation marker CD25 to a minimal level (<10%) compared to a control that continued to receive IL-2 until the cells were harvested.

"Target irrelevant toxicity", as opposed to target specific toxicity, refers to unspecific cell lysis resulting from cell expansion stimulation mediated activation and is calculated based on the percentage of cell death of T2 cells co-cultured with T cells for 24 hours normalized to T2 cell cultured alone. This measures the percentage of unspecific killing (target irrelevant killing) of T cells compared to a control.

During antigen stimulation, T cells shift to a glycolytic metabolism to sustain effector function. This happens in the first few days after adding activators to the cells. Glycolysis inhibitors can be added with the activators to inhibit glycolysis metabolism during the activation and transduction steps, which can contribute to generation of T cells with less differentiated phenotypes, enhanced transduction efficiency, and/or enhanced T cell expression. As described herein, the engineered T cells derived from 2-deoxy-D-glucose (2-DG)-inhibited T cells produced more Tscm and Tcm compared with the T cells derived from the media without 2-DG. The inhibitor can be kept in the culture media until harvest or removed at any point to restore glycolysis and support T cell expansion. In one embodiment the culture media also comprises a soluble glycolysis inhibitor. In a related embodiment the soluble glycolysis inhibitor is 2-deoxy-D-glucose (2-DG). In one embodiment the concentration of 2-DG is about 1 mM to about 3 mM. In a related embodiment the concentration of 2-DG is about 1 mM to about 2 mM. In a related embodiment the concentration of 2-DG is about 2 mM to about 3 mM. In one embodiment the concentration of 2-DG is about 1 mM or less. In one embodiment the concentration is about 2 mM. In one embodiment the concentration of 2-DG is about 3 mM or more.

Procedures for producing engineered T cells comprise many unit operations such as cell isolation, selection and/or enrichment of the harvested donor sample for a particular cell type or phenotype, activation, transduction, expansion, harvest, formulation, and cryopreservation. During each of these steps, multiple vessels or processes may be used to perform each operation. For example, to obtain a desired cell type or phenotype, one or more closed vessels and/or processes may be used to perform steps such as washes, magnetic-antibody labeling, performing selection or enrichments procedures, centrifugation/sedimentation, and concentration of the isolated, selected, or enriched cells. Much use is made of bound activators for activation and/or bound agents to enhance transduction, whether they are coated on plates, or bags, or bound to beads or other supports. Once the stimulation or transduction using these bound activators is complete, the cells must be removed, washed, and transferred to new vessels. Multiple vessels may be used during expansion to accommodate increased demand for nutrients and increasing culture volume. Switches between different types of vessels associated with these steps is time-consuming and costly and may expose the cells to damage, loss and contamination.

As described herein, the invention provides a closed continuous operation from inoculation of apheresed donor cells all the way through to the harvest of expanded genetically engineered T cells. All steps, including activation, transduction, and expansion, take place in a single closed bioreactor system that is constantly rocked at a speed of at least 2 rpm. This not only minimizes manual manipulation of donor material, reducing risk of contamination and cell loss, it allows for automated feeding and culture manipulation. Additional equipment, such as incubators and separate vessels for activation and/or transduction, are not necessary to process the donor's cells which drastically reduces the risk of contamination and cells loss, they also reduced the cost in materials/reagents and FTE time, and the per patient footprint inside a manufacturing facility.

As described herein, activation, transduction, and expansion in a continuously rocking bioreactor that makes use of soluble components in a culture media optimized for T cell growth, resulted in a high-density production of engineered autologous T cells from washed apheresed donor cells. Use of soluble components such as T cell activators, stimulators, and metabolic pathway inhibitors, allowed for a continuous flow between the various steps in the manufacture of the autologous engineered T cells and produced engineered T cells at a desired phenotype and transgene expression. Rocking during this process also ensured a sufficient mass transfer of oxygen and nutrients to support high-density cultures in contrast to static cultures which must be grown at low cell density (≤2E6 cells/ml) due to limitation of the culture media under static conditions. While the rocking bioreactors and commonly used G-Rex® gas permeable culture systems both have efficient oxygen transport, the G-Rex® systems lacks the convection flow that transfers nutrients to cells in a timely manner. Also, using the rocking bioreactor system allows for perfusion of fresh media which enable very high cell densities, up to 50E6 cells/ml in some cases.

Activation, transduction, and expansion of autologous donor apheresed cells comprising leukocytes and erythrocytes, was carried out in a continuous closed system within a single bioreactor bag that was rocked continuously. Bioreactor bags, such as Cellbag™ bioreactor bags (GE Healthcare) are used as part of rocking bioreactor platforms such as Wave Bioreactor™ or XURI® Cell Expansion systems (GE Healthcare), and in addition to operating as a bioreactor also have the capability of rocking at various speeds and angles which allows efficient mass transfer of oxygen and nutrients without introducing too much shear stress to T cells. Such bioreactor bags are typically equipped with perfusion filters to filter incoming culture media, ports and lines for adding culture media and other components, withdrawing spent media and samples, all within a sterile controlled environment. The bags are also equipped to connect with controls on the rocking platform system that automatically measure and control culture parameters such as temperature, $CO_2$, $O_2$, pH and metabolic and media parameters such as glucose and lactate, as well as controlling gas and media flow. The bags allow for automated feeding, be it bolus, fed batch, fed batch/perfusion, and/or semi- or continuous perfusion. In addition to reducing the amount of manual manipulation of cells, culturing the cells in a closed bioreactor system allows for greater capacity and improvement to the yield and culture density of the engineered T cells.

Production of engineered autologous T cells for cell therapy indications typically relies on static cultures that make use of gas permeable vessels which can require extensive manual manipulation, exposing the cultures and the equipment to contamination risk as well as limiting nutrient flow to cells. Static, gas permeable vessels, such as bags, flasks, and plates, are widely used in autologous T cell processes that involve a transduction step to produce genetically engineered T cells. Examples of such static gas permeable cell culture bags currently used include Permalife Cell Culture Bags, Origin Biomedical, Austin Texas, MACS GMP Cell Differentiation Bags, Miltenyi Biotech, Cambridge, MA), Rapid Expansion Flask (G-Rex) bioreactor, other G-Rex® vessels Wilson-Wolf Manufacturing. These vessels require an incubator or other climate-controlled chamber to maintain desired temperatures and are gas permeable to allow passive diffusion of $O_2$ from the ambient incubator environment and $CO_2$ from the media. The vessels require manual manipulation to move them to and from processing equipment, incubators, or biosafety cabinets, and the like that are necessary for maintaining the cultures. In addition, the vessels require constant connecting and reconnecting to processing equipment, syringes, pumps, chambers, and other vessels and devices to maintain the cultures. The manual processing increases the risk of contamination to the cultures. In addition, Permalife Cell Culture bags are only designed for low density T cell expansion (<2E6 cells/ml) and will require extremely large volumes to supply at the high-dosages required for T cell therapy. G-Rex®, on the other hand, could expand T cells in a relatively high density (~10E6 cells/ml) but are challenged with any manipulation of expansion parameters. These two vessels are also not equipped with control systems and data recording ability to support a more advanced and digital manufacturing operation.

The inventive method provides inoculating a closed single use bioreactor bag containing culture media with apheresed donor cells and one or more soluble T cell activators, wherein the bioreactor bag is part of a rocking bioreactor platform. The volume of culture media in the bioreactor bag at the time of inoculation can be any predetermined volume. In one embodiment the volume of culture media is at least the minimal volume of the bioreactor bag. In one embodiment the second volume of culture media is at least 300 ml. In one embodiment the volume of the culture media 400 ml or more. In one embodiment the volume of culture media is about 300 ml to about 400 ml. In one embodiment the volume of the culture media is about 325 ml to about 400 ml. In one embodiment the volume of the culture media is about 350 ml to about 400 ml. In one embodiment the volume of the culture media is about 375 ml to about 400 ml. In one embodiment the volume of culture media is about 300 ml, about 325 ml, about 350 ml, about 375 ml, or about 400 ml. In one embodiment the volume of culture media is about 300 ml. In one embodiment the volume of culture media is about 325 ml. In one embodiment the volume of culture media is about 350 ml. In one embodiment the volume of culture media about 375 ml. In one embodiment the volume of culture media is about 400 ml. In one embodiment the volume of culture media is about 400 ml or more.

T cells require cell-cell contact to activate and survive. An insufficient concentration of cells during activation could reduce cell-cell contact to a level associated with poor activation. The apheresed donor cells comprise nucleated and non-nucleated cells. The number of nucleated cells in the apheresed donor sample can be determined by any known method, including the use of automated systems such as a NC-200™ Automated Cell Counter (ChemMetec, Denmark). In one embodiment the apheresed donor cells comprise a sufficient number of nucleated cells for activation in the bioreactor bag at a rocking speed of 2 rpm. In one embodiment the apheresed donor cells comprise about 1.0E9 to 1.3E9 nucleated cells. In a related embodiment the apheresed donor cells comprise about 1.1E9 to about 1.2E9 nucleated cells. In a related embodiment the apheresed donor cells comprise about 1.2E9 to about 1.3E9 nucleated cells. In a related embodiment the apheresed donor cells comprise about 1.2E9 to about 1.25E9 nucleated cells. In a related embodiment the apheresed donor cells comprise about 1.0E9 nucleated cells. In a related embodiment the apheresed donor cells comprise about 1.1E9 nucleated cells. In a related embodiment the apheresed donor cells comprise about 1.2E9 nucleated cells. In a related embodiment the apheresed donor cells comprise about 1.25E9 nucleated cells. In a related embodiment the apheresed donor cells comprise about 1.3E9 nucleated cells. In a related embodiment the apheresed donor cells comprise about 1.0E6 nucleated cells, about 1.1E9 nucleated cells, about 1.2E9 nucleated cells, about 1.25E9 nucleated cells, or about 1.3E9 nucleated cells. In one embodiment the apheresed donor cells comprise about 1.3E9 to 1.4E9 nucleated cells. In one embodiment the apheresed donor cells comprise about 1.4E9 nucleated cells.

The invention provides a method for enhancing transduction efficiency of genetically engineered autologous T cells expressing a protein of interest, the method comprising inoculating a closed single use bioreactor bag containing culture media with apheresed donor cells comprising 1.4E9 nucleated cells and one or more soluble T cell activators, wherein at least one soluble T-cell activator is bound to at least one donor cell at the time of inoculation and the bioreactor bag is part of a rocking bioreactor platform, culturing the apheresed donor cells in the closed single use bioreactor bag containing 200 ml culture media continuously rocking at a rate of about 2 rpm at an angle of 2°, transducing the cells in the closed single use bioreactor bag with at least one soluble viral vector comprising a polynucleotide which encodes the protein of interest continuously rocking at a rate of about 2 rpm at an angle of 2°, and expanding the cells in the closed single use bioreactor bag at a rocking rate of about 2 rpm at an angle of 2° and increasing the culture volume and rocking the rate as needed to maintain the culture until harvest. In one embodiment the cell expansion is continued in the closed single use bioreactor bag at a second culture volume of about 300 ml of culture media at a second rocking rate of about 3 rpm at an angle of 3° until the cells reach a predetermined cell density, then at a third culture volume of about 400 ml at the second rocking rate of about 3 rpm at an angle of 3° until the cells reach a predetermined cell density, then at the third culture volume of about 400 ml at a third rocking rate of about 4 rpm at an angle of 4°, 5 rpm at an angle of 5°, or 6 rpm at an angle of 6° until the cells reach a predetermined cell density.

In one embodiment the invention provides inoculating a closed single use bioreactor bag containing culture media with apheresed donor cells at a cell density of about 1E6 to about 5E6 nucleated cells/ml. In a related embodiment the cell density of about 2E6 to about 4E6 nucleated cells/ml. In one embodiment the cell density is about 3E6 to about 4E6 nucleated cells/ml. In one embodiment the cell density is about 3E6 to about 3.75E6 nucleated cells/ml. In one embodiment the cell density is about 3E6 to about 3.5E6 nucleated cells/ml. In one embodiment the cell density is about 3E6 to about 3.35E6 nucleated cells/ml. In one embodiment the cell density is about 2E6 to about 3E6 nucleated cells/ml. In one embodiment the cell density is about 2E6 nucleated cells/ml, about 3E6 nucleated cells/ml, about 3.25E6 nucleated cells/ml, about 3.5E6 nucleated cells/ml, about 3.75E6 nucleated cells/ml, or about 4E6 nucleated cells/ml. In one embodiment the cell density is about 2E6 nucleated cells/ml. In one embodiment the cell density is about 3E6 nucleated cells/ml. In one embodiment the cell density is about 3.25E6 nucleated cells/ml. In one embodiment the cell density is about 3.75E6 nucleated cells/ml. In one embodiment the cell density is about 3.5E6 to about 7E6 nucleated cells/ml. In one embodiment the cell density is about 7E6 nucleated cells/ml. In one embodiment the cell density is about 3.75E6 nucleated cells/ml. In one embodiment the cell density is about 4E6 nucleated cells/ml. In one embodiment the cell density is about 3E6 nucleated cells/ml to 4E6 nucleated cells/ml in about 300 ml culture media containing a soluble cytokine. In one embodiment the cell density is about 3E6 nucleated cells/ml to 7E6 nucleated cells/ml in about 200 to about 300 ml culture media containing a soluble cytokine. In one embodiment the cell density is about 7E6 nucleated cells/ml in about 200 ml culture media containing a soluble cytokine.

In one embodiment the invention provides inoculating a closed single use bioreactor bag containing culture media with apheresed donor cells at a cell density of about 4E6 to about 7E6 nucleated cells/ml.

The during activation cells can be cultured at a predetermined temperature. In one embodiment, the cells are cultured at 34-39° C. In one embodiment, the cells are cultured at 34-35° C. In one embodiment, the cells are cultured at 35-37° C. In one embodiment, the cells are cultured at 35-36° C. In one embodiment, the cells are cultured at 36-37° C. In one embodiment, the cells are cultured at 34° C., 35° C., 36° C., or 37° C. In one embodiment, the cells are cultured at 34° C. In one embodiment, the cells are cultured at 35° C. In one embodiment, the cells are cultured at 36° C. In one embodiment, the cells are cultured at performed at 37° C.

The during activation cells can be cultured for a predetermined time. In one embodiment, the cells are cultured for at least 12 hours. In one embodiment, the cells are cultured for at least 24 hours. In one embodiment the cells are cultured for at least 12 to at least 24 hours. In one embodiment the cells are cultured for at least 12 to at least 20 hours. In one embodiment the cells are cultured for at least 12 to at least 18 hours. In one embodiment the cells are cultured for at least 12 to at least 16 hours. In one embodiment the cells are cultured for at least 12 to at least 14 hours. In one embodiment the cells are cultured for at least 14 to at least 24 hours. In one embodiment the cells are cultured for at least 14 to at least 20 hours. On one embodiment the cells are cultured for at least 14 to at least 18 hours. On one embodiment the cells are cultured for at least 14 to at least 16 hours. On one embodiment the cells are cultured for at least 16 to at least 24 hours. On one embodiment the cells are cultured for at least 16 to at least 20 hours. In one embodiment the cells are cultured for at least 16 to at least 18 hours. On one embodiment the cells are cultured for at least 18 to at least 24 hours. In one embodiment the cells are cultured for at least 18 to 20 hours. In one embodiment the cells are cultured for at least 20 to at least 24 hours. In one embodiment the cells are cultured for at least 12 hours. In one embodiment the cells are cultured for at least 13 hours. In one embodiment the cells are cultured for at least 14 hours. In one embodiment the cells are cultured for at least 15 hours. In one embodiment the cells are cultured for at least 16 hours. In one embodiment the cells are cultured for at least 17 hours. In one embodiment the cells are cultured for at least 18 hours. In one embodiment the cells are cultured for at least 19 hours. In one embodiment the cells are cultured for at least 20 hours. In one embodiment the cells are cultured for at least 21 hours. In one embodiment the cells are cultured for at least 22 hours. In one embodiment the cells are cultured for at least 23 hours. In one embodiment the cells are cultured for at least 24 hours.

In one embodiment of the invention, at least one soluble T-cell activator is bound to at least one donor cell at the time of inoculation. In one embodiment the apheresed donor cells are incubated with one or more soluble T cell activators prior to inoculating into the bioreactor bag. In one embodiment the incubation is for a sufficient time to allow for saturation of binding of one or more soluble T cell activators to the apheresed donor cells prior to inoculation. In one embodiment the apheresed donor cells are incubated with one or more T cell activators for at least 30 minutes or more. In one embodiment the apheresed donor cells are incubated with one or more T cell activators for at least 30 minutes to at least 2 hours or more. In a related embodiment the apheresed donor cells are incubated with one or more T cell activators for at least 1 hour to at least 2 hours. In one embodiment the incubation is at least 30 minutes. In one embodiment the incubation is about 1 hour. In one embodiment the incubation is about 2 hours.

In one embodiment the apheresed donor cells and one or more soluble T cell activators are incubated in a transfer bag. A minimal amount of culture media, enough to suspend the cells and the soluble T cell activator and allow for binding of the activator to the nucleated cells, is used, preferably enough to keep the total volume of cells low and cell density at 100-150 E6 cells/ml. In one embodiment the volume of culture media in the transfer bag is about 5 ml to about 50 ml. In one embodiment of the invention, the initial volume of culture media comprising a soluble cytokine and one or more T cell activators is about 5 ml to about 40 ml. In one embodiment of the invention, the initial volume of culture media comprising a soluble cytokine and one or more T cell activators is about 5 ml to about 30 ml. In one embodiment of the invention, the initial volume of culture media comprising a soluble cytokine and one or more T cell activators is about 5 ml to about 20 ml. In one embodiment of the invention, the initial volume of culture media comprising a soluble cytokine and one or more T cell activators is about 5 ml to about 19 ml. In one embodiment of the invention, the initial volume of culture media comprising a soluble cytokine and one or more T cell activators is about 5 ml to about 18 ml. In one embodiment of the invention, the initial volume of culture media comprising a soluble cytokine and one or more T cell activators is about 5 ml to about 17 ml. In one embodiment of the invention, the initial volume of culture media comprising a soluble cytokine and one or more T cell activators is about 5 ml to about 16 ml. In one embodiment of the invention, the initial volume of culture media comprising a soluble cytokine and one or more T cell activators is about 5 ml to about 15 ml. In one embodiment of the invention, the initial volume of culture media comprising a soluble cytokine and one or more T cell activators is about 5 ml to about 14 ml. In one embodiment of the invention, the initial volume of culture media comprising a soluble cytokine and one or more T cell activators is about 5 ml to about 13 ml. In one embodiment of the invention, the initial volume of culture media comprising a soluble cytokine and one or more T cell activators is about 5 ml to about 12 ml. In one embodiment of the invention, the initial volume of culture media comprising a soluble cytokine and one or more T cell activators is about 5 ml to about 11 ml. In one embodiment of the invention, the initial volume of culture media comprising a soluble cytokine and one or more T cell activators is about 5 ml to about 10 ml. In one embodiment of the invention, the initial volume of culture media comprising a soluble cytokine and one or more T cell activators is about 5 ml to about 9 ml. In one embodiment of the invention, the initial volume of culture media comprising a soluble cytokine and one or more T cell activators is about 5 ml to about 8 ml. In one embodiment of the invention, the initial volume of culture media comprising a soluble cytokine and one or more T cell activators is about 5 ml to about 7 ml. In one embodiment of the invention, the initial volume of culture media comprising a soluble cytokine and one or more T cell activators is about 5 ml to about 6 ml. In one embodiment of the invention, the initial volume of culture media comprising a soluble cytokine and one or more T cell activators is about 16 ml to about 20 ml. In one embodiment of the invention, the initial volume of culture media comprising a soluble cytokine and one or more T cell activators is about 8 ml, about 6 ml, about 7 ml, about 8 ml, about 9 ml, about 10 ml, about 15 ml, about 20 ml, about 30 ml, about 40 ml, or about 50 ml.

Transduction refers to the process whereby foreign DNA is introduced into a cell via viral vector. See Jones et al., (1998). Genetics: principles and analysis. Boston: Jones & Bartlett Publ. As used herein, "vector" means any molecule or entity such as a viral a vector, that is useful for transformation of a host cell, such as a T cell, and contain nucleic acid sequences that direct and/or control (in conjunction with the cell) expression of one or more heterologous coding regions operatively linked thereto. An expression construct may include, but is not limited to, sequences that affect or control transcription, translation, and, if introns are present, affect RNA splicing of a coding region operably linked thereto. One or more vectors are then inserted into the cell for amplification and/or polypeptide expression. The transformation of an expression vector into a selected cell may be accomplished through viral transformation. Viral transformed T cells can be obtained by transducing cells with a viral vector comprising a polynucleotide which encodes the protein of interest. Viral vectors include retroviral vectors, murine leukemia virus vectors, SFG vectors, adenoviral vectors, lentiviral vectors, adeno-associated virus (AAV) vectors, Herpes virus vectors, and vaccinia virus vectors.

The invention provides transducing the cells in the closed single use bioreactor bag with at least one viral vector comprising a polynucleotide which encodes the protein of interest while continuously rocking at a rate of 2 rpm. The continuous rocking rate of 2 rpm allowed for sufficient cell-cell contact, necessary for successful transformation. In one embodiment the culture is rocked at a rate of 2 RPM at a 2° angle. In addition, inoculating the bioreactor bags at a high cell density (7E6 cells/ml) appears to play a positive role in affecting lentivirus vector transduction efficiency.

In one embodiment, the viral vector is a retroviral vector. Retroviral vectors, such as lentivirus vectors, persist in the nucleus as integrated provirus and reproduce with cell division. In one embodiment the viral vector is a lentiviral vector.

In one embodiment the cells can be engineered using one or more viral vectors comprising one or more polynucleotide sequences encoding one or more proteins of interest. In one embodiment the protein of interest is cell surface receptor. In one embodiment the cell surface receptor is a chimeric antigen receptor or a T cell receptor. In one embodiment the cell surface receptor recognizes an antigenic target on the surface of a target cell.

In one embodiment the lentiviral vector is added at a multiplicity of infection (MOI) of 0.25-10. In one embodiment the lentiviral vector is added at a MOI of 0.25-5. In one embodiment the lentiviral vector is added at a MOI of 0.25-2. In one embodiment the lentiviral vector is added at a MOI of 0.25-1. In one embodiment the lentiviral vector is added at a MOI of 0.25-0.5. In one embodiment the lentiviral vector is added at a MOI of 0.5-10. In one embodiment the lentiviral vector is added at a MOI of 0.5-5. In one embodiment the lentiviral vector is added at a MOI of 0.5-2. In one embodiment the lentiviral vector is added at a MOI of 0.5-1. In one embodiment the lentiviral vector is added at a MOI of 1-10. In one embodiment the lentiviral vector is added at a MOI of 1-5. In one embodiment the lentiviral vector is added at a MOI of 1-2. In one embodiment the lentiviral vector is added at a MOI of 2-10. In one embodiment the lentiviral vector is added at a MOI of 2-5. In one embodiment the lentiviral vector is added at a MOI of 5-10. In one embodiment the lentiviral vector is added at a MOI of 0.25, 0.5, 1, 2, 5, or 10. In one embodiment the lentiviral vector is added at a MOI of 10. In one embodiment the lentiviral vector is added at a MOI of 5. In one embodiment the lentiviral vector is added at a MOI of 2. In one embodiment the lentiviral vector is added at a MOI of 1. In one embodiment the lentiviral vector is added at a MOI of 0.5. In one embodiment the lentiviral vector is added at a MOI of 0.25.

The cells can be transduced at a predetermined temperature. In one embodiment, the cells are transduced at 34-39° C. In one embodiment, the cells are transduced at 34-35° C. In one embodiment, the cells are transduced at 35-37° C. In one embodiment, the cells are transduced at 35-36° C. In one embodiment, the cells are transduced at 36-37° C. In one embodiment, the cells are transduced at 34° C., 35° C., 36° C., or 37° C. In one embodiment, the cells are transduced at 34° C. In one embodiment, the cells are transduced at 35° C. In one embodiment, the cells are transduced at 36° C. In one embodiment, the cells are transduced at performed at 37° C.

The cells can be transduced for a predetermined time. In one embodiment, the cells are transduced for at least 12 hours. In one embodiment, the cells are transduced for at least 24 hours. In one embodiment the cells are transduced for at least 12 to at least 24 hours. In one embodiment the cells are transduced for at least 12 to at least 20 hours. In one embodiment the cells are transduced for at least 12 to at least 18 hours. In one embodiment the cells are transduced for at least 12 to at least 16 hours. In one embodiment the cells are transduced for at least 12 to at least 14 hours. In one embodiment the cells are transduced for at least 14 to at least 24 hours. In one embodiment the cells are transduced for at least 14 to at least 20 hours. On one embodiment the cells are transduced for at least 14 to at least 18 hours. On one embodiment the cells are transduced for at least 14 to at least 16 hours. On one embodiment the cells are transduced for at least 16 to at least 24 hours. On one embodiment the cells are transduced for at least 16 to at least 20 hours. In one embodiment the cells are transduced for at least 16 to at least 18 hours. On one embodiment the cells are transduced for at least 18 to at least 24 hours. In one embodiment the cells are transduced for at least 18 to 20 hours. In one embodiment the cells are transduced for at least 20 to at least 24 hours. In one embodiment the cells are transduced for at least 12 hours. In one embodiment the cells are transduced for at least 13 hours. In one embodiment the cells are transduced for at least 14 hours. In one embodiment the cells are transduced for at least 15 hours. In one embodiment the cells are transduced for at least 16 hours. In one embodiment the cells are transduced for at least 17 hours. In one embodiment the cells are transduced for at least 18 hours. In one embodiment the cells are transduced for at least 19 hours. In one embodiment the cells are transduced for at least 20 hours. In one embodiment the cells are transduced for at least 21 hours. In one embodiment the cells are transduced for at least 22 hours. In one embodiment the cells are transduced for at least 23 hours. In one embodiment the cells are transduced for at least 24 hours.

As described herein, transduction was performed using a rocking bioreactor equipped with a single use bioreactor bag at a rocking rate of 2 rpm, in particular, a rocking rate of 2 rpm at an angle of 2°. One or more viral vectors comprising polynucleotides encoding proteins of interest may be directly inoculated into the culture in the bioreactor bag while the bag is rocking. Use of bags impermeable to gas such as those as used on rocking bioreactors has not been recommended for use during transduction. "Vessels that are impermeable to gas, such as disposable bioreactors that are designed to fit rocking motion bioreactors, are not ideal for transduction of cells via viral vectors. Therefore, transduction is currently carried out in static cell culture bags or planar vessels.", see Farid and Jenkins, Bioprocesses for Cell Therapies, Chapter 44, Biopharmeceutical Processing: Development, Design and Implementation of Manufacturing Processes, Eds. Jagschies et al., Elsevier, page 914, 2018.

However, as described herein, compared to cells transduced in static gas permeable vessels, the cells transduced in disposable bioreactors bags designed to be part of rocking motion bioreactors had a greater transduction efficiency, were less differentiated, more memory-cell like, and had greater potency in killing target cells than those cells transduced in a static gas permeable bag or in a static G-Rex® gas permeable system.

In one embodiment, following transduction, half of the culture media is removed from the bioreactor bag and replaced with an equal volume of fresh culture media and rocked at a rate of 2 rpm. In one embodiment the culture is rocked at a rate of 2 RPM at a 2° angle.

The cells can be cultured at a predetermined temperature. In one embodiment, the cells are cultured at 34-39° C. In one embodiment, the cells are cultured at 34-35° C. In one embodiment, the cells are cultured at 35-37° C. In one embodiment, the cells are cultured at 35-36° C. In one embodiment, the cells are cultured at 36-37° C. In one embodiment, the cells are cultured at 34° C., 35° C., 36° C., or 37° C. In one embodiment, the cells are cultured at 34° C. In one embodiment, the cells are cultured at 35° C. In one embodiment, the cells are cultured at 36° C. In one embodiment, the cells are cultured at performed at 37° C.

The cells can be cultured for a predetermined time. In one embodiment, the cells are cultured for at least 12 hours. In one embodiment, the cells are cultured for at least 24 hours. In one embodiment the cells are cultured for at least 12 to at least 24 hours. In one embodiment the cells are cultured for at least 12 to at least 20 hours. In one embodiment the cells are cultured for at least 12 to at least 18 hours. In one embodiment the cells are cultured for at least 12 to at least 16 hours. In one embodiment the cells are cultured for at least 12 to at least 14 hours. In one embodiment the cells are cultured for at least 14 to at least 24 hours. In one embodiment the cells are cultured for at least 14 to at least 20 hours. On one embodiment the cells are cultured for at least 14 to at least 18 hours. On one embodiment the cells are cultured for at least 14 to at least 16 hours. On one embodiment the cells are cultured for at least 16 to at least 24 hours. On one embodiment the cells are cultured for at least 16 to at least 20 hours. In one embodiment the cells are cultured for at least 16 to at least 18 hours. On one embodiment the cells are cultured for at least 18 to at least 24 hours. In one embodiment the cells are cultured for at least 18 to 20 hours. In one embodiment the cells are cultured for at least 20 to at least 24 hours. In one embodiment the cells are cultured for at least 12 hours. In one embodiment the cells are cultured for at least 13 hours. In one embodiment the cells are cultured for at least 14 hours. In one embodiment the cells are cultured for at least 15 hours. In one embodiment the cells are cultured for at least 16 hours. In one embodiment the cells are cultured for at least 17 hours. In one embodiment the cells are cultured for at least 18 hours. In one embodiment the cells are cultured for at least 19 hours. In one embodiment the cells are cultured for at least 20 hours. In one embodiment the cells are cultured for at least 21 hours. In one embodiment the cells are cultured for at least 22 hours. In one embodiment the cells are cultured for at least 23 hours. In one embodiment the cells are cultured for at least 24 hours.

The invention provides expanding the cells in the closed single use bioreactor bag at a rocking rate of about 2 rpm and increasing the culture volume and rocking the rate as needed to maintain the culture until harvest. T cells require cell-cell contact to survive. Less than 2E6 cells/ml can deprive cell-cell contact, increase cell stress, and/or decrease ability to overcome bioreactor agitation and to proliferate. Scale-up to 4E6 cells/ml or more allows for timely increases in the culture volume, which also simplifies the feeding process. Stepwise increases in culture volume allow for scale up of the culture to 1 liter in a timely manner, with rocking speed/angle corresponding to increases in volume to allow for a steady amount of dissolve oxygen in the system to facilitate cell expansion. During activation, T cells consume and release large amounts of glucose and lactate. High levels of lactate appear to be detrimental for T cell activation and expansion. As a result, cell media exchange is not a parameter corresponding to cell density in the early phase of activation and transduction as the cells are not expanding much. During activation/transduction, lactate level is the critical culture parameter and sufficient turnover of media is a critical for T cell activation and expansion. Semi-continuous media exchange is used to control metabolite level in the culture media.

T cells can reach a higher density when cultured in a rocking bioreactor platform than in static gas permeable vessel system. Final yield for the process described herein, was between 15 million to 35 billion cells in a 1 L bioreactor in 10-14 days. One bioreactor is sufficient to support one patient. To achieve the same 10 billion engineered T cells as produced in a single liter produced by the inventive method would require ~20 permeable bags (250 ml) or a 4 L G®-rex bioreactor. The cell yield of the inventive method is higher than that of other common processes in field.

In one embodiment, as the cells expand the volume of the culture media is incrementally increased to maintain a cell density of at least 2E6 nucleated cells/ml. In one embodiment as the cells expand the volume of the culture media in bioreactor is incrementally increased to 1 liter during expansion to maintain a cell density of at least 4E6 nucleated cells/ml. In one embodiment the cell density during expansion is at least 2E6 cells/ml or higher. In one embodiment the cell density is about 2E6 cells/ml to about 3.75E6 cells/ml. In one embodiment the cell density is about 2E6 cells/ml to about 3.50E6 cells/ml. In one embodiment the cell density is about 2E6 cells/ml to about 3.25E6 cells/ml. In one embodiment the cell density is about 2E6 cells/ml to about 3.00E6 cells/ml. In one embodiment the cell density is about 2E6 cells/ml to about 2.75E6 cells/ml. In one embodiment the cell density is about 2E6 cells/ml to about 2.50E6 cells/ml. In one embodiment the cell density is about 2E6 cells/ml to about 2.25E6 cells/ml. In one embodiment the cell density is about 2.25E6 cells/ml to about 4.0E6 cells/ml. In one embodiment the cell density is about 2.25E6 cells/ml to about 3.75E6 cells/ml. In one embodiment the cell density is about 2.25E6 cells/ml to about 3.50E6 cells/ml. In one embodiment the cell density is about 2.25E6 cells/ml to about 3.25E6 cells/ml. In one embodiment the cell density is about 2.25E6 cells/ml to about 3.0E6 cells/ml. In one embodiment the cell density is about 2.25E6 cells/ml to about 2.75E6 cells/ml. In one embodiment the cell density is about 2.25E6 cells/ml to about 2.50E6 cells/ml. In one embodiment the cell density is about 2.50E6 cells/ml to about 4.0E6 cells/ml. In one embodiment the cell density is about 2.50E6 cells/ml to about 3.75E6 cells/ml. In one embodiment the cell density is about 2.50E6 cells/ml to about 3.50E6 cells/ml. In one embodiment the cell density is about 2.50E6 cells/ml to about 3.25E6 cells/ml. In one embodiment the cell density is about 2.50E6 cells/ml to about 3.00E6 cells/ml. In one embodiment the cell density is about 2.50E6 cells/ml to about 2.75E6 cells/ml. In one embodiment the cell density is about 2.50E6 cells/ml to about 2.50E6 cells/ml. In one embodiment the cell density is about 2.50E6 cells/ml to about 2.75E6 cells/ml. In one embodiment the cell density is about 2.75E6 cells/ml to about 4.0E6 cells/ml.

In one embodiment the cell density is about 2.75E6 cells/ml to about 3.75E6 cells/ml. In one embodiment the cell density is about 2.75E6 cells/ml to about 3.50E6 cells/ml. In one embodiment the cell density is about 2.75E6 cells/ml to about 3.25E6 cells/ml. In one embodiment the cell density is about 2.75E6 cells/ml to about 3.00E6 cells/ml. In one embodiment the cell density is about 2.75E6 cells/ml to about 2.75E6 cells/ml. In one embodiment the cell density is about 2.75E6 cells/ml to about 2.50E6 cells/ml. In one embodiment the cell density is about 3.0E6 cells/ml to about 4.0E6 cells/ml. In one embodiment the cell density is about 3.0E6 cells/ml to about 3.75E6 cells/ml. In one embodiment the cell density is about 3.0E6 cells/ml to about 3.50E6 cells/ml. In one embodiment the cell density is about 3.0E6 cells/ml to about 3.25E6 cells/ml. In one embodiment the cell density is about 3.25E6 cells/ml to about 4.0E6 cells/ml. In one embodiment the cell density is about 3.25E6 cells/ml to about 3.75E6 cells/ml. In one embodiment the cell density is about 3.25E6 cells/ml to about 4.0E6 cells/ml. In one embodiment the cell density is about 3.50E6 cells/ml to about 4.0E6 cells/ml. In one embodiment the cell density is about 3.50E6 cells/ml to about 3.75E6 cells/ml. In one embodiment the cell density is about 3.75E6 cells/ml to about 4.0E6 cells/ml.

In one embodiment, during expansion, fresh culture media is added to the bioreactor by a combination of fed batch/perfusion feeding and/or by perfusion. In one embodiment, fresh culture media is added by fed batch/perfusion until the culture reaches a volume of at least 1 liter, then the culture is switched to perfusion until harvest. In one embodiment the culture is perfused throughout expansion until harvest. In one embodiment during expansion the perfusion rate is at least one bioreactor bag volume per day. In one embodiment the perfusion rate is less than one bioreactor bag volume per day. In one embodiment the perfusion rate is greater than one bioreactor bag volume per day.

In one embodiment, during expansion, fresh culture media is added to the bioreactor by fed batch and/or perfusion. In one embodiment the perfusion rate is less than one bioreactor bag volume per day. In one embodiment during expansion the perfusion rate is at least one-half bioreactor bag volume per day. In one embodiment the perfusion rate is one bioreactor bag volume per day. In one embodiment the perfusion rate is greater than one bioreactor bag volume per day. In one embodiment the perfusion rate is double the bioreactor volume per day. In one embodiment the bioreactor bag volume is 500 ml. In one embodiment, during expansion, fresh culture media is added by fed batch until the culture reaches a volume of about 500 ml. In one embodiment, once the volume of culture media in the bioreactor has reached 500 ml, culture media is perfused at a rate of about 200 to 1000 ml per day. In one embodiment, during expansion, media is perfused at a rate of about 200 ml per day. In one embodiment, during expansion, media is perfused at a rate of about 500 ml per day. In one embodiment, during expansion, media is perfused at a rate of about 1000 ml per day.

In one embodiment the volume of the culture media in bioreactor is incrementally increased to 1000 ml during expansion to maintain a cell density of about 2E6 to about 4E6 nucleated cells/ml. In one embodiment the bioreactor volume is increased from at least 200 ml to at least 1000 ml. In one embodiment the bioreactor volume is increased from at least 300 ml to at least 1000 ml. In one embodiment the bioreactor volume is increased from at least 400 ml to at least 1000 ml. In one embodiment the bioreactor volume is increased from at least 500 ml to at least 1000 ml. In one embodiment the bioreactor volume is increased from at least 600 ml to at least 1000 ml. In one embodiment the bioreactor volume is increased from at least 700 ml to at least 1000 ml. In one embodiment the bioreactor volume is increased from at least 800 ml to at least 1000 ml. In one embodiment the bioreactor volume is increased from at least 900 ml to at least 1000 ml. In one embodiment the bioreactor volume is increased from at least 200 ml to at least 900 ml. In one embodiment the bioreactor volume is increased from at least 300 ml to at least 900 ml. In one embodiment the bioreactor volume is increased from at least 400 ml to at least 900 ml. In one embodiment the bioreactor volume is increased from at least 500 ml to at least 900 ml. In one embodiment the bioreactor volume is increased from at least 600 ml to at least 900 ml. In one embodiment the bioreactor volume is increased from at least 700 ml to at least 900 ml. In one embodiment the bioreactor volume is increased from at least 800 ml to at least 900 ml. In one embodiment the bioreactor volume is increased from at least 200 ml to at least 800 ml. In one embodiment the bioreactor volume is increased from at least 300 ml to at least 800 ml. In one embodiment the bioreactor volume is increased from at least 400 ml to at least 800 ml. In one embodiment the bioreactor volume is increased from at least 500 ml to at least 800 ml. In one embodiment the bioreactor volume is increased from at least 700 ml to at least 800 ml. In one embodiment the bioreactor volume is increased from at least 700 ml to at least 800 ml. In one embodiment the bioreactor volume is increased from at least 300 ml to at least 700 ml. In one embodiment the bioreactor volume is increased from at least 200 ml to at least 800 ml. In one embodiment the bioreactor volume is increased from at least 400 ml to at least 800 ml. In one embodiment the bioreactor volume is increased from at least 500 ml to at least 800 ml. In one embodiment the bioreactor volume is increased from at least 600 ml to at least 800 ml. In one embodiment the bioreactor volume is increased from at least 700 ml to at least 800 ml. In one embodiment the bioreactor volume is increased from at least 200 ml to at least 700 ml. In one embodiment the bioreactor volume is increased from at least 200 ml to at least 700 ml. In one embodiment the bioreactor volume is increased from at least 300 ml to at least 700 ml. In one embodiment the bioreactor volume is increased from at least 400 ml to at least 700 ml. In one embodiment the bioreactor volume is increased from at least 500 ml to at least 700 ml. In one embodiment the bioreactor volume is increased from at least 600 ml to at least 700 ml. In one embodiment the bioreactor volume is increased from at least 200 ml to at least 600 ml. In one embodiment the bioreactor volume is increased from at least 300 ml to at least 600 ml. In one embodiment the bioreactor volume is increased from at least 400 ml to at least 600 ml. In one embodiment the bioreactor volume is increased from at least 500 ml to at least 600 ml. In one embodiment the bioreactor volume is increased from at least 200 ml to at least 500 ml. In one embodiment the bioreactor volume is increased from at least 300 ml to at least 500 ml. In one embodiment the bioreactor volume is increased from at least 400 ml to at least 500 ml. In one embodiment the bioreactor volume is increased from at least 200 ml to at least 400 ml. In one embodiment the bioreactor volume is increased from at least 300 ml to at least 400 ml. In one embodiment the bioreactor volume is at least 200 ml, 250 ml, 300 ml, 350 ml, 400 ml, 450 ml, at least 500 ml, at least 550 ml, at least 600 ml, at least 650 ml, at least 700 ml, at least 750 ml, at least 800 ml, at least 850 ml, at least 900 ml, at least 950 ml, at least 1000 ml, or above 1000 ml. In one embodiment the bioreactor volume is at least 200 ml. In one embodiment the bioreactor volume is at least 300 ml. In one embodiment the bioreactor volume is at least 400 ml. In one embodiment the bioreactor volume is at least 500 ml. In one embodiment the bioreactor volume is at least 600 ml. In one embodiment the bioreactor volume is at least 700 ml. In one embodiment the bioreactor volume is at least 800 ml. In one embodiment the bioreactor volume is at least 900 ml. In one embodiment the bioreactor volume is at least 1000 ml. In one embodiment the bioreactor volume is greater than 1000 ml.

In one embodiment, as the culture volume and/or cell density increases, the rocking rate increases. In one embodiment the rocking rate increases from at least 2 rpm to at least 3 rpm. In one embodiment the rocking rate increases from at least 2 rpm to at least 4 rpm. In one embodiment the rocking rate increases from at least 2 rpm to at least 5 rpm. In one embodiment the rocking rate increases from at least 2 rpm to at least 6 rpm. In one embodiment the rocking rate increases from at least 3 rpm to at least 4 rpm. In one embodiment the rocking rate increases from at least 3 rpm to at least 5 rpm. In one embodiment the rocking rate increases from at least 3 rpm to at least 6 rpm. In one embodiment the rocking rate increases from at least 4 rpm to at least 5 rpm. In one embodiment the rocking rate increases from at least 4 rpm to at least 6 rpm. In one embodiment the rocking rate increases from at least 5 rpm to at least 6 rpm. In one embodiment the rocking rate is at least 2 rpm at a 2° angle. In one embodiment the rocking rate is at least 3 rpm, at a 3° angle. In one embodiment the rocking rate is at least 4 rpm at a 4° angle. In one embodiment the rocking rate is at least 5 rpm at a 5° angle. In one embodiment the rocking rate is at least 6 rpm at a 6° angle.

In one embodiment, as the volume of the culture media is incrementally increased to 1000 ml, the rocking rate is incrementally increased to 6 rpm. In one embodiment the volume of the culture media in the bioreactor bag at the start of expansion is about 300 ml at a rocking rate of 2 rpm at a 2° angle maintained at a perfusion rate of one bioreactor bag volume a day. In one embodiment when the culture reaches a cell density of 4E6 nucleated cells/ml, the volume of the culture media in the bioreactor bag is increased to 600 ml with a perfusion rate of one bioreactor bag volume per day at a rocking rate of 4 rpm at a 4° angle. In a related embodiment when the culture reaches a density of 4E6 nucleated cells/ml, the volume of the culture media in the closed single use bioreactor bag is increased to 1000 ml with perfusion rate of one bioreactor bag volume per day, at a rocking rate of 6 rpm at a 6° angle.

In one embodiment, as the volume of the culture is incrementally increased to 500 ml, the rocking rate is incrementally increased to 6 rpm at an angle of 6°. The cells are expanded in the closed single use bioreactor bag at a first culture volume of about 300 ml of culture media at a first rocking rate of about 2 rpm at an angle of 2° until the cells reach a predetermined cell density, then culturing the cells at a second culture volume of about 400 ml at a second rocking rate of about 5 rpm at an angle of 5° until the cells reach a predetermined cell density, then culturing the cells at a third culture volume of about 500 ml at a third rocking rate of about 6 rpm at an angle of 6° until the cells reach a predetermined cell density and maintaining the cells until harvest.

In one embodiment, when achieving a high transduction efficiency and/or TCR expression is more desired than a short expansion time, a higher initial inoculation cell density may be used and during expansion the expansion phase the volume of the culture is incrementally increased to 500 ml, the rocking rate is incrementally increased to 6 rpm at an angle of 6° cells in the closed single use bioreactor bag. Expansion begins by culturing the cells at a first culture volume of about 200 ml of culture media at a first rocking rate of about 2 rpm at an angle of 2° until the cells reach a predetermined cell density, then culturing the cells at a second culture volume of about 300 ml of culture media at a second rocking rate of about 3 rpm at an angle of 3° until the cells reach a predetermined cell density, then at a third culture volume of about 400 ml at the second rocking rate of about 3 rpm at an angle of 3° until the cells reach a predetermined cell density, then at the third culture volume of about 400 ml at a third rocking rate of about 4 rpm at an angle of 4° until the cells reach a predetermined cell density and maintaining the cells until harvest.

The invention provides a method for producing genetically engineered autologous T cells expressing at least one protein of interest, the method comprising inoculating a closed single use bioreactor bag containing culture media with apheresed donor cells and one or more soluble T cell activators, wherein at least one soluble T-cell activator is bound to at least one donor cell at the time of inoculation and the bioreactor bag is part of a rocking bioreactor platform; culturing the cells in the closed single use bioreactor bag continuously rocking at a rate of about 2 rpm at an angle of 2°; transducing the cells in the closed single use bioreactor bag with at least one soluble viral vector comprising a polynucleotide which encodes the protein of interest continuously rocking at a rate of about 2 rpm at an angle of 2°; expanding the cells in the closed single use bioreactor bag at a first culture volume of about 300 ml of culture media at a first rocking rate of about 2 rpm at an angle of 2° until the cells reach a predetermined cell density, then culturing the cells at a second culture volume of about 400 ml at a second rocking rate of about 5 rpm at an angle of 5° until the cells reach a predetermined cell density, then culturing the cells at a third culture volume of about 500 ml at a third rocking rate of about 6 rpm at an angle of 6° until the cells reach a predetermined cell density and maintaining the culture until harvest.

In one embodiment the cells are expanded for 7 to 14 days. In one embodiment the cells are expanded for 7 to 13 days. In one embodiment the cells are expanded for 7 to 12 days. In one embodiment the cells are expanded for 7 to 11 days. In one embodiment the cells are expanded for 7 to 10 days. In one embodiment the cells are expanded for 7 to 9 days. In one embodiment the cells are expanded for 7 to 8 days. In one embodiment the cells are expanded for 8 to 14 days. In one embodiment the cells are expanded for 8 to 13 days. In one embodiment the cells are expanded for 8 to 12 days. In one embodiment the cells are expanded for 8 to 11 days. In one embodiment the cells are expanded for 8 to 10 days. In one embodiment the cells are expanded for 8 to 9 days. In one embodiment the cells are expanded for 9 to 14 days. In one embodiment the cells are expanded for 9 to 13 days. In one embodiment the cells are expanded for 9 to 12 days. In one embodiment the cells are expanded for 9 to 11 days. In one embodiment the cells are expanded for 9 to 10 days. In one embodiment the cells are expanded for 10 to 14 days. In one embodiment the cells are expanded for 10 to 13 days. In one embodiment the cells are expanded for 10 to 12 days. In one embodiment the cells are expanded for 10 to 11 days. In one embodiment the cells are expanded for 11 to 14 days. In one embodiment the cells are expanded for 11 to 13 days. In one embodiment the cells are expanded for 11 to 12 days. In one embodiment the cells are expanded for 12 to 14 days. In one embodiment the cells are expanded for 12 to 13 days. In one embodiment the cells are expanded for 13 to 14 days. In one embodiment the cells are expanded for 7, 8, 9, 10, 11, 12, 13, 14, or more days. In one embodiment the cells are expanded for at least 7 days. In one embodiment the cells are expanded for at least 8 days. In one embodiment the cells are expanded for at least 9 days. In one embodiment the cells are expanded for at least 10 days. In one embodiment the cells are expanded for at least 11 days. In one embodiment the cells are expanded for at least 12 days. In one embodiment the cells are expanded for at least 13 days. In one embodiment the cells are expanded for at least 14 days.

In one embodiment, the cells are expanded at 34-39° C. In one embodiment, the cells are expanded at 34-35° C. In one embodiment, the cells are expanded at 35-37° C. In one embodiment, the cells are expanded at 35-36° C. In one embodiment, the cells are expanded at 36-37° C. In one embodiment, the cells are expanded at 34° C., 35° C., 36° C., or 37° C. In one embodiment, the cells are expanded at 34° C. In one embodiment, the cells are expanded at 35° C. In one embodiment, the cells are expanded at 36° C. In one embodiment, the cells are expanded at performed at 37° C.

"Engineered T cells" and "genetically engineered T cells", are used interchangeable and refer to T cells that have been modified by the introduction of extra genetic material, in particular, polynucleotides encoding proteins of interest, such as receptors expressed on a cell surface. Examples of cell surface receptors include chimeric antigen receptors (CAR) and T-cell receptors (TCR). The terms "isolated engineered T cell" and "isolated genetically engineered T cells" specifically refer to T cells that have been modified or manipulated, such as genetic modification, or not normally found in nature. As used herein, T cell or T lymphocyte refers to a type lymphocyte that actively participates in the body's immune response.

The terms "polynucleotide" and "nucleic acid molecule" are used interchangeably throughout and include both single-stranded and double-stranded nucleic acids and includes genomic DNA, RNA, mRNA, cDNA, or synthetic origin or some combination thereof which is not associated with sequences normally found in nature. The terms "isolated polynucleotide" or "isolated nucleic acid molecule" specifically refer to sequences of synthetic origin or those not normally found in nature. Isolated nucleic acid molecules comprising specified sequences may include, in addition to the specified sequences, coding sequences for up to ten or even up to twenty other proteins or portions thereof or may include operably linked regulatory sequences that control expression of the coding region of the recited nucleic acid sequences, and/or may include vector sequences. The nucleotides comprising the nucleic acid molecules can be ribonucleotides or deoxyribonucleotides or a modified form of either type of nucleotide. The modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate.

The terms "polypeptide" or "protein" are used interchangeably throughout and refer to a molecule comprising two or more amino acid residues joined to each other by peptide bonds. Polypeptides and proteins also include macromolecules having one or more deletions from, insertions to, and/or substitutions of the amino acid residues of the native sequence, that is, a polypeptide or protein produced by a naturally-occurring and non-recombinant cell; or is produced by a genetically-engineered or recombinant cell, and comprise molecules having one or more deletions from, insertions to, and/or substitutions of the amino acid residues of the amino acid sequence of the native protein. Polypeptides and proteins also include amino acid polymers in which one or more amino acids are chemical analogs of a corresponding naturally-occurring amino acid and polymers. Polypeptides and proteins are also inclusive of modifications including, but not limited to, glycosylation, lipid attachment, sulfation, gamma-carboxylation of glutamic acid residues, hydroxylation and ADP-ribosylation. Polypeptides and proteins of interest can be of scientific or commercial interest, including those useful as components of cell therapy therapeutics. Proteins of interest include, among other things, membrane-bound proteins.

The invention provides a method for producing engineered T cells that express a protein of interest. In one embodiment the protein of interest is a cell surface receptor. The cell surface receptor is a genetically engineered receptors such as T cell receptors (TCRs) and chimeric antigen receptors (CARs or CAR-T cells, TRUCKs (chimeric antigen receptors that redirect T cells for universal cytokine-mediated killing), and armored CARs (designed to modulate an immunosuppressive environment)) and as well as other proteins comprising an antigen binding molecule that interacts with that targeted antigen. These engineered receptors are expressed on the surface of the T cell. In one embodiment the cell surface receptor is a T cell receptor or a chimeric antigen receptor.

TCRs are membrane anchored heterodimer protein complexes comprising an $\alpha$ chain and a $\beta$ chain complexed with the invariant CD3 chain molecules. The variable domain of the TCR $\alpha$- and $\beta$-chains each have three complementarity-determining regions (CDRs) that recognize a peptide derived from the protein presented by/bound within the groove of an MHC/HLA molecule, and a constant domain that engages in disulfide bonding to link the chains together. CD3 and zeta activate the T lymphocyte through signal transduction. The TCR have the potential to recognize antigens presented on the surface of numerous cells, such as cancer cells, inflammatory cells and cells from other sources.

CARs are engineered transmembrane proteins, comprising an extracellular domain, typically comprising an antigen binding protein or domain that binds to an antigen of interest, a hinge region, a transmembrane domain, and an intracellular (cytoplasmic) domain.

The extracellular domain may be derived either from a synthetic or from a natural source, such as the proteins described herein. The extracellular domains often comprise a hinge portion, sometimes referred to as a "spacer" region. Hinges may be derived from the proteins as described herein, particularly the c0-stimulatory proteins described herein, as well as immunoglobulin (Ig) sequences or other suitable molecules to achieve the desired special distance from the target cell.

A transmembrane domain may be fused to the extracellular or intracellular domain of the CAR. The transmembrane domain may be derived either from a synthetic or from a natural source, such as the proteins described herein, particularly the costimulatory proteins described herein.

An intracellular (cytoplasmic) domain may be fused to the transmembrane domain and can provide activation of at least one of the normal effector functions of the immune cell. Effector function includes cytolytic activity or helper activity including the secretion of cytokines. Intracellular domains can be derived from the proteins described herein, particularly from CD3.

CARs can be engineered to bind to an antigen (such as a cell-surface antigen) by incorporating an antigen binding molecule that interacts with that targeted antigen. CARs typically incorporate an antigen binding domain (such as scFv) in tandem with one or more costimulatory ("signaling") domains and one or more activating domains.

In one embodiment the antigen binding molecule is an antibody fragment thereof, and more preferably one or more single chain antibody fragment ("scFv"). scFvs are preferred for use in CARs because they can be engineered to be expressed as part of a single chain along with the other CAR components. See Krause et al., J. Exp. Med., 188(4): 619-626, 1998; Finney et al., Journal of Immunology, 161: 2791-2797, 1998.

CARs incorporate one or more costimulatory (signaling) domains to increase their potency. See U.S. Pat. Nos. 7,741,465, and 6,319,494, as well as Krause et al. and Finney et al. (supra), Song et al., Blood 119:696-706 (2012); Kalos et al., Sci Transl. Med. 3:95 (2011); Porter et al., N. Engl. J. Med. 365:725-33 (2011), and Gross et al., Annu. Rev. Pharmacol. Toxicol. 56:59-83 (2016). Suitable costimulatory domains can be derived from, among other sources, CD28, CD28T, OX40, 4-1BB/CD137, CD2, CD3 (alpha, beta, delta, epsilon, gamma, zeta), CD4, CD5, CD7, CD8, CD9, CD16, CD22, CD27, CD30, CD 33, CD37, CD40, CD 45, CD64, CD80, CD86, CD134, CD137, CD154, PD-1, ICOS, lymphocyte function-associated antigen-1 (LFA-1 (CD1 la/CD18), CD247, CD276 (B7-H3), LIGHT (tumor necrosis factor superfamily member 14; TNFSF14), NKG2C, Ig alpha (CD79a), DAP-10, Fc gamma receptor, MHC class I molecule, TNF, TNFr, integrin, signaling lymphocytic activation molecule, BTLA, Toll ligand receptor, ICAM-1, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CDl-ld, ITGAE, CD103, ITGAL, CDl-la, LFA-1, ITGAM, CDl-lb, ITGAX, CDl-lc, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, 41-BB, GADS, SLP-76, PAG/Cbp, CD19a, CD83 ligand, or fragments or combinations thereof. The costimulatory domain can comprise one or more extracellular portions, a transmembrane portion, and an intracellular portion.

CARs also include one or more activating domains. CD3 zeta is an element of the T cell receptor on native T cells and has been shown to be an important intracellular activating element in CARs.

Cell surface molecules can be targeted with a traditional CAR. Intracellular molecules can be targeted with TCRs that recognize a peptide derived from the protein presented by or bound within the groove of an MHC/HLA molecule. Such targets include alpha folate receptor, 5T4, AFP, ADAM 17, 17-A, ART-4, $\alpha_v\beta_6$ integrin, BAGE. Bcr-abl, BCMA, B7-H3, B7-H6, CAIX, CAMEL, CAP-1, Carbonic anhydrase IX, CASP-8, CDC27m, CD19, CD20, CD22, CD30, CD33, CD44, CD44v6, CD44v7/8, CD70 (CD27 L or TNFSF7), CD79a, CD79b, CD123, CD138, CD171, CDK4/m, cadherin 19 (CDH19), Placental-Cadherin (CDH3), CEA, CLL-1, CSPG4, CT, Cyp-B, DAM, DDL3, EBV, EGFR, EGFRvIII, EGP2, EGP40, ELF2M, ErbB2 (HER2), EPCAM, EphA2, EpCAM, ETV6-AML1, FAP, fetal AchR, FLT3, FR$\alpha$, G250, GAGE, GD2, GD3, 'Glypican-3 (GPC3), GNT-V, GP-100, HAGE, HBV, HCV, HER-2/neu, HLA-A, HPV, HSP70, HST-2, hTERT, iCE, IgE, IL-11R$\alpha$, IL-13Ra2, Kappa, KIAA0205, LAGE, Lambda, LDLR/FUT, Lewis-Y, MAGE, MAGE1, MAGEB2, MART-1,/Melan-A, MC1R, MCSP, MUM-1, MUM-2, MUM-3, mesothelin (MSLN), Muc1, Muc16, Myosin/m, NA88-A, NCAM, NKG2D Ligands, NY-ESO-1, P15, p190 minor bcr-abl, PML/RARa, PRAME, PSA, PSCA, PSMA, RAGE, ROR1, RU1, RU2, SAGE, SART, SSX-1, SSX-2, SSX-3, Survivin, TAA, TAG72, TEL/AML1, TEMs, TPI, TRP-1, TRP-2, TRP-2/INT2, VEGFR2 and WT1. See also, Löffler et al., Blood 85(6): 2098-2103, 15 Mar. 2000; Wolf et al., Drug Discovery Today 10(8): 1237-1244, September 2005; Baeuerle & Reinhardt, Cancer Res 69(12): 4941-4944, Jun. 15, 2009; Baeuerle et al., Curr. Opin, Mol. Ther. 11: 22-30, 2009; Nagorsen & Baeuele, Exp Cell Res 317:1255-1260, 2011; Nagorsen et al., Pharmacology & Therapeutics 136: 334-342, 2012; Huehls et al., Immunology and Cell Biology 93:290-296, 2015; and Stieglmaier et al., Expert Opin Biol Ther 15(8): 1093-1099, 2015.

The process could be used for producing T cells expressing the CD19 CARs, such as Tisagenlecleucel (Kymriah™) and axicabtagene ciloleucel (Yescarta®).

In one embodiment the cell surface receptor recognizes an antigenic target associated with a target cell such as a cell surface molecule or an intermolecular molecule. The target cell is any cell that presents an antigen that is recognized by the gene of interest. In one embodiment the target cell is a cancer cell. A cancer cell is a cell associated with a cancer, including cells associated with metastatic tumors, solid tumors, blood cancers, brain cancers, breast cancers, colon cancers, kidney cancers, lung cancers, liver cancers, ovarian cancers, pancreatic cancers, prostate cancers, skin cancers, spleen cancers, stomach cancers, thyroid cancers.

Greater transduction efficiency allows for delivering a smaller, more effective dose to the patient. When fewer T cells transduced with the gene of interest are produced there are fewer genetically engineered T cells available for administration to the patient resulting in a less effective dose. The method described herein achieves a high transduction rate (high transgene expression greater than 40% on CD8 T cells) at a lower lentiviral vector MOI. Less lentiviral vector is required to make more engineered T cells expressing the protein of interest, the method is more efficient and cost effective. The invention provides a method for increasing the transgene expression in genetically engineered autologous T cells expressing a protein of interest, the method comprising inoculating a closed single use bioreactor bag containing culture media with apheresed donor cells and one or more soluble T cell activators, wherein at least one soluble T-cell activator is bound to at least one donor cell at the time of inoculation and the bioreactor bag is part of a rocking bioreactor platform, culturing the cells in the closed single use bioreactor bag continuously rocking at a rate of about 2 rpm, transducing the cells in the closed single use bioreactor bag with at least one soluble viral vector comprising a polynucleotide which encodes the protein of interest continuously rocking at a rate of about 2 rpm, and expanding the cells in the closed single use bioreactor bag at a rocking rate of about 2 rpm and increasing the culture volume and rocking the rate as needed to maintain the culture until harvest, wherein the transgene expression is greater than the transgene expression of genetically engineered autologous T cells derived from an enriched population of T cells from the same apheresed donor cells and expressing the same protein of interest.

Genetically engineered T cells are recovered by harvesting when the cell density has reached a desired or predetermined state or at a predetermined or desired time point. The genetically engineered T cells may be recovered from the bioreactor using methods known in the art, such as separation using gravity or centrifugation. The cells may also be recovered using semiautomated and fully automated cell separation systems, including blood separation systems. Such systems are commercially available and include Sepax® 2 and Sefia™ S-2000 Cell Processing Systems (GE Healthcare), Cobe 2991 cell processor (Terumo BCT, Lakewood, CO, CellSaver 5 (Haemonetics, (Boston, MA), and the like. The recovered cells are typically washed and concentrated into a suitable formulation for administration to the patient and for cryopreservation.

With the method described herein, cell yields of greater than 10 billion with a viability of greater than 90% are seen in a 10 day process. Yields greater than 20 billion were seen after when cell expansion was extended for several more days.

Samples may be taken during expansion and/or at harvest for quality control testing. Such QC tests may include those that quantify the transduction efficiency of the genetically engineered T cells such as determining % TCR on cell surface using flow cytometry and determining vector copy number using qPCR to measure integration. Viability can also be tested before releasing the product to be delivered to the patient.

Standard procedures known in the art may be used for cryopreservation of recovered genetically engineered T cells for storage and/or preparation for use in a human subject. In one embodiment the recovered cells are eluted at 2E8 cells/ml in saline supplemented with 1% HSA and were further formulated at a 1:1 ratio with Hyclone cryopreservation media (GE Healthcare) supplemented with 5% human serum albumin.

A fraction of the formulated engineered T cells, as well as any apheresed cells not used in the method, can be cryopreserved by methods known in the art to provide a permanent source of such cells for the future treatment of the patient.

When needed for treatment, the cryopreserved genetically engineered T cells are thawed and diluted into a saline buffer or other suitable media for administration to the donor by infusion in a treatment-effective amount. Suitable infusion media can be any isotonic medium formulation, typically normal saline, Normosol™ R (Abbott) or Plasma-Lyte™ A (Baxter), but also 5% dextrose in water or Ringer's lactate can be utilized. The infusion medium can be supplemented with human serum albumin. The volume is typically kept minimal as possible, a pharmaceutically acceptable dose is based on the number and viability of the cells, the indication to be treated and the patient. Therapeutic doses are typically between a few million and a few billion cells, depending on the patient's condition and need, among other factors. An exemplary dose may be ≤100 ml at about 100E6 cells/ml.

The invention provides a method of treating a patient with genetically engineered autologous T cells expressing a protein of interest comprising, incubating apheresed cells from the patient with one or more T cell activators selected from the group consisting of an anti CD3 antibody, an anti CD2 antibody, and an anti CD28 antibody or binding fragments thereof, to allow for saturation of antibody binding, inoculating a closed single use bioreactor bag containing culture media with the apheresed cells, wherein the bioreactor bag is part of a rocking bioreactor platform, culturing the cells in the closed single use bioreactor bag continuously rocking at a rate of about 2 rpm, transducing the cells in the closed single use bioreactor bag with at least one soluble viral vector comprising a polynucleotide which encodes the protein of interest continuously rocking at a rate of about 2 rpm, and expanding the cells in the closed single use bioreactor bag at a rocking rate of about 2 rpm, increasing the culture volume and rocking the rate as needed to maintain the culture at a desired cell density until harvest, harvesting and formulating the cells for cryopreservation, freezing the cells and storing until needed for administering to the patient, thawing and resuspending the cells in a suitable media for infusion, and reintroducing a pharmaceutically effective amount of the genetically engineered autologous T cells expressing the protein of interest into the patient.

The formulated engineered T cells may be administered either alone, or as a pharmaceutical composition in combination with diluents and/or with other components such as IL-2 or other cytokines or cell populations.

Methods are provided for using the engineered T cells for treating conditions, indications, diseases, disorders and the like. The T cell expresses a gene of interest, such as a cell surface receptor, recognizes an antigenic target associated with a target cell that is associated with the condition, indication, disease, disorder or the like. Such conditions, diseases or disorders including cancers, tumors, solid tumors, hematologic disorders, leukemia, lymphomas, viral infections, inflammatory disease or disorders, and/or autoimmune disease or disorders. In one embodiment of the invention, the genetically engineered T cells are used to treat an indication in a subject. In one embodiment of the invention, genetically engineered T cells are used to treat a cancer patient. In some embodiments, the invention provides creating a T cell-mediated immune response in a donor, comprising administering to the donor an effective amount of an engineered autologous T cell that expresses a protein of interest. In some embodiments, the T cell-mediated immune response is directed against a target cell or cells. In some embodiments, the engineered autologous T cell comprises a genetic construct expressing one or more chimeric antigen receptors, T cell receptors and/or other proteins of interest. In some embodiments, the target cell is a tumor cell. In some embodiments, the invention comprises a method for treating or preventing an indication, said method comprising administering to a subject in need thereof an effective amount of a genetically engineered autologous T cell made by the method described herein. In some aspects, the invention comprises a method for treating or preventing inflammatory and/or autoimmune disorders.

While the terminology used in this application is standard within the art, definitions of certain terms are provided herein to assure clarity and definiteness to the meaning of the claims. Units, prefixes, and symbols may be denoted in their SI accepted form. Numeric ranges recited herein are inclusive of the numbers defining the range and include and are supportive of each integer within the defined range. The methods and techniques described herein are generally performed according to conventional methods well known in the art and as described in various general and more specific references that are cited and discussed throughout the present specification unless otherwise indicated. All documents, or portions of documents, cited in this application, including but not limited to patents, patent applications, articles, books, and treatises, are hereby expressly incorporated by reference.

The present invention is not to be limited in scope by the specific embodiments described herein that are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims. What is described in an aspect or embodiment of the invention can be combined with other aspects and/or embodiments of the invention.

EXAMPLES

Example 1 Comparison Study of Three Processes

1: Autologous T cells generated with the closed continuous autologous T cell bioprocessing method where activation to expansion is conducted in a XURI® W25 Cell Expansion System. "Xuri W25 bioreactor".

2: A bioprocessing system where activation to expansion is conducted in G-REX® 6 and 24 well plates. "G-Rex".

3: Hybrid bioprocessing system where activation and transduction are conducted in a gas permeable bag followed by T cell expansion in a XURI® W25 Cell Expansion System. "Permeable bag".

In addition, two different culture media supplemented with IL-2 (Media 1) or TWS119+IL7+IL-21 (Media 2), were also compared using the closed continuous autologous T cell bioprocessing system and the G-REX® plates.

T cell production was evaluated for its purity, phenotype, and in vitro properties.

On day 0, a fresh LEUKOPACK® (Hemacare, Northridge, CA), containing 300 ml fresh leukapheresis product collected from normal peripheral blood was sterile welded to a CD-600.1 Sepax Cell Separation Kit (GE) and processed under the Culture Wash-Pro program. The LEUKOPACK® contained leukocytes, erythrocytes, and platelets. The cells were washed in 1 L ClinMACS® PBS/EDTA, 5 ml human serum albumin (Miltenyi Biotec, San Diego, CA) to remove plasma and any apheresis buffers using a Sempax CPro Cell Separation System equipped with a CS-600.1 Kit (GE Healthcare), according to manufacturer's instructions. Based on the initial white blood cell (WBC) count indicated on the donor information sheet accompanying the LEUKOPACK®, the cells were eluted at a cell density of 150E6 WBC/ml with ~50 ml OpTmizer™ complete media.

The nucleated cells in the washed leukapheresed harvest sample were counted using NC200™ Automated Cell Counter ChemMetec, Denmark) and followed by determining total viable cell count, viability, and immunophenotyping of the washed cells.

1) Closed Continuous Autologous T Cell Bioprocess Using the a XURI® W25 Cell Expansion System. "Xuri W25 Bioreactor"

A portion of the washed apheresed donor cells comprising 1.2E9 nucleated cells was then transferred into two transfer bags (Charter Medicine, Winston-Salem, NC) under the Dilute program using the Sepax C-Pro processing system with the same CD-600.1 Kit. In to one bag was added about 8 ml of Media 1: (OpTmizer™ complete media containing 300 IU/mL rhIL-2 (ThermoFisher)). In to the second bag was added about 8 ml of Media 2: (OpTmizer™ complete media containing 5 uM TWS119 (Cayman Chemical, Ann Arbor, MI), 20 ng/ml IL7 (Stemcell Technologies, Cambridge, MA) and 20 ng/ml IL-21 (Stemcell Technologies)). Each bag was incubated with 7.5 ml ImmunoCult™ Human CD3/CD28/CD2 (25 μl/ml of cells, Stemcell Technologies) at room temperature for 1 hour to allow saturation of antibody binding. The concentration of the Immunocult™ added was determined on a final activation culture volume of 300 ml as described in the step below. OpTmizer™ complete media: OpTmizer™ T cell expansion medium (ThermoFisher, Waltham, MA), 2.5% CTS™ Immune Cell SR supplement (ThermoFisher), 2.6% CTS™ T cell supplement (ThermoFisher), 1% GlutaMax (ThermoFisher), 0.1% Pluronic F68 and 300 IU/ml IL-2.

A 2 L XURI® SP Perf Cellbag bioreactor (GE Healthcare) was connected to a XURI® Cell Expansion System W25 and 300 ml Media 1 was added and allowed to equilibrate at 37° C., 5% $CO_2$, gas flow rate of 0.1 L/min, and a rocking rate of 6 rpm at a 6° angle. A second 2 L XURI® SP Perf Cellbag bioreactor was also connected to a XURI® Cell Expansion System W25 and 300 ml Media 2 was similarly equilibrated.

The transfer bags containing the cells in Media 1 and Media 2 were sterile welded to the XURI® Cellbag feed-lines and the contents transferred into the bags by gravity. The cells were then cultured overnight at 37° C., 5% $CO_2$, gas flow rate 0.1 L/min at a rocking rate of 2 rpm at a 2° angle to allow for the activation of T cells.

On Day 1, the nucleated cells in each bag were counted. An amount of a lentiviral vector (comprising a polynucleotide encoding a TCR) that corresponded to a MOI of 1 functional titer was diluted in 10 ml of Media 1 or Media 2 and placed in transfer bags. The transfer bags were sterile welded on to the XURI® Cellbag feed-lines and lentivirus was transferred into each of the bioreactors via gravity flow. The cells were incubated at 37° C., 5% $CO_2$, gas flow rate of 0.1 L/min, and a rocking rate of 2 rpm at a 2° angle, for 20-24 hours.

On Day 2, about half the volume of the culture media in each bioreactor bag was exchanged using three 50 ml bag washouts through feed-line and waste-line. Cell counts were taken daily and viable cell density (VCD) and viability were determined using NC200™ Automated Cell Counter (ChemMetec), dissolved oxygen and metabolites were also measured. Cell phenotypes were determined for all samples tested. The bags were maintained on the rocking bioreactors at 2 rpm at a 2° angle, 37° C., 5% $CO_2$, gas flow rate of 0.1 L/min, for 24 hours.

On Days 3-7, additional OpTmizer™ complete media containing either the IL-2 (Media 1) or TWS119/IL17/IL-21 (Media 2), was added by fed batch/perfusion feeds to a final volume of 1 L to both cultures, to maintain the cell density above 2E6 cells/ml. As volume increased, the rocking speed and angle was increase to 4 rpm at a 4° angle, to maintain a cell density at the desired level.

Total viable cell density, viability, glucose and lactate measurements were taken each day. Phenotyping was determined on days 3, 5 and 7.

On Days 7-10, both cultures were switched to perfusion feeding at a rate of one bag volume/day. Both bioreactor bags were now fed with Media 1. As cell density increased, dissolved $O_2$ levels were maintained at 80% by feedback control.

Total viable cell density, viability, glucose, and lactate measurements were made each day. Phenotyping was done on day 10.

The cells were harvested on Day 10. The XURI® SP Per bioreactor bags were sterile welded to a Selfia 5200 Cell Processing System using the FlexCell program and CT-800.1 Cell Processing kit (GE Healthcare. The T cells were concentrated to ~20 ml at a 75 ml/min flow rate. One wash cycle was performed using 0.9% saline (Baxter, Deerfield, Ill) supplemented with 1% vol human serum albumin (HSA). The wash was performed at 380×g for 5 min.

Cells were reconstituted in equal volume saline plus 1% HSA plus HyClone™ Cryopreservation Media (GE Healthcare) supplemented with 5% HSA and cryopreserved by freezing to −80° C. using the control rate freezer Via Freeze™ (GE Healthcare) and storing in liquid nitrogen.

2. G-REX® Plates "G-Rex".

The cells were cultured in 24-well or 6-well G-REX® (WilsonWolf, New Brighton, MN) plates following manufacturer's protocols, using Media 1 and Media 2. 1E6 cells/well were seeded in the G-REX® plates and activated with ImmunoCult™ Human CD3/CD28/CD2 (25 ug/ml media with cells) on day 0. Approximately 24 hours after activation, cells were seeded at 1E6 cells/well (concentration 2E6 cells/mL) and an amount of the same lentiviral vector (comprising a polynucleotide encoding a TCR), corresponding to a MOI of 1 functional titer was added to each well. On day 2, Media 1 and Media 2 was added to the full capacity of the wells (total 6 mL) to dilute the virus. The media was changed, and the cells were fed every 2-3 days.

Cell counts were taken daily and viable cell density (VCD) and viability were determined using a NC200™

Automated Cell Counter (ChemoMetec), dissolved oxygen and metabolites were also measured. Cell phenotypes were determined for all samples tested.

3. Hybrid Bioprocessing System, Activation and Transduction Conducted in a Gas Permeable Bag Followed by T Cell Expansion in a XURI® W25 Cell Expansion System. "Perfusion Bag".

Washed apheresed donor cells comprising 500E6 nucleated cells was transferred into a gas permeable bag (OriGen, Austin, TX) with 6 ml ImmunoCult™ Human CD3/CD28/CD2 and incubated at 37° C., 5% $CO_2$ for 24 hours.

The nucleated cells were counted. An amount of the same lentiviral vector (comprising a polynucleotide encoding a TCR), corresponding to a MOI of 1 functional titer was added directly to the bag using a syringe and incubated overnight at 37° C., 5% $CO_2$.

The cells were then split into two gas permeable bags the following day and were incubated in the bags at 37° C., 5% $CO_2$, until a total of 1 billion nucleated cells.

The cells were then inoculated into 2 L XURI® SP Perf Cellbag bioreactor bags on a XURI® W25 Cell Expansion System (GE Healthcare) containing 300 ml OpTmizer™ complete media containing 300 IU/ml IL-2, and rocked at a rate of 6 rpm at a 6° angle. The bioreactor was scaled up to a 1 L volume 24 hours following inoculation. Fresh media was perfused at 500 ml/day for 1 day, followed by 1 L/day until harvest.

Cell counts were taken daily and viable cell density (VCD) and viability were determined using a NC200™ Automated Cell Counter (ChemoMetec), dissolved oxygen and metabolites were also measured. Cell phenotypes were determined for all samples tested.

The cells were harvested, concentrated and further formulated at a 1:1 ratio with HyClone™ Cryopreservation Media (GE Healthcare) supplemented with 5% HSA and cryopreserved by freezing to 100° C. using a Via Freeze™ (GE Healthcare) and storing in liquid nitrogen. Viability and recovery at harvest were measured.

Results

Figure 1B:
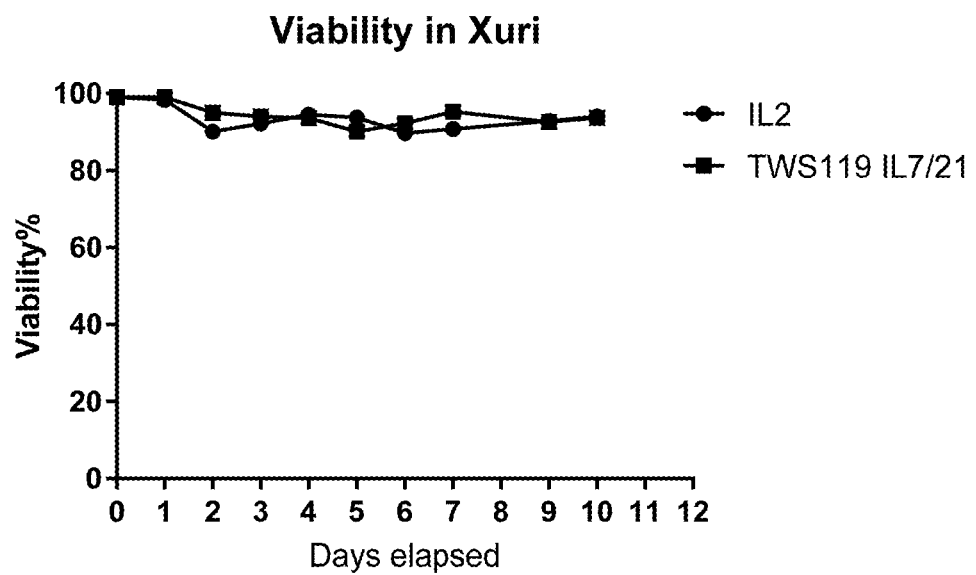

FIG. 1 Shows the growth curve and TCR expression at harvest for the T cells produced under Condition 1, the closed continuous autologous T cell bioprocess using the XURI® W25 bioreactor. FIG. 1A shows the growth curve of cell expansion in the XURI® W25 bioreactor with media supplemented with IL-2 only or the cocktail of IL7, IL-21, and TWS119. Media with IL-2 yielded 16 billion T cells in 10 days while media with IL7, IL-21, and TWS119 yielded 12 billion T cells in 10 days. FIG. 1B shows the viability of cell expanded in the XURI® W25 bioreactor with media supplemented with IL-2 only or the IL7, IL-21, and TWS119 cocktail. Cell viability was above 90% throughout expansion and no difference in cell viability was observed between the different media conditions.

Figure 2:
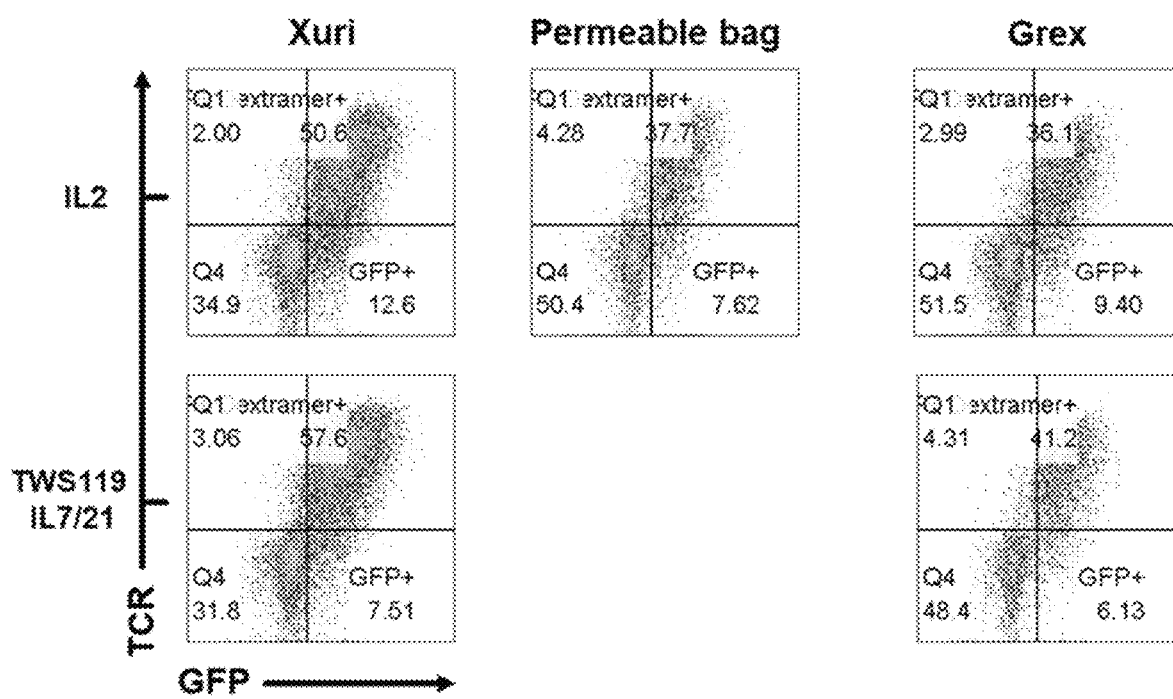
FIG. 2. T cell transgene expression from engineered T cells expressed in the three systems: XURI® W25 bioreactor ("Xuri"), combination of static perfusion bag and XURI® W25 bioreactor ("Permeable Bag") and G-Rex® plates ("G-Rex").

FIG. 2 shows T cell transgene expression under different conditions. All cells were transduced with the same lentiviral vector at a MOI=1 one day after activation. The transgene was more highly expressed in the cells transduced in the XURI® W25 bioreactor compared with cells transduced in the Permeable bag (Hybrid condition 3) or in the G-REX® system (condition 2).

Figure 3:
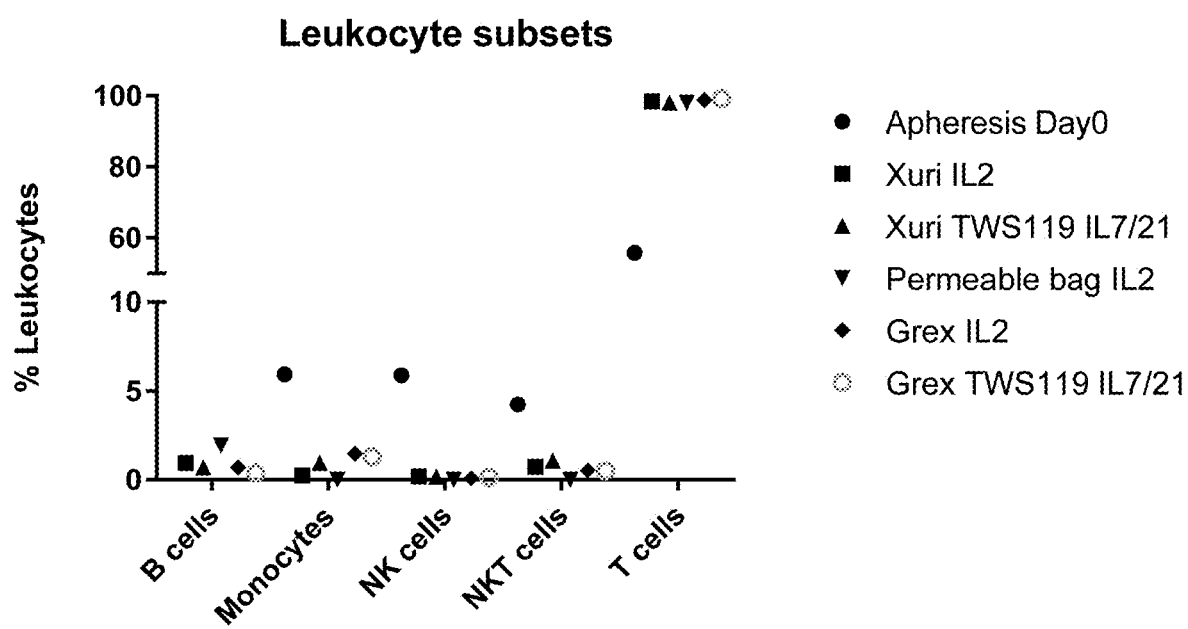
FIG. 3. Leukocyte subsets in harvested engineered T cells expressed in the three systems: XURI® W25 bioreactor ("Xuri"), combination of static perfusion bag and XURI® W25 bioreactor ("Permeable Bag") and G-REX® plates ("G-Rex").

FIG. 3 shows the leukocyte subsets in harvested T cells from the different test conditions. Analysis of human B cells (CD19), monocytes (CD14), NK cells (CD56/16), NKT cells (CD3+CD56+), and T cells (CD3+Cd56−) were performed by immunophenotyping. T cell purity in all conditions were above 98% and no significant difference in the percentage of non-T cells subsets was seen among the different conditions.

Figure 4A:
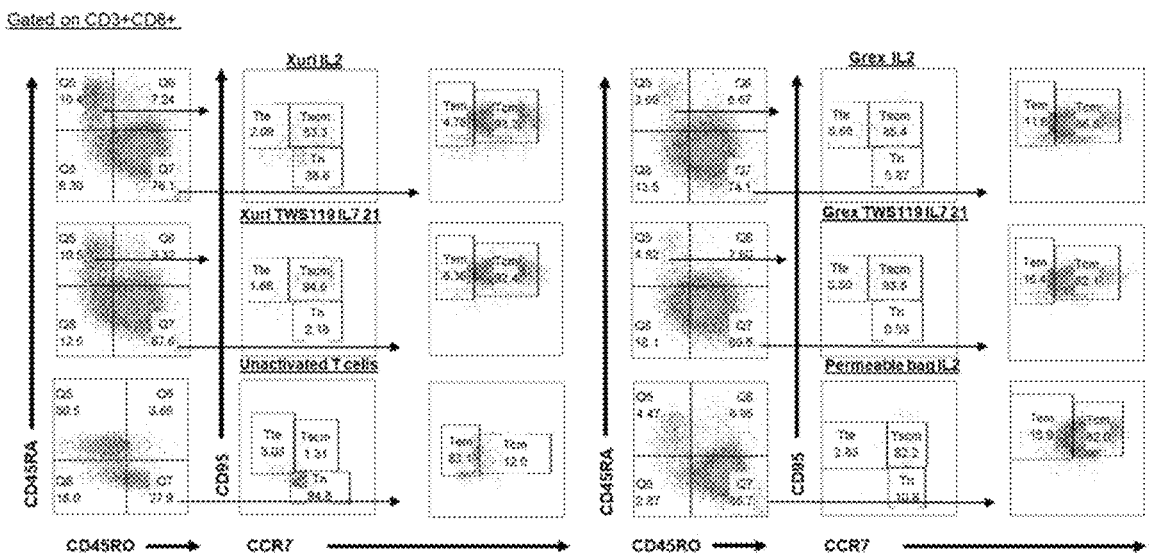
FIG. 4. Percentage of T cells subsets on Day 5 (A) and Day 10 (B) from engineered T cells expressed in the three systems: XURI® W25 bioreactor ("Xuri"), combination of static perfusion bag and XURI® W25 bioreactor ("Permeable Bag") and G-REX® plates ("G-Rex").
Figure 4B:
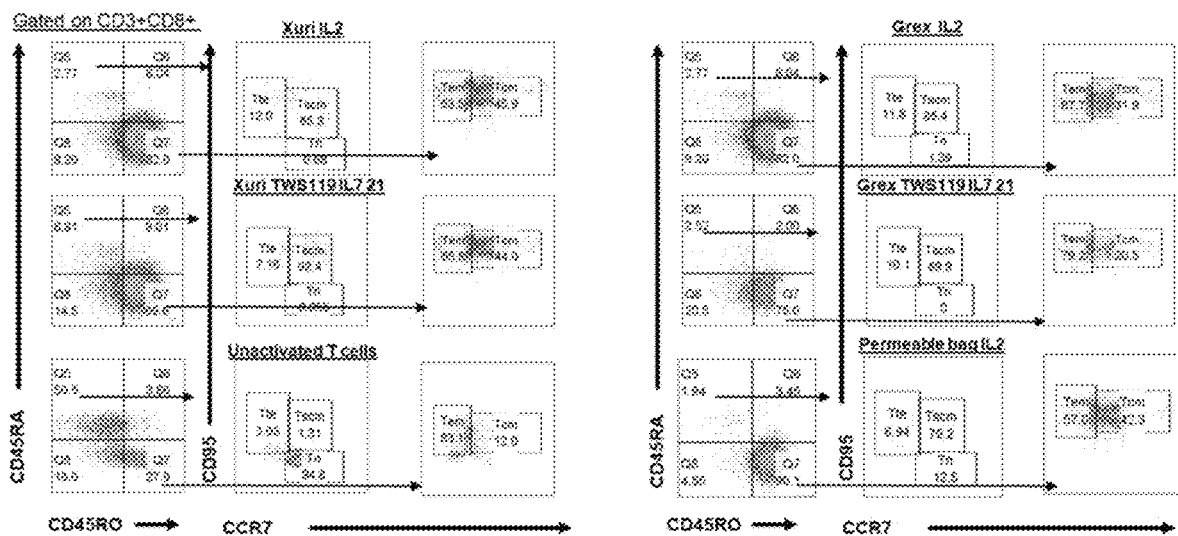

FIG. 4 shows the percentage of T cells subsets on Day 5 (A) and Day 10 (B) under different conditions. Tscm, Tcm, Tem, and Tte subsets were analyzed by immunophenotyping based on their expression of CD45RA, CD45RO, CD95, and CCR7. T cells produced in the XURI® W25 bioreactor had a higher percentage of Tscm and Tcm than T cells produced in the G-REX® system or Permeable bag on Day 5 and a higher percentage of Tcm on Day 10 than T cells that was produced in the G-REX® system, indicating a less differentiated phenotype.

Figure 5A:
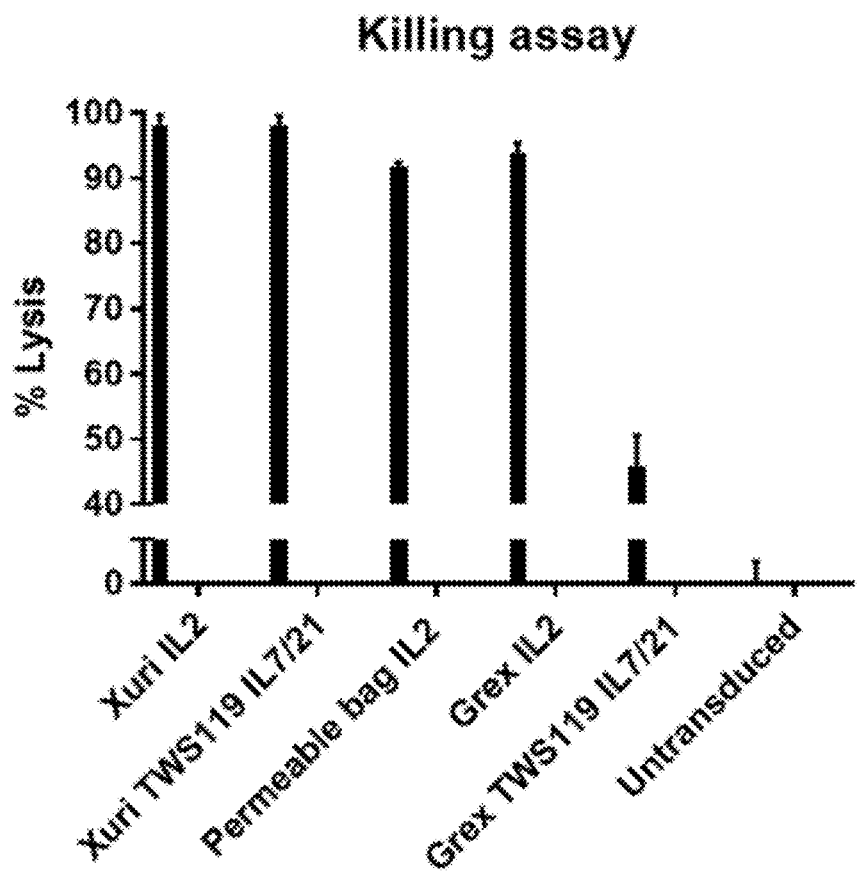
FIG. 5. Shows the cytotoxic function of engineered T cells characterized by their ability in target cell lysis (A), IFN-gamma release in response to target cells (B), and TNF-alpha release in response to target cells (C).
Figure 5B:
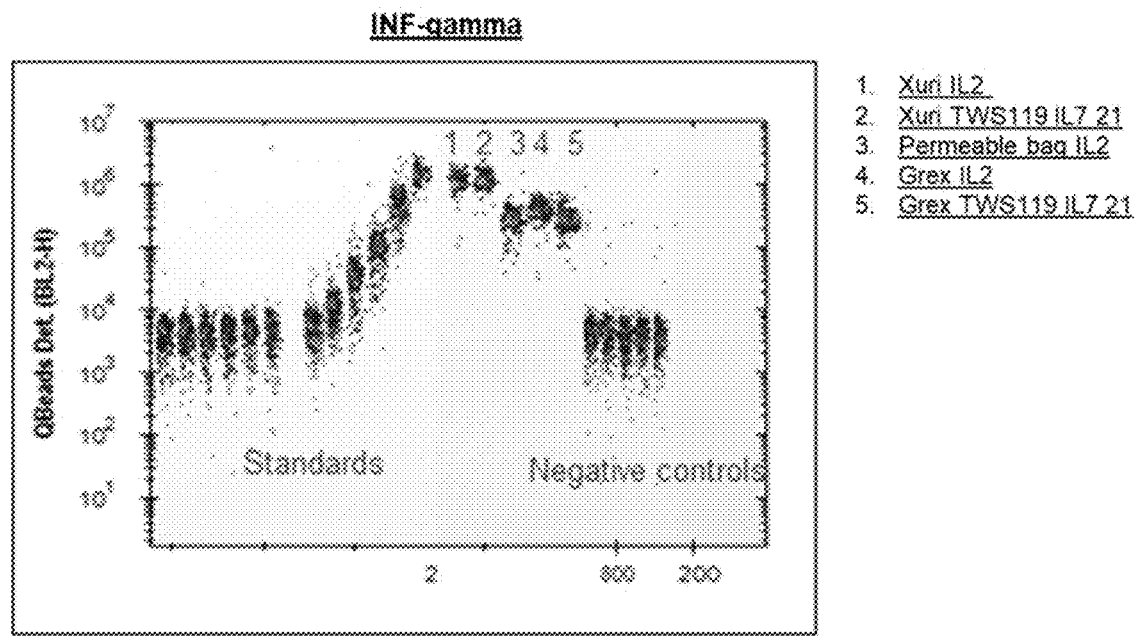
Figure 5C:
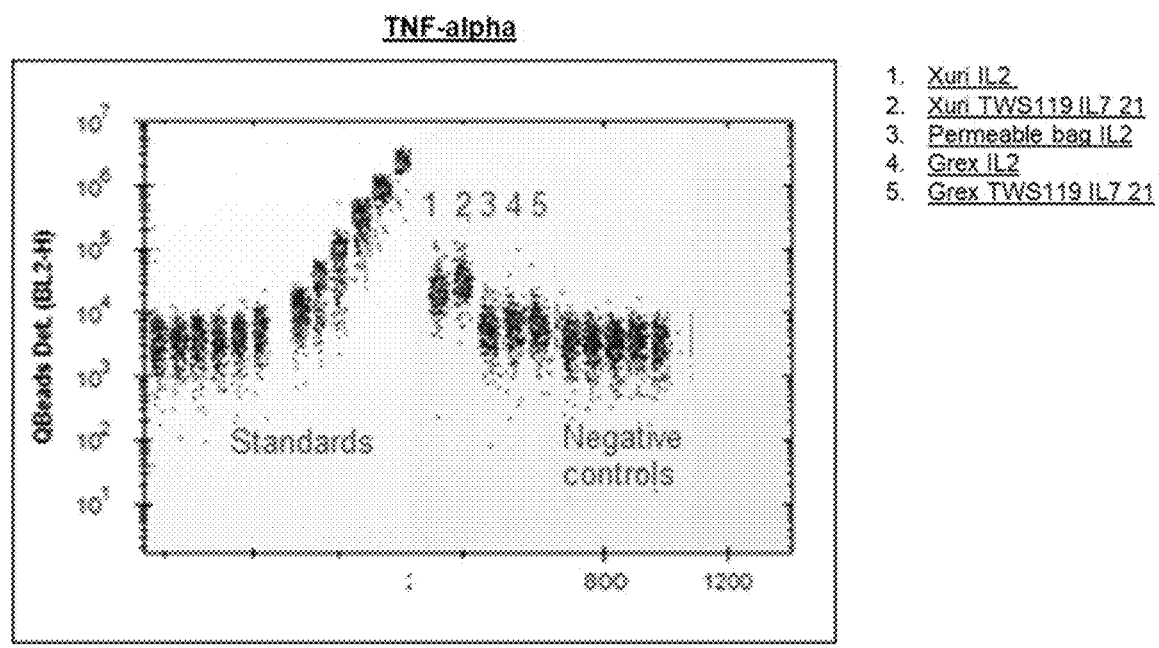

FIG. 5 shows the cytotoxic function of engineered T cells characterized by their ability in target cell lysis (A), IFN-gamma release in response to target cells (B), and TNF-alpha release in response to target cells (C). Briefly, harvested T cells and peptide-pulsed T2 cells were co-cultured together at a ratio of 1:1. The T2 cells were Luiferase engineered, and luminescence was determined using a Steady-Glo® Luciferase Assay System (Promega, Madison, WI). The decrease of luminescence was used to quantify the cell death of T2 cells as an indicator of the cytotoxicity of engineered T cells. As shown in the figures, engineered T cells generated in the XURI® W25 bioreactor under the two media conditions (IL-2 or IL7, IL-21, TWS119) were both more potent in killing target cells (A), possibly due to their stronger release of IFN-gamma (B) and TNF-alpha (C), than engineered T cell generated in the static Permeable bag and the static G-REX® system.

Figure 6A:
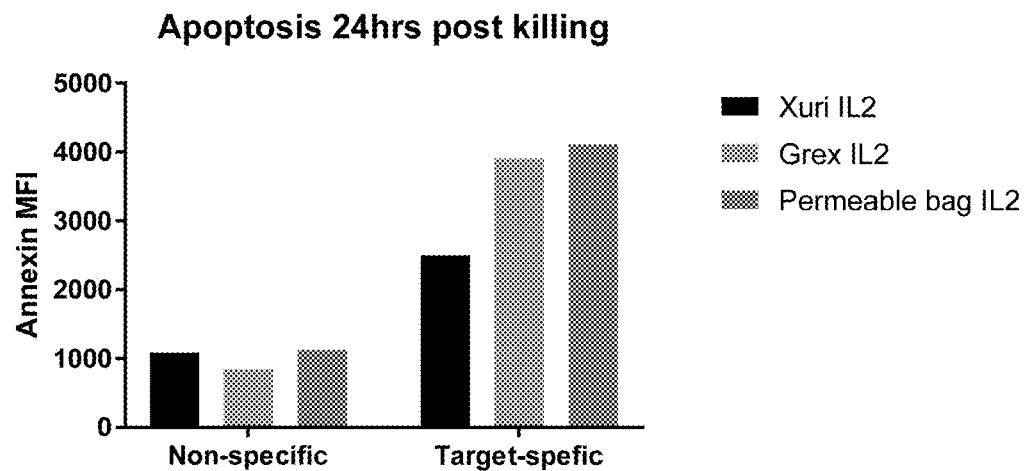
FIG. 6. Resistance to target cell challenge of engineered T cells expressed in the three systems: XURI® W25 bioreactor ("Xuri"), combination of static perfusion bag and XURI® W25 bioreactor ("Permeable Bag") and G-REX® plates ("G-Rex"). Annexin level (A), Tim3 (B).
Figure 6B:
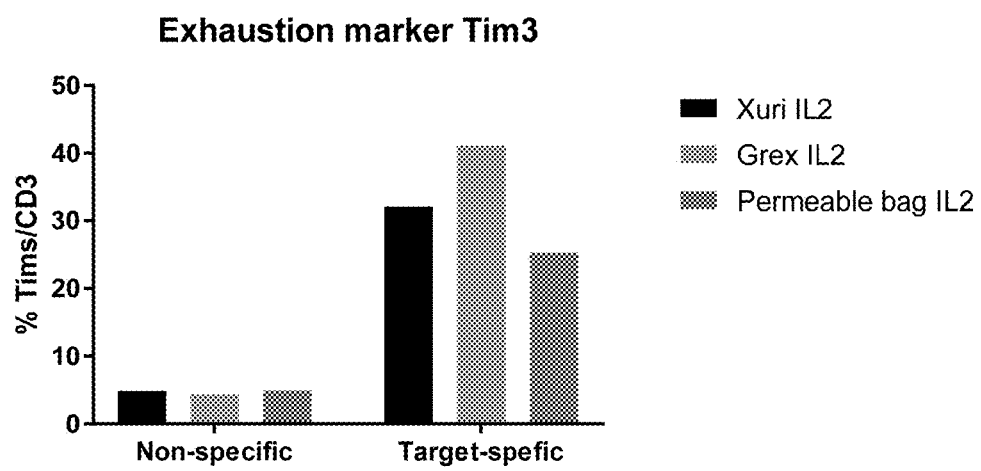

FIG. 6 shows resistance to target cell challenge of engineered T cells, characterized by their level of annexin (A) and expression of exhaustion marker Tim3 (B) after co-culturing with target cells in vitro at effector to target (E:T) ratio at 1:1. Externalization of phosphatidylserine in apoptotic cells was detected using recombinant annexin V conjugated to violet-fluorescent Pacific Blue™ dye. T cells with effector phenotype are susceptible to activation with target cell challenge and will become apoptotic after activation, thus a lower level of annexin should indicate T cells with more memory subsets. As shown in the figures, engineered T cells generated from the XURI® W25 bioreactor had lower level of annexin than cells from G-REX® system or Permeable bag in response to target cell challenge, thus are more memory phenotype-like. (A). In addition, engineered T cells generated in the XURI® W25 bioreactor and Permeable bag had lower expression of exhaustion marker Tim3 compared with cells from G-REX® system (B).

The closed continuous autologous T cell bioprocessing method was compared with the static G-REX® and hybrid gas permeable bag/XURI® system in their ability to generate autologous lentiviral engineered T cells. The closed continuous method produced T cells with higher transgene expression, higher level of cytokine secretion, and more memory-like phenotype when compared with T cells transduced in the static G-REX® system or the static gas permeable bag.

Example 2 Addition of a Glycolysis Inhibitor to the Culture Media

On day 0, a fresh LEUKOPACK® (Hemacare, Northridge, CA), containing 300 ml fresh leukapheresis product collected from normal peripheral blood was sterile welded to a CD-600.1 Sepax Cell Separation Kit (GE Healthcare) and processed under Culture Wash-Pro program. The LEUKOPACK® comprised leukocytes, erythrocytes, and platelets. The cells were washed in 1 L Clin-MACS® PBS/EDTA, 5 ml human serum albumin (Miltenyi Biotec) to remove plasma and apheresis buffers using a Sempax CPro Cell Separation System equipped with a CS-600.1 Kit (GE Healthcare), according to manufacturer's instructions. The cells were washed and counted as described above in Example 1.

A portion of the washed aphered donor cells comprising 1.2E9 nucleated cells were transferred into two transfer bags under the Dilute program using Sepax C-Pro processing system with the same CS-600.1 Kit (a new kit was not used). Into one bag was added about 8 ml of Media 1 (OpTmizer™ complete media containing 300 IU/mL rhIL-2 (ThermoFisher) and 2 mM 2-Deoxy-D-glucose (2-DG) (MilliporeSigma, Burlington, MA)). Into the second bag was added about 8 ml of Media 2 (OpTmizer™ complete media containing 300 IU/mL rhIL-2 (ThermoFisher)). To each was added 7.5 ml Immunocult™ anti-CD3/CD28/CD12 (25 µl/ml media with cells, Stemcell Technologies). The amount of activator was determined based on the culture volume of 300 ml that was used in the culture/activation step below. The bags were incubated for 1 hour at room temperature to allow for saturation of antibody binding.

A 2 L XURI® SP Perf Cellbag bioreactor (GE Healthcare) was connected to a XURI® Cell Expansion System W25 and 300 ml Media 1 was added and allowed to equilibrate at 37° C., 5% $CO_2$, gas flow rate of 0.1 L/min, and a rocking rate of 6 rpm at a 6° angle. A second 2 L XURI® SP Perf Cellbag bioreactor was also connected to a XURI® Cell Expansion System W25 and 300 ml Media 2 was similarly equilibrated.

The transfer bags containing the cells in Media 1 and Media 2 were sterile welded to the XURI® Cellbag feedlines and the contents transferred into the bags by gravity. The cells were then incubated overnight at 37° C., 5% $CO_2$, gas flow rate 0.1 L/min at a rocking rate of 2 rpm at a 2° angle.

On Day 1, the nucleated cells in each bag were counted and the amount of a lentiviral vector (comprising a polynucleotide encoding a TCR) corresponding to a MOI of 1 functional titer was diluted in 10 ml of Media 1 or Media 2 and placed in transfer bags. The transfer bags were sterile welded on XURI® Cellbag feed-lines and the lentivirus was then transferred into each of the bioreactors via gravity flow. The cells were incubated at 37° C., 5% $CO_2$, gas flow rate of 0.1 L/min, and a rocking rate of 2 rpm at a 2° angle, for 20-24 hours.

On Day 2, about half the volume of the culture media in each bioreactor bag was exchanged using three 50 ml bag washouts through feed-line and waste-line. Cell counts were taken daily and viable cell density (VCD), viability, dissolved oxygen, metabolites were determined as described above. Cell phenotypes were determined for all samples tested. The bags were maintained on the rocking bioreactors at 2 rpm at a 2° angle, 37° C., 5% $CO_2$, gas flow rate of 0.1 L/min, for 24 hours.

On Days 3-9, additional OpTmizer™ complete media containing either IL-2/2-DG (Media 1) and IL-2 (Media 2), were added by fed batch/perfusion feeds to 1 L, to maintain the cell density above 2E6 cells/ml. As the culture volume increased, the rocking speed and angle were increase to 4 rpm at a 4° angle, to maintain a sufficient mass transfer in bioreactors. Media 1 containing 2-DG was perfused out with OpTmizer™ complete media containing only IL-2 (Media 2) when culture volume reached 1 L. In a separate experiment, OpTmizer™ complete media containing 2-DG was maintained until harvest.

Total viable cell density, viability, glucose and lactate measurements were taken each day. Phenotyping was determined on Days 3, 5 and 7.

On Days 9-14, both cultures were switched to 1 L/day perfusion feeding, and rocking was set at 6 rpm at a 6° angle. Total viable cell density, viability, glucose, lactate measurements were made each day. Phenotyping was done on Day 14.

Total viable cell density, viability, glucose and lactate measurements were taken each day. Phenotyping was determined on Days 9 and 14.

The cells were harvested on Day 14. The XURI® SP Per bioreactor bags were sterile welded to a Selfia 5200 Cell Processing System using the FlexCell program and CT-800.1 Cell Processing kit (GE Healthcare). T cells were concentrated to ~20 ml at a 75 ml/min flow rate. One wash cycle was performed using 0.9% saline (Baxter, Deerfield, Ill) supplemented with 1% vol human serum albumin (HSA). The wash was performed at 380×g for 5 min.

Viability and harvest recovery were measured. The cells were concentrated and further formulated at a 1:1 ratio with Hyclone supplemented with 5% human serum albumin and cryopreserved by freezing to −80° C. using a Via Freeze™ (GE Healthcare) and storing in liquid nitrogen Results During antigen stimulation, T cells shift to a glycolytic metabolism to sustain effector function. However, the role of glucose metabolism in T cell differentiation during in vitro expansion is unclear. It was hypothesized in this study that glucose metabolism, in particular glycolysis, supported T cell differentiation into effector phenotype during expansion and pharmacological inhibition of glycolysis via 2-DG could attenuate CD3/CD28/CD2 antigen-mediated differentiation and promote a memory phenotype. In this experiment, 2-DG was added to cells with the activators to inhibit glycolysis following T cell activation. 2-DG was then either removed later in the expansion phase to allow restoration of glycolysis to support cell expansion or kept in through the entire process until harvest. The engineered T cells derived from 2-DG-inhibited T cells differentiation produced more Tscm and Tcm compared with the T cells derived from the media without 2-DG. This resulted in a greater T cell yield, greater transgene expression, and a more memory-like phenotype of the T cells.

Figure 7A:
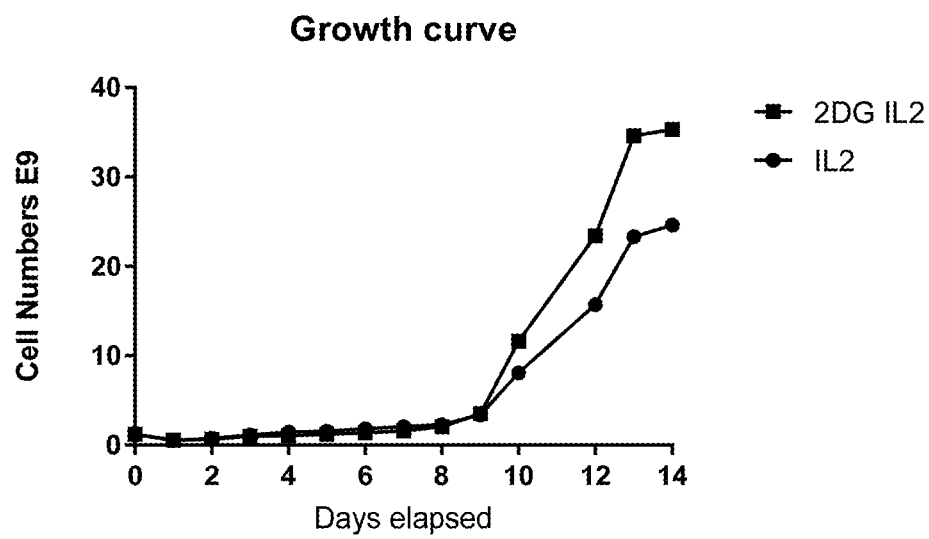
FIG. 7. Growth curve (A) and viability (B) for cells expanded in media supplemented with 2-DG (Media 1) and without 2-DG (Media 2).

FIG. 7 shows the growth curve (A) and viability (B) cells expanded in media supplemented with (Media 1) 2-DG and without 2-DG (Media 2). Media containing 2-DG yielded 35 billion T cells in 14 days while medium condition without 2-DG yielded 25 billion T cells in 14 days. Overall viability was above 70% with the cells from the 2-DG media having a slightly higher viability than those from non-2-DG media from Day 4 to Day 10. This drop of viability during Days 4-10 was possibly due to cell death of non-T cell leucocytes. Viability returned to higher than 90% until harvest after the T cell population was enriched to greater than 90% in the cultures. With 2-DG checking the brake on T cells differentiating into Tem, less cytotoxic cytokine release associated with decreased Tem population may also have contributed to higher viability in the samples containing the 2-DG media.

Figure 8:
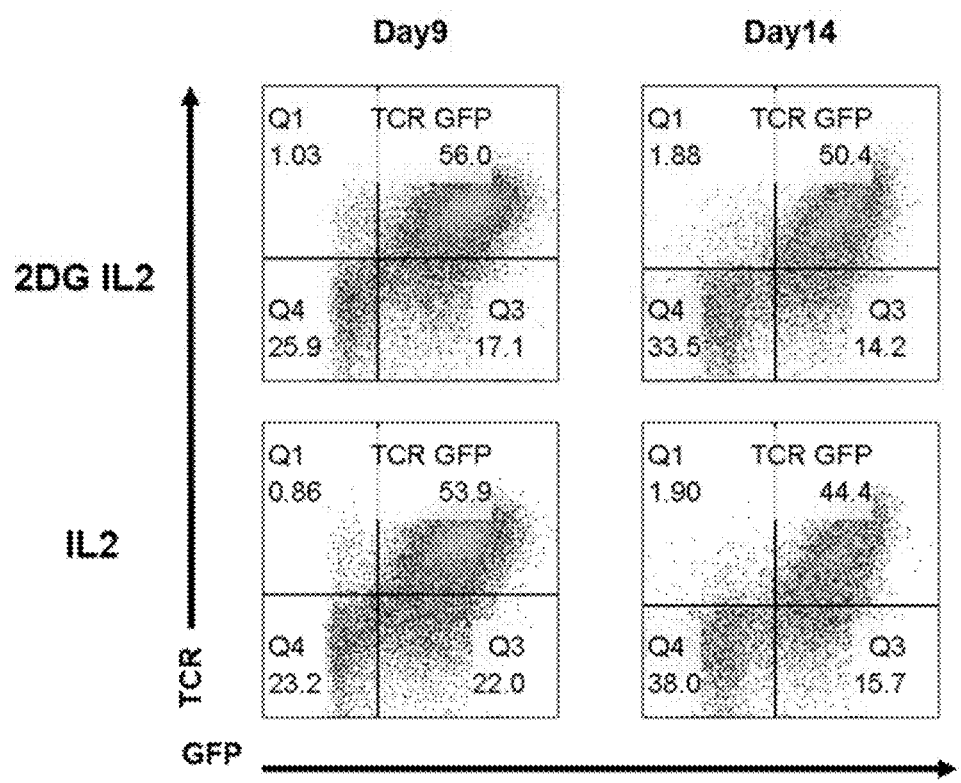
FIG. 8. Transgene expression of cells expanded in the media supplemented with 2-DG (Media 1) and without 2-DG (Media 2).

FIG. 8 shows transgene expression of cells expanded in the media supplemented with 2-DG (Media 1) and without 2-DG (Media 2). Transgene expression by T cells in 2-DG media was slightly higher than that of T cells in non-2-DG media (56% vs 54%) and was able to maintain at a high level (50.4%) when cell density was as high as 35 billion cells/ml.

In contrast, transgene expression of T cell in non-2-DG media decreased to 44.4% at high cell density (25 billion cells/ml).

Figure 9:
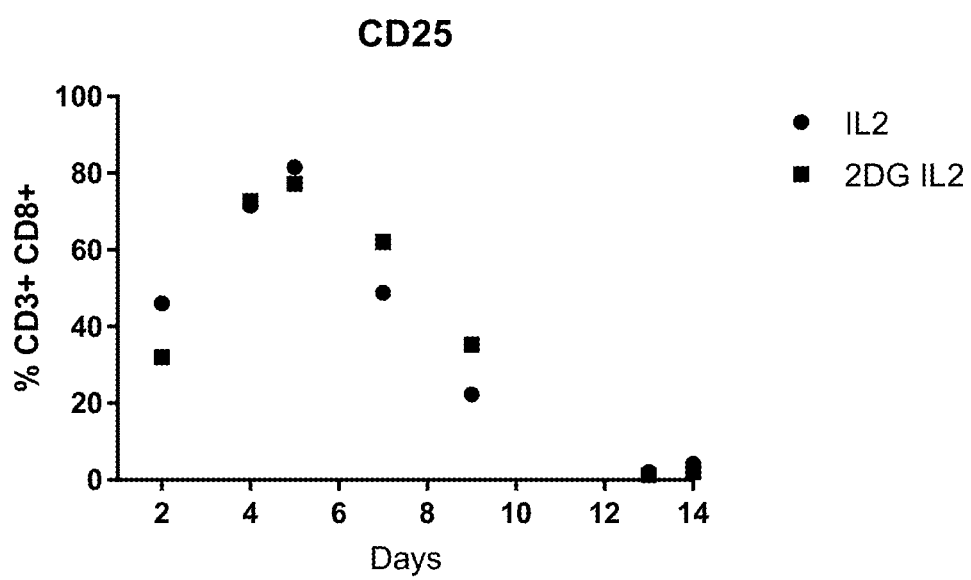
FIG. 9. CD25 expression by cells expanded in the media supplemented with 2-DG (Media 1) and without 2-DG (Media 2).

FIG. 9 shows CD25 expression by cells expanded in the media supplemented with 2-DG (Media 1) and without 2-DG (Media 2). CD25 expression by T cells in non-2-DG media showed a stronger response to activation that it expressed at a higher level than that of T cell in 2-DG media (46% vs 32%). Even through CD25 expression by T cells in both conditions saturated at ±80%. T cells in 2-DG media retained CD25 better at Days? and 9 than the cells in the non-2-DG media. This may be due to the higher transgene expression and T cell yield for T cells generated in the 2-DG media.

Figure 10A:
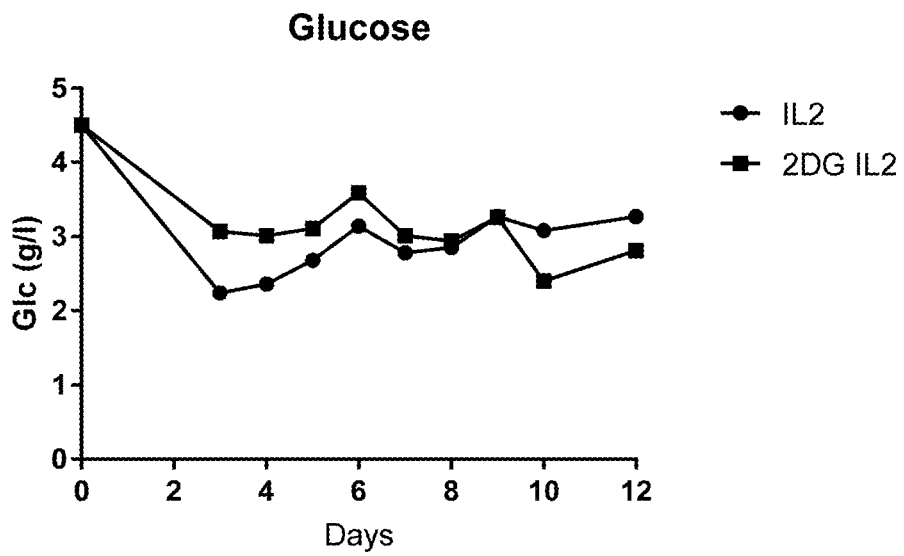
FIG. 10. Glucose (A) and lactate (B) concentrations in cultures supplemented with 2-DG (Media 1) and without 2-DG (Media 2).
Figure 10B:
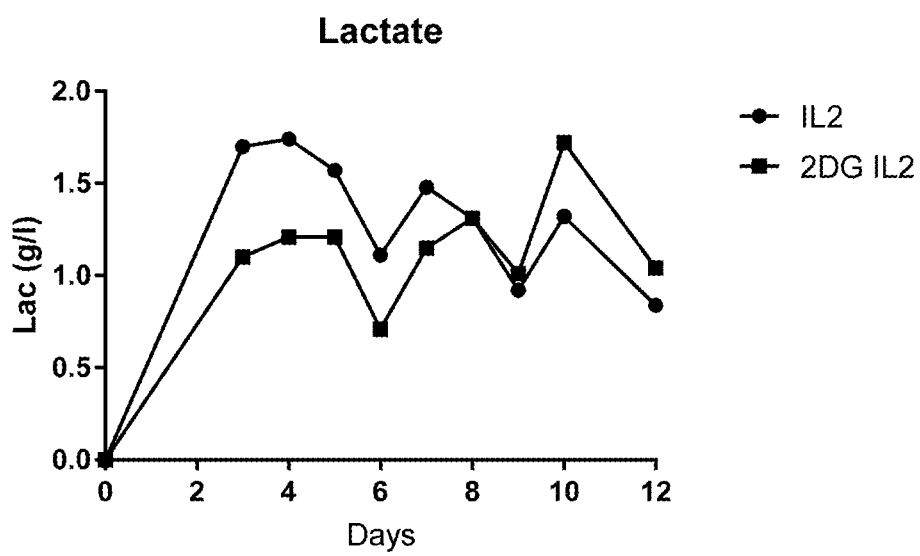

FIG. 10 shows glucose (A) and lactate (B) concentrations under the different media conditions. Glucose and lactate were measured using Cedex Bio Analyzer (Roche, Indianapolis, IN). Inhibition of glycolysis under the 2-DG media condition (Media 1) was evidenced by higher glucose concentration (lower glucose consumption) (A) and higher lactate concentration (B) in spent media compared to that from the non-2-DG condition (Media 2). In addition, the effect of 2-DG was reversible as restoration of glucose (A) and lactate (B) levels was found after removal of 2-DG from the media from Day 7 to 14.

Figure 11:
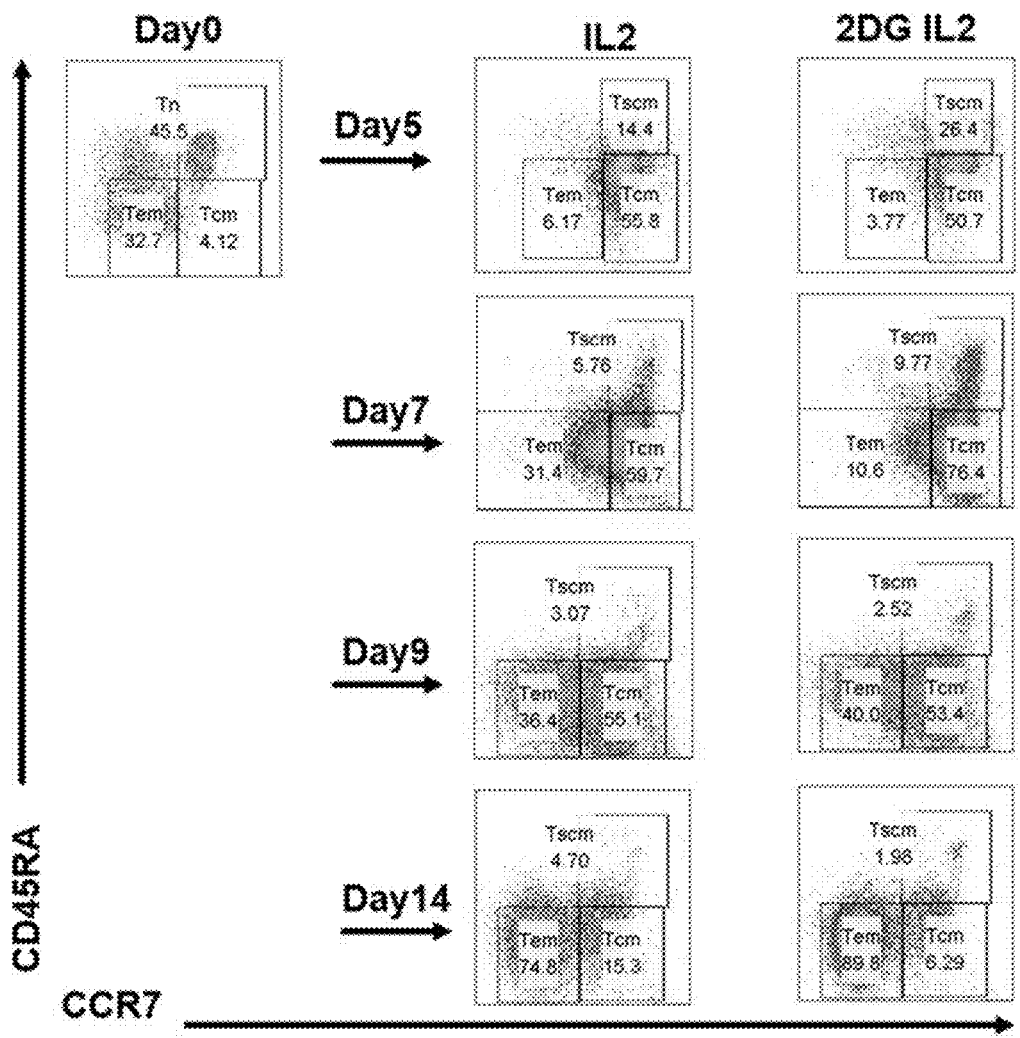
FIG. 11. T differentiation phenotyping of cells expanded media supplemented with (Media 1) and without 2-DG (Media 2).

FIG. 11 shows T cell differentiation phenotyping of cells expanded media supplemented with (Media 1) and without 2-DG (Media 2). 2-DG was added to culture medium between Days 0 and 7 and the feed medi was replaced with non-2-DG media (Media 1) from Days 7-14. The T cells in the 2-DG media were less differentiated, suggested by higher Tscm subset (26% vs 14%) at Day 5 and higher combined Tcm and Tscm (86% vs 56%) at Day 7. The T cells continued differentiation after 2-DG was perfused out from culture media and ended at a similar level of differentiation as T cells in non-2-DG media (Media 1).

Figure 12:
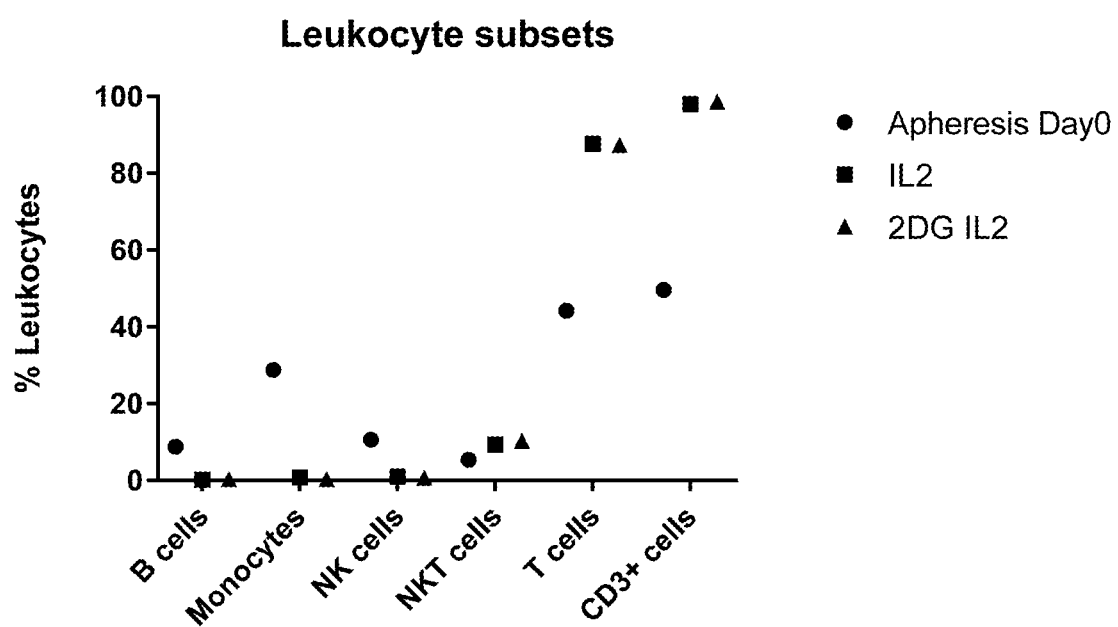
FIG. 12. Leukocyte subsets in harvested T cells of cells expanded media supplemented with (Media 1) and without 2-DG (Media 2).

FIG. 12 shows leukocyte subsets in harvested T cells under the different media conditions. Analysis of human B cells (CD19), monocytes (CD14), NK cells (CD56/16), NKT cells (CD3+CD56+), and T cells (CD3+Cd56−) were performed by immunophenotyping. Although NKT cells expanded from 5% to ±10%, CD3+ cell purity in both conditions was above 98% and no significant difference in the percentage of non-T cells subsets were found between 2-DG and non-2-DG media conditions.

Figure 13A:
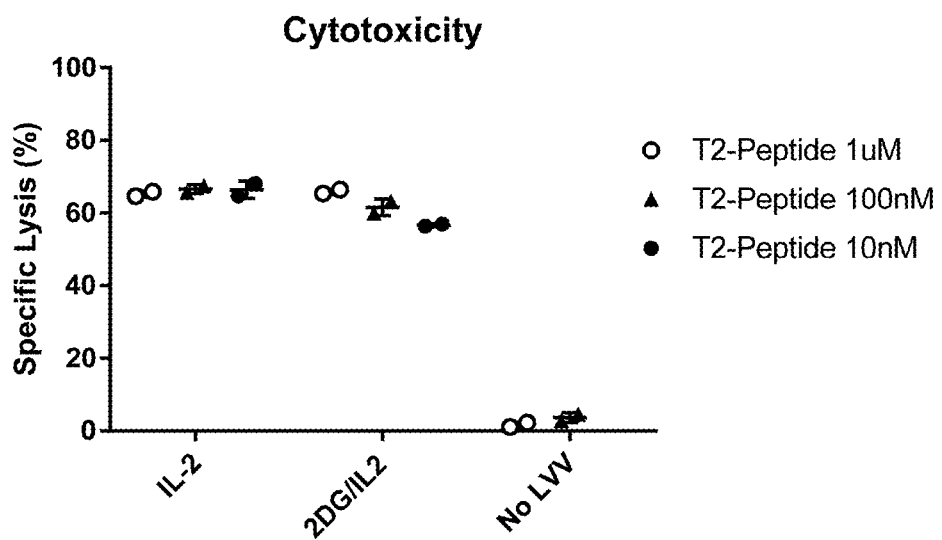
FIG. 13. Results from potency assays of engineered TCR T cells. (A) Cytotoxicity. (B) IFN-γ. (C) T cell differentiation.
Figure 13B:
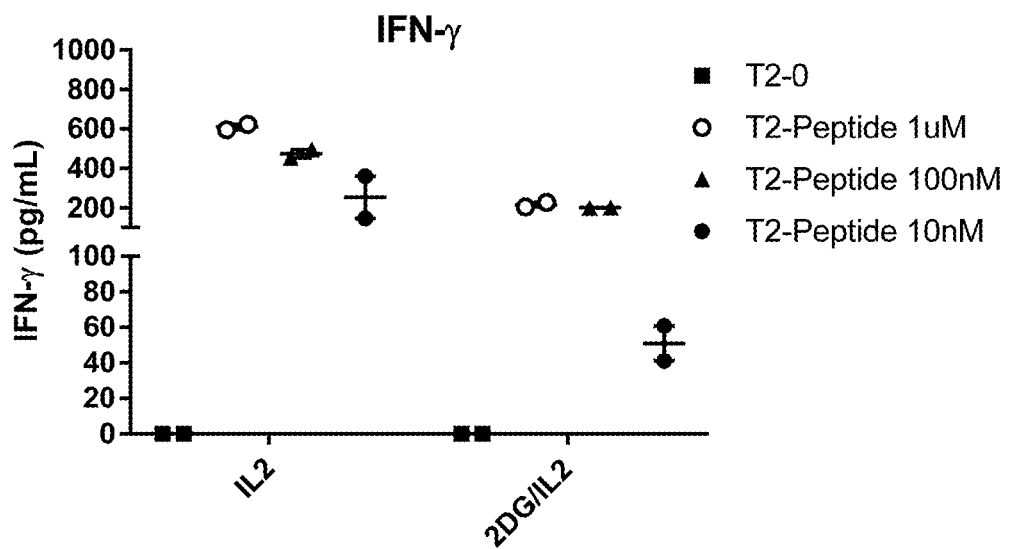
Figure 13C:
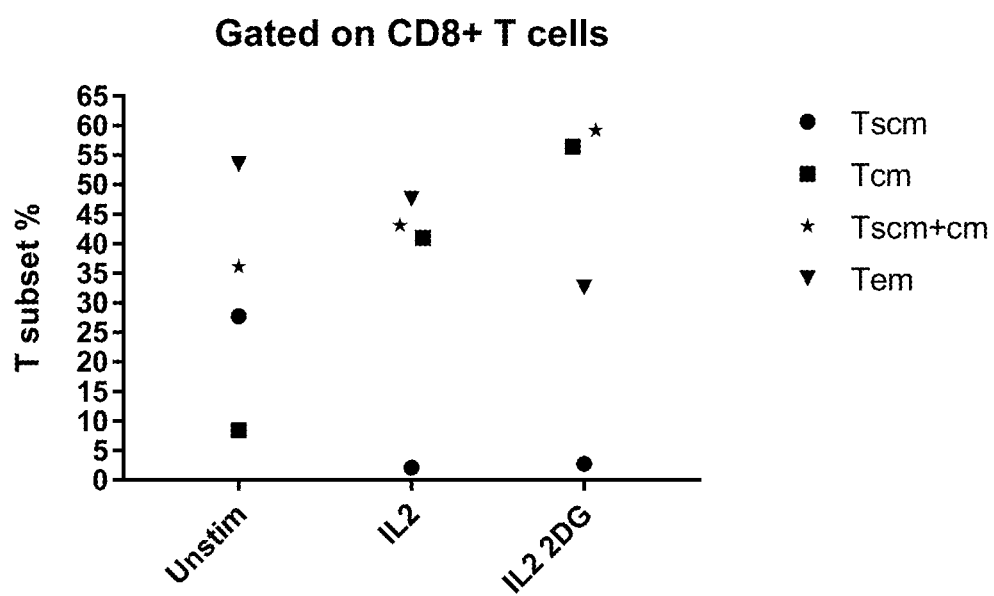

FIG. 13 shows the results from potency assays of engineered TCR T cells. T2 cells expressing Luciferase were pulsed with the peptide recognized by the engineered TCR or with DMSO for 4 hours and the cells were washed before setting up a co-culture assay with 20,000 total T cells at a 1:1 (E:T) ratio. (A) 48 hours later, the luciferase signal was measured using the Steady Glo® Luciferase Assay System (Promega). Specific cytotoxicity was measured relative to the no peptide T2 cells cultured with the TCR T cells. (B) IFN-γ expression was measured using the AlphaLISA® detection kit (Perkin Elmer Waltham, MA) after 24 hours of co-culture. No significant difference in T2 cell lysis was found between T cells in either 2-DG media or non-2-DG media at high peptide concentration (1 μM) and slightly higher T2 cell lysis was found for T cells at non-2-DG media than at lower peptide concentration (10 nM). In addition, 24 hour accumulated release of IFN-γ was higher for T cells in non-2-DG media cross all concentration of peptide tested. The lower level of IFN-γ for T cells in 2-DG media at early timepoint (24 hours) might be due to lag. Further data (not shown here) suggested that activation in T cells from 2-DG media had a more prolonged activation than in T cells from non-2-DG media, which could not be captured in a short-term IFN-γ assay. (C) shows differentiation of T cells under different media conditions. Culture media containing 2-DG was used throughout the entire process (10 days). T cells from the 2-DG media were less differentiated as suggested by the higher percentage of collected Tscm and Tcm subsets compared to the T cells from the non-2-DG media (59% vs 43%). This data suggests supplementing 2-DG in culture media for the entire process until harvest.

Example 3 This Experiment Compared CAR and TCR Transduction of Cells From an Apheresed Cell Sample From a Donor (Unenriched) With Cells From the Same Apheresed Cell Sample That Was Further Enriched for T Cells (Enriched)

On day 0, a fresh LEUKOPACK® (Hemacare, Northridge, CA), containing 300 ml fresh enriched leukapheresis product collected from normal peripheral blood was sterile welded to a CD-600.1 Sepax Cell Separation Kit (GE) and processed under the Culture Wash-Pro program. The LEUKOPACK® contained leukocytes, erythrocytes, and platelets. The cells were washed to remove plasma and apheresis buffers as described above in Example 1 and the nucleated cells were counted using NC200™ Automated Cell Counter and split equally into two transfer bags (Sample 1, Enriched T cells) and (Sample 2, Unenriched apheresed donor cells) using the Sepax C-Pro cell processing system Dilute program.

For Sample 1, "Enriched T cells", the T cells were isolated from the washed apheresed cells using an Easy Sep™ Human pan T negative selection kit (Stemcell Technologies) according to the manufacturer's instructions. The enriched T cells were added to a gas permeable bag at cell density 4E6 nucleated cells/ml in 120 ml OpTmizer™ complete media containing 300 IU IL-2. The gas permeable bag was previously coated with 1.23 g/ml anti-CD3 antibody (Miltenyi Biotec) in PBS. Soluble anti-CD28 antibody (Miltenyi Biotec) was added to the permeable bag at 1:100 (1μ/ml) dilution afterward for activation.

For Sample 2, "Unenriched apheresed donor cells", same cell density (4E6 nucleated cells/ml) was added into 120 ml OpTmizer™ complete media (containing 300IU/ml IL-2) into a gas permeable bag that was previously coated with anti-CD3 antibody as for Sample 1. Soluble anti-CD28 antibody (Miltenyi Biotec) was added to the permeable bag at 1:100 (1μ/ml) dilution afterward for activation.

Day 1 The nucleated cells in each gas permeable bag were counted and the amount of lentiviral vector comprising a polynucleotide encoding a TCR corresponding to a MOI of 1 (TCR) functional titer was added to one bag, a lentiviral vector comprising a polynucleotide encoding a CAR corresponding to a MOI of 40 (CAR) functional titer was added directly to a second bag, and a lentiviral vector comprising a polynucleotide encoding green fluorescent protein (GFP) was added to the third gas permeable bag. The bags were incubated at 37° C., 5% $CO_2$, overnight.

Days 2-6: On Day 2, an additional 120 ml OpTmizer™ complete medium containing 300 IU/ml IL-2 was added into each gas permeable bag to dilute the lentivirus.

Cells from each gas permeable were split into two bags on day 4, and on Day 6 were the bags were inoculated into equilibrated XURI® SP Perf bioreactor bags on XURI® W25 bioreactors (as described in Example 1), reaching a total volume of 800 ml culture media. The bioreactors were rocked at a rate of 6 rpm and at a 6° angle, at 37° C., 5% $CO_2$, gas flow rate of 0.1 L/min the entire time of expansion.

Days 7-13 or 14: On Day 7, the volume of culture media in the bioreactors was scaled up to 1 L. The cells were kept in bioreactor until Day 13 or 14, when they were harvested. During expansion, OpTmizer™ Complete media containing 300 IU/ml IL-2 was perfused at a rate of 500 ml/day on Day 8, at a rate of 800 ml/day on Day 9, and at a rate of 1 L/day from Day 10 until the time of harvest. Cell counts, viable cell density, cell viability, and metabolites were measured each day.

The cells were harvested on Day 13 or 14. The bioreactor bags were sterile welded to a Sepax Pro using Culture Wash program and CT-600 Cell Processing kit (GE Healthcare). One wash cycle was performed using saline (Baxter) supplemented with 1% vol human serum albumin (HSA). The wash was performed at 380×g for 5 min.

Viability and harvest recovery were measured. The cells were concentrated and further formulated at a 1:1 ratio with HyClone™ Cryopreservation Media (GE Healthcare) supplemented with 5% human serum albumin and cryopreserved by freezing to 100° C. using a Via Freeze™ (GE Healthcare) and storing in liquid nitrogen.

Results

Using unenriched apheresed donor cells as starting material improved transduction efficiency as seen in the level of surface expression and genome integration compared with using enriched-T cells as starting material. In addition, unenriched-cells from apheresis promoted a less-differentiated T cell phenotype. Two out of the three donors tested showed a higher percentage of Tscm and Tcm upon harvest in both $CD4^+$ and $CD8^+$ T cell subsets. T cell purity was comparable between using enriched- vs unenriched-T cells as starting material.

Figure 14A:
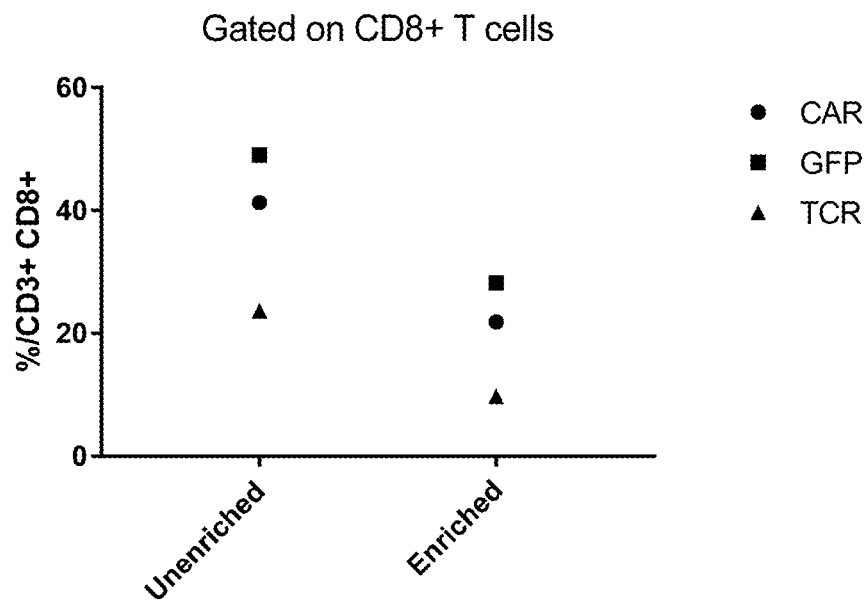
FIG. 14. Transgene expression of T cells at harvest from enriched- and unenriched-process, gated on CD8+ cells (A) or CD4+ cells (B).
Figure 14B:
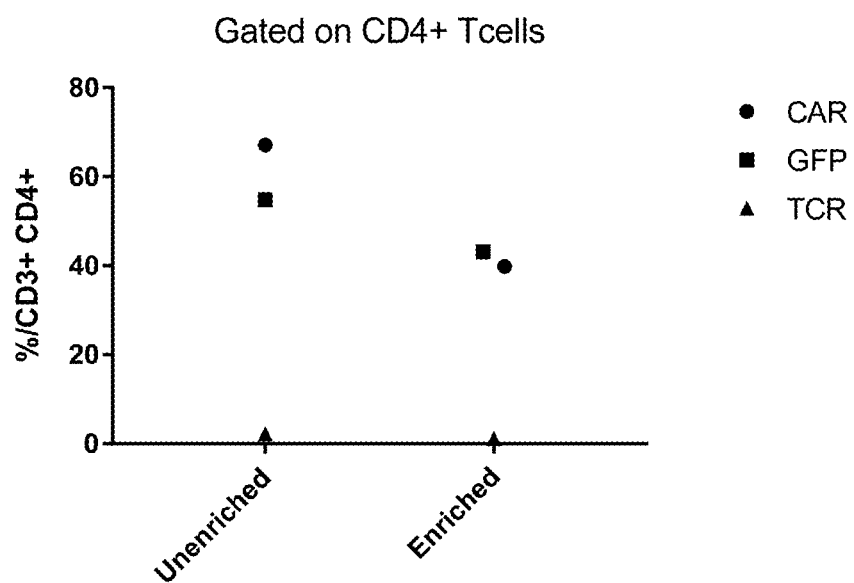

FIG. 14 shows transgene expression of T cells at harvest from enriched- and unenriched-cells. Three different lentiviral vectors delivering a CAR, a TCR, or a GFP were transduced into the enriched- and unenriched-donor cells. Transgene expression was detected via antibody staining for the CAR, dextramer staining for the TCR, and fluorescent signal for GFP, using flow cytometry. CAR, TCR, and GFP were higher in CD8 T cells from unenriched cells than from $CD8^+$ T cells from enriched process (A). Dextramer staining was CD8 receptor dependent, thus CD4 T cells did not show expression of TCR (B). However, CAR and GFP expression were both higher in $CD4^+$ T cells from unenriched donor cells compared to the enriched donor cells (B).

Figure 15:
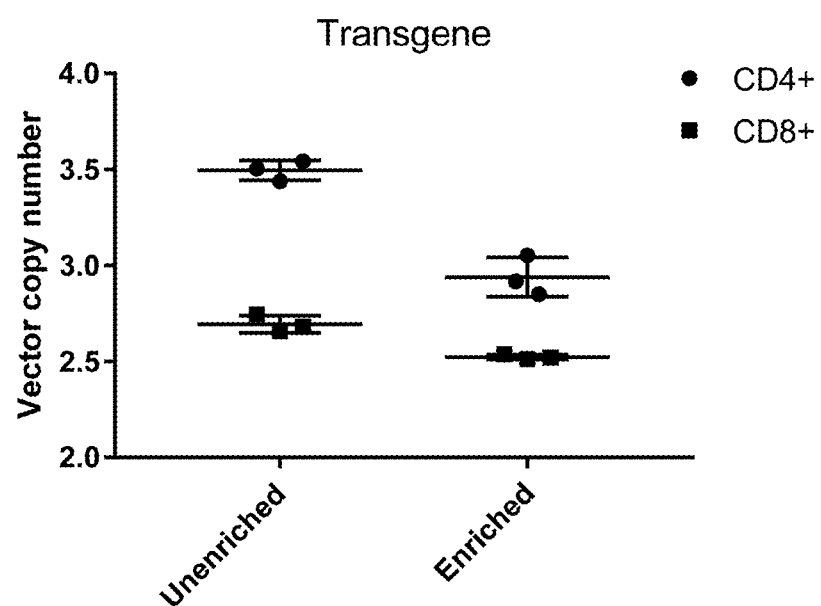
FIG. 15. Vector copy number of TCR in CD4+ and CD8+ T cells.

FIG. 15 shows the vector copy number of TCR in $CD4^+$ and $CD8^+$ T cells. Copies of WPRE and human albumin were measured via qPCR and vector copy number of the TCR was calculated as a ratio of WPRE and human albumin divided by two. Vector copy number of the TCR was higher in both $CD4^+$ T cells and $CD8^+$ T cells from unenriched donor cells than in the enriched donor cells. It is found that the transgene integration was also higher in T cells from apheresis than in enriched T cells, indicated by higher vector copy number.

Figure 16:
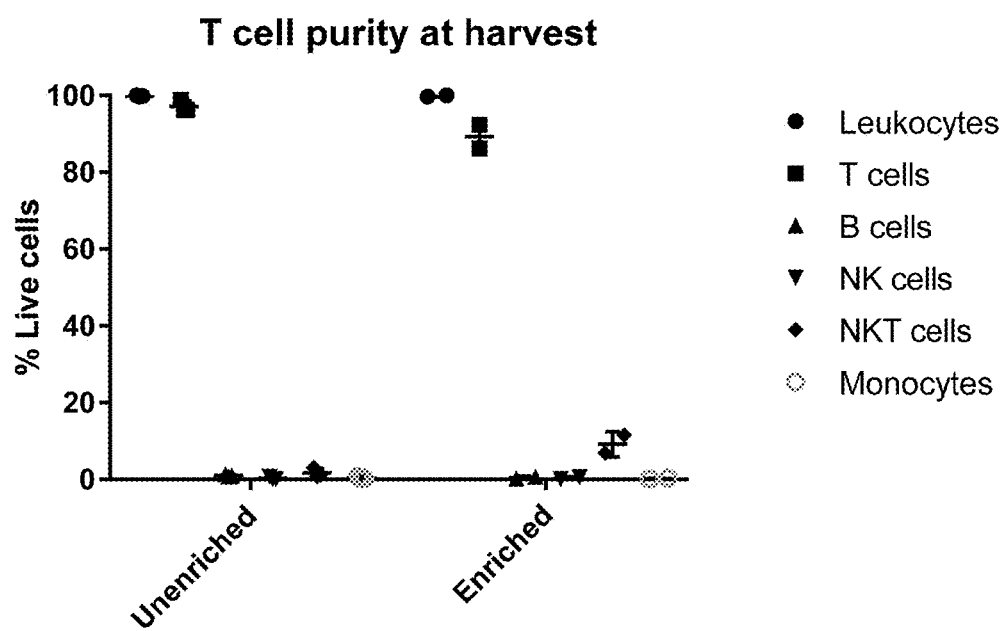
FIG. 16. Percentage of leukocytes and leukocyte subsets measured at the end of harvest.

FIG. 16 shows the percentage of leukocytes and leukocyte subsets measured at the end of harvest. All cells were stained for leukocytes (CD45+). Minimal (<1%) B cells (CD19+), NK cells (CD56/16+), and monocytes (CD14+) were detected in both unenriched and enriched donor cells. Overall the percentage of $CD3^+$ cells (>99%) was comparable between the unenriched and enriched donor cells with the percentage of T cells (CD3+CD56−) slightly lower in the enriched donor cells due to expansion of NKT cells (CD3+CD56+).

Figure 17:
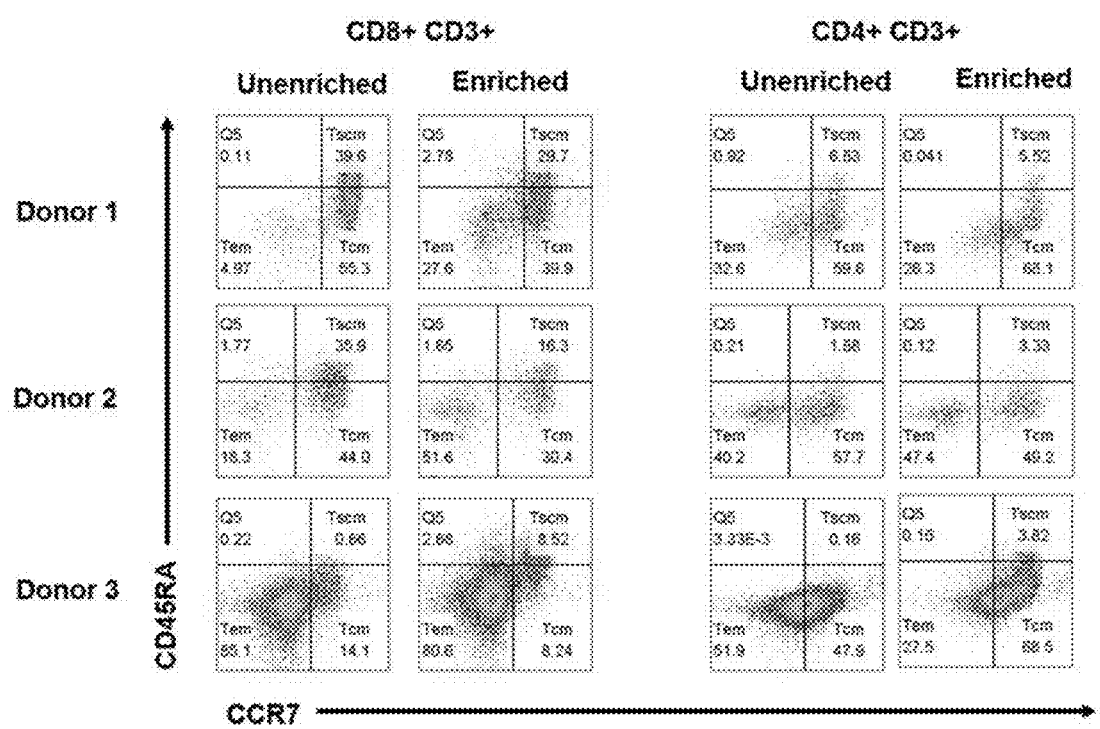
FIG. 17. T cell phenotype at harvest from the enriched- and unenriched-cells from three donors.

FIG. 17 shows the T cell phenotype at harvest from the enriched- and unenriched-donor cells. This experiment was repeated three times with a different donor samples each time. Among the three donor samples tested, harvested T cells from two donors expressed higher percentage of memory stem cell markers (CD45RA+, CCR7+) and central memory markers (CD45RA−, CCR7+) from unenriched donor cells compared to those cells subject to T cell enrichment. This difference was only significant in $CD8^+$ T cells but not in $CD4^+$ T cells.

Figure 18A:
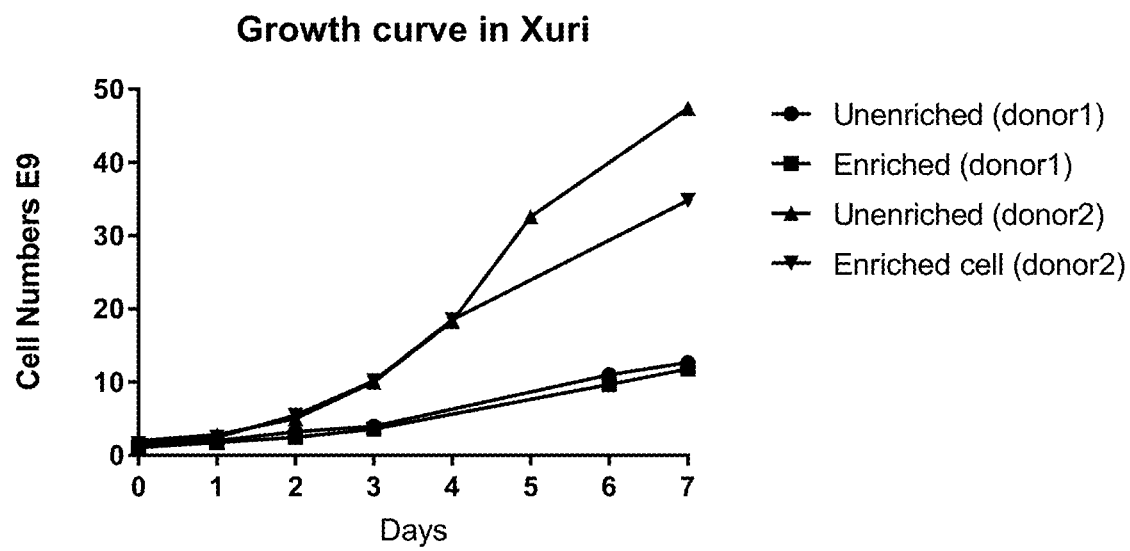
FIG. 18. Growth curve (A) and viability (B) of cells in the bioreactor from enriched- and unenriched-donor cells.
Figure 18B:
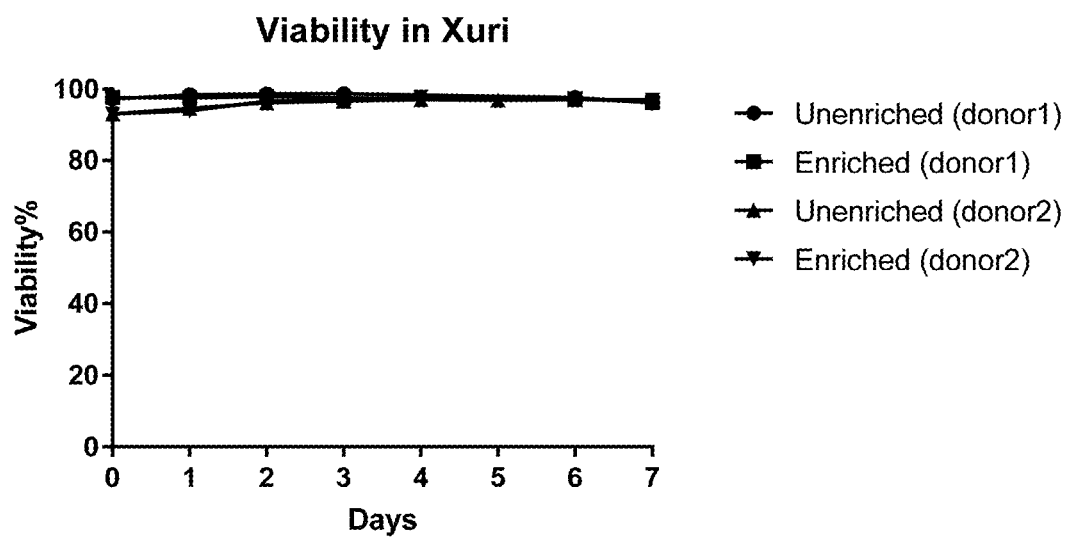

FIG. 18 shows the growth curve and viability of cells in the bioreactor from enriched- and unenriched-donor cells. Growth (A) and viability (B) were comparable between the enriched- and unenriched-donor cells.

Example 4 this Example Provides a Closed Continuous Method for Producing Genetically Engineered Autologous T Cells that Express a T Cell Receptor On day 0, a fresh LEUKOPACK® (Hemacare, Northridge, CA), containing 300 ml fresh enriched leukapheresis product collected from normal peripheral blood was sterile welded to a CD-600.1 Sepax Cell Separation Kit (GE) and processed under Culture Wash-Pro program. The LEUKOPACK® contained leukocytes, erythrocytes, and platelets. The cells were washed in 1 L ClinMACS® PBS/EDTA, 5 ml human serum albumin (Miltenyi Biotec, San Diego, CA) to remove plasma and apheresis buffers using a Sepax CPro equipped with a CS-600.1 Kit (GE Healthcare) according to manufacturer's instructions. Based on the initial white blood cell (WBC) count indicated on the donor information sheet accompanying the LEUKOPACK®, the cells were eluted at a cell density of 150E6 WBC/ml with ~50 ml OpTmizer™ complete media.

The nucleated cells in the washed leukapheresed harvest sample were counted using NC200™ Automated Cell Counter and followed by determining total viable cell count, viability, and immunophenotype of the washed cells.

A sample of the washed apheresed donor cells comprising 1.2E9 nucleated cells was then transferred into a transfer bag (Charter Medicine) under the Dilute program using the Sepax C-Pro processing system with the same CD-600.1 Kit in ~6.5 ml OpTmizer™ complete media containing 300 ml IL-2 and was incubated with 7.5 ml ImmunoCult™ Human CD3/CD28/CD2 (2.5 µg/ml, Stemcell Technologies) at room temperature for 1 hour at room temperature to allow saturation of antibody binding.

A 2 L XURI® SP Perf Cellbag bioreactor (GE Healthcare) was connected to a XURI® Cell Expansion System W25 and 300 ml OpTmizer™ complete media containing 300 IU IL-2 was added and allowed to equilibrate at 37° C., 5% $CO_2$, gas flow rate of 0.1 L/min, and a rocking rate of 6 rpm at a 6° angle.

The transfer bag was sterile welded to the XURI® Cellbag feed-line and the contents transferred into the bag by gravity. The cells were then incubated overnight at 37° C., 5% $CO_2$, gas flow rate 0.1 L/min at a rocking rate of 2 rpm at a 2° angle, to facilitate activation.

On Day 1, the nucleated cells in the bag were counted. An amount of a lentiviral vector (comprising a polynucleotide encoding a TCR) that corresponded to a MOI of 1 functional titer was diluted in 10 ml of OpTmizer™ complete media containing 300 IU/ml IL-2 and was placed in a transfer bag. The transfer bag was sterile welded on to the XURI® Cellbag feed-line and lentiviral vector was transferred into the bioreactor via gravity. The cells were incubated at 37° C., 5% $CO_2$, gas flow rate of 0.1 L/min, and a rocking rate of 2 rpm at a 2° angle, for 20-24 hours.

On Day 2, about half the volume of the culture media in the bioreactor bag was exchanged for fresh OpTmizer™ complete media including 300 IU/ml IL-2 using three 50 ml washouts. Cell counts were taken daily and viable cell density (VCD) and viability were determined using NC200, dissolved oxygen, metabolites were also measured. Cell phenotypes were determined for all samples tested. The bags were maintained on the rocking bioreactors at 2 rpm at a 2° angle, 37° C., 5% $CO_2$, gas flow rate of 0.1 L/min, for 24 hours.

On Days 3-10 the culture was maintained at 300 ml OpTimzer complete media including 300 IU/ml IL-2 by perfusion feeding at rate of one bag volume per day, with a rocking rate of 2 rpm at a 2° angle, at 37° C., 5% $CO_2$, with gas flow rate of 0.1 L/min, until the cell density reached 4e6 cells/ml.

At that point, the volume of the culture media was increased to 600 ml, perfusing at a rate of one bioreactor bag per day, with a rocking rate of 4 rpm at a 4° angle, at 37° C., 5% $CO_2$, with gas flow rate of 0.1 L/min, until the cell density again reached 4e6 cells/ml.

At that point the volume of the culture media was increased to 1000 ml, perfusing at a rate of one bioreactor bag per day, with a rocking rate of 6 rpm at a 6° angle, at 37° C., 5% $CO_2$, with gas flow rate of 0.1 L/min, until harvest on Day 10.

Total viable cell density, viability, glucose and lactate measurements were taken each day. Phenotyping was determined on days 3, 5 and 7.

The cells were harvested on Day 10. The XURI® SP Per bioreactor bag was sterile welded to a Selfia 5200 Cell Processing System using the FlexCell program and CT-800.1 Cell Processing kit (GE Healthcare,). The T cell were concentrated to ~20 ml at a 75 ml/min flow rate. One wash cycle was performed using 0.9% saline (Baxter, Deerfield, Ill) supplemented with 1% vol human serum albumin (HSA). The wash was performed at 380×g for 5 min. The wash was performed at 380×g for 5 min.

The cells were then eluted at 2e8 cells/ml in saline supplemented with 1% HSA and were further formulated at a 1:1 ratio with HyClone™ Cryopreservation Media (GE Healthcare) supplemented with 5% human serum albumin. Final cell product was then split into two freezing bags and several cryovials, which were finally frozen down in VIA Freeze™ Quad freezer (GE) with a cooling rate of −1° C./min until the temperature reached −80° C. After freezing, cells were transferred to liquid nitrogen for long-term storage.

Results

Figure 19:
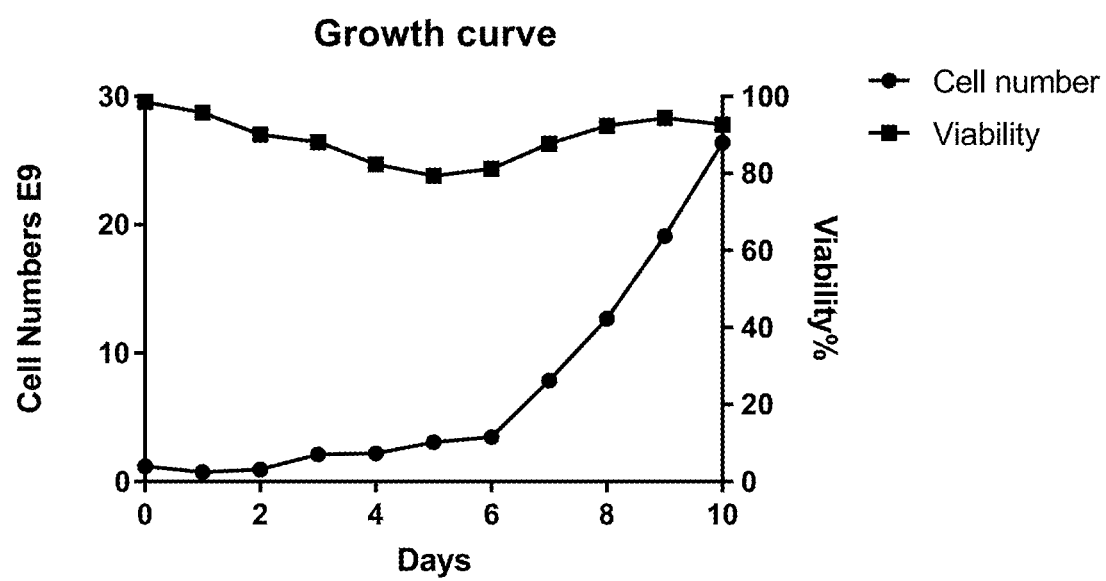
FIG. 19. Growth curve and viability of cells.

FIG. 19 shows the growth curve and viability of cells. The dip in viability is likely due to gradual die off of non-T cells.

Figure 20:
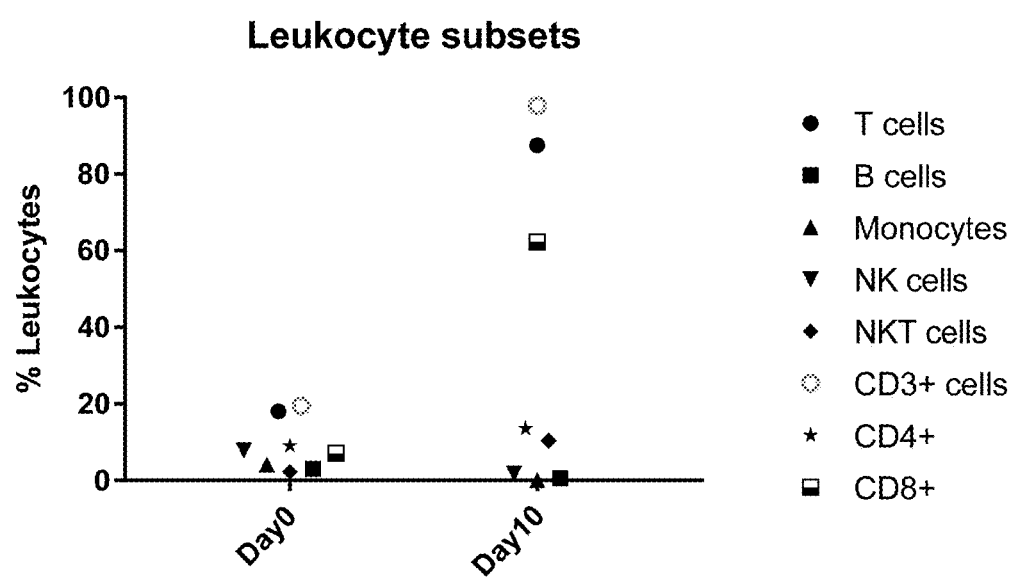
FIG. 20. Percentage of leukocyte subsets at Day 0 and Day 10.

FIG. 20 shows the percentage of leukocyte subsets at Day 0 and Day 10. The cells were stained with an antibody cocktail targeting B cells (CD19), Monocytes (CD14), T cells (CD3+, CD56/16−), NKT cells (CD3+, CD56/16+), NK cells (CD3−, CD56+), CD4 T cells (CD3+, CD4+), and CD8 T cells (CD3+, CD8+) and analyzed by flow cytometry. CD3 cell purity reached 98% with total T cells at 98% and NKT cells at 10% by the time of harvest (10 days).

Figure 21:
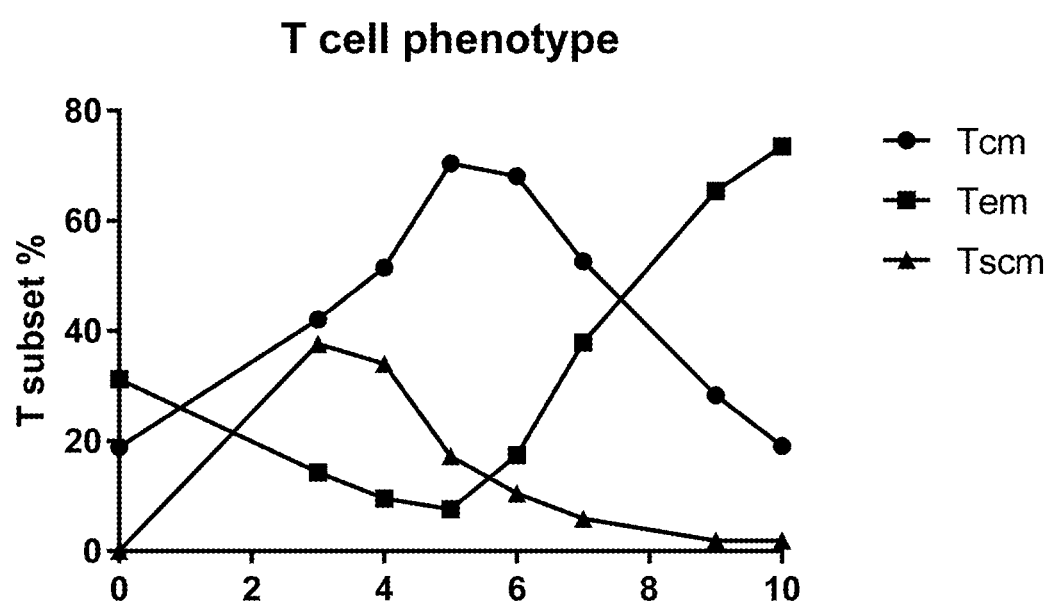
FIG. 21. T cell differentiation during bioprocessing.

FIG. 21 shows T cell differentiation during bioprocessing. T cells subsets Tscm (CD45RA+, CD45RO−, CCR7+, CD95+), Tcm (CD45RA−, CD45RO+, CCR7+, CD95+), and Tem (CD45RA−, CD45RO+, CCR7−, CD95+) were stained with antibody cocktail and analyzed by flow cytometry at different timepoints. T cells differentiated similarly to that shown in in Examples 1 and 2 with around 70% Tem and around 30% Tscm+Tcm by the time of harvest.

Figure 22A:
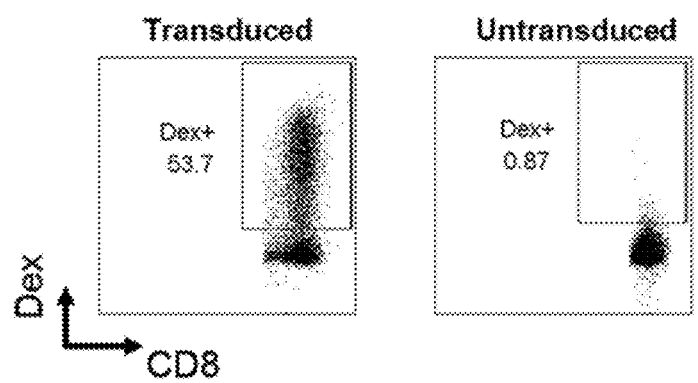
FIG. 22 shows the expression of transgene in harvested T cells at cell surface level (A) and DNA level (B).
Figure 22B:
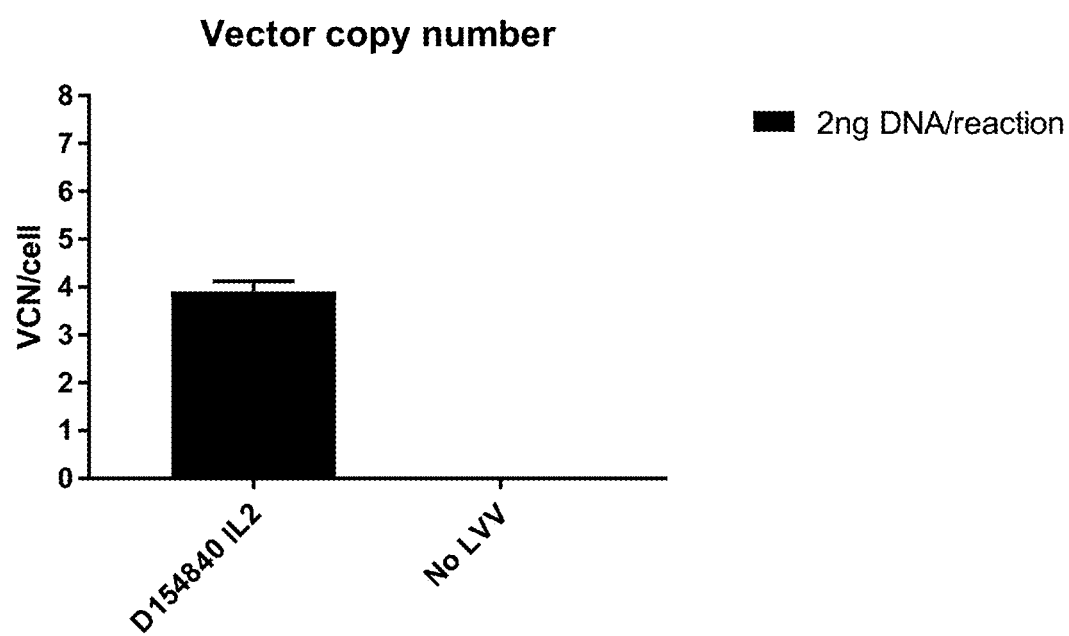

FIG. 22 shows the expression of transgene in harvested T cells at cell surface level (A) and DNA level (B). Dextramer staining was performed to qualify surface expression of transgene on transduced and untransduced T cells. Transgene expression was over 50% on transduced T cells (A). DNA was extracted from harvested cells and 2 ng DNA was used for qPCR reactions targeting WPRE and human albumin. Vector copy number was calculated as a ratio of copy number of WPRE and copy number of human albumins divided by 2. No detectable copy of transgene was found in untransduced T cells and copy number of transgene in transduced T cells was under 5, within the guideline on vector copy number implemented by FDA (B).

Figure 23:
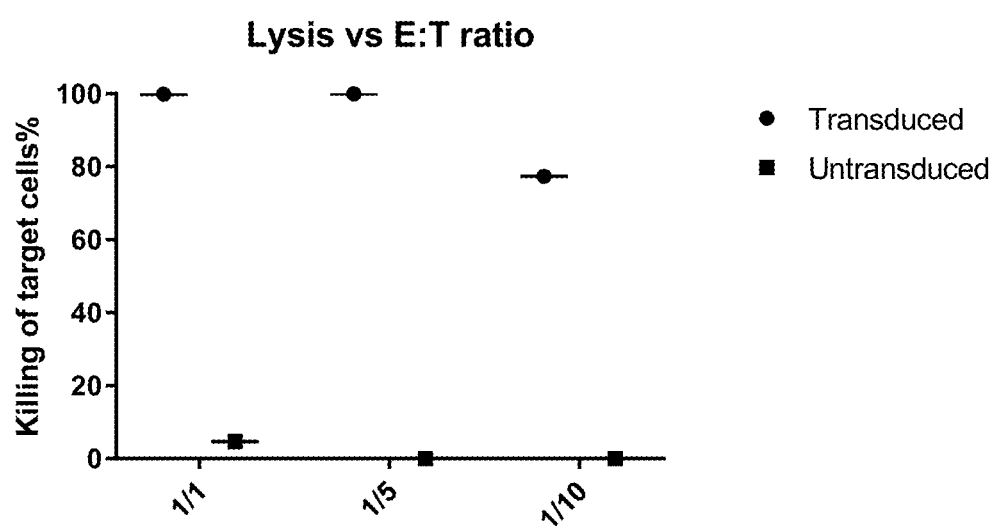
FIG. 23. Percentage of killing of target cells at different effector to target cells (E: T) ratios.

FIG. 23 shows the percentage of killing of target cells at different effector to target cells (E:T) ratios. Harvested T cells (transduced or un-transduced) were co-cultured with target cells for 24 hours at E:T ratio at 1:1, 1:5, and 1:10. Percentage of killing of target cells was calculated by the percentage of cell death of target cells after 24 hours of co-culture. Transduced T cells showed strong killing of target cells (>70%) at all E:T ratio tested.

Figure 24:
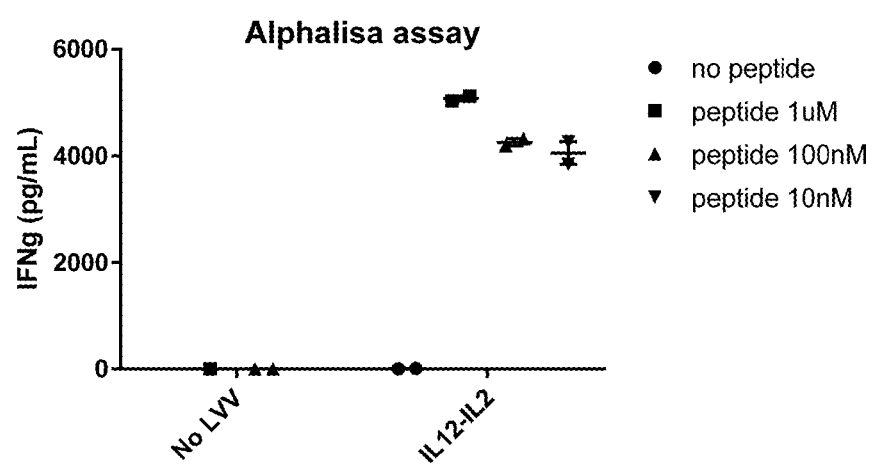
FIG. 24. IFN-gamma release of harvested cells in response to target cells.

FIG. 24 shows IFN-gamma release of harvested cells. Harvested cells (transduced and untransduced) were co-cultured with target cells pulsed with different concentrations of peptide for 24 hours. IFN-gamma in the supernatant was measured via AlphaLISA® assay. Similar level of IFN-gamma was seen in Example 1 and 2.

The closed continuous autologous process generated over 26 billion engineered T cells rapidly (10 days), with high transgene expression (>50%) and CD3 cell purity (98%). The engineered T cells exhibited remarkable killing potency against target cells at low effector to target cells ratio (1:10) possibly resulting from robust IFN-gamma release in response to target cells.

Example 5 Assessing Transduction Efficiency of a T Cell Expressing a TCR after Stimulation with Different Reagents On day 0, half of a fresh LEUKOPACK® (Hemacare, Northridge, CA), containing 150 ml leukapheresis product collected from normal peripheral blood was sterile welded to a CD-600.1 Sepax Cell Separation Kit (GE) and processed under Culture Wash-Pro program. The LEUKOPACK® contained leukocytes, erythrocytes, and platelets. The cells were washed in 1 L ClinMACS® PBS/EDTA, 5 ml human serum albumin (Miltenyi Biotec, San Diego, CA) to remove plasma and apheresis buffers using a Sepax C-Pro Cell Separation System equipped with a CS-600.1 Kit (GE Healthcare), according to manufacturer's instructions.

The nucleated cells in the harvest sample were counted using NC-200™ Automated Cell Counter (ChemoMetec) and followed by determining total viable cell count, viability, and immunophenotype of the washed cells.

Starting populations of cells were prepared either by isolating pan T cells from the washed cells donor cells using an EasySep™ Human pan T negative selection kit (Stemcell Technologies) according to the manufacturer's instructions or using the washed donor cells without further selection or enrichment, "unenriched cells". The enriched pan T cells and the unenriched cells were resuspended in OpTmizer™ complete media containing 300 IU/ml IL-2 (Stemcell Technologies), unless otherwise noted, and added to transfer bags. In some experiments IL-7, IL-15, IL-21, and/or TWS1119 (Stemcell Technologies) were used in the activation and expansion media.

Gas-permeable bags (PL07, Permalife, OriGen, Austin, TX) were prepared by coating with 1 µg/mL anti-CD3 (Clone OKT3 Miltenyi Biotech, Cambridge, MA) in PBS at 4° overnight and washed with PBS before adding cells. The following conditions were tested:

1) In one experiment, isolated pan T cells ($2\times10^6$ cells/mL) were inoculated into anti-CD3 coated bags in OpTmizer™ complete media containing 300 IU/ml IL-2 (Stemcell Technologies) and 1 µg/ml anti-CD28 (Miltenyi). For the titration of anti-CD3 or starting cell number, anti-CD3-coated plates (Corning) were used. The plates were coated with anti-CD3 at a titrated concentration from 0.0001-10 µg/ml. The cells were activated for 20 hours and 48 hours. These cells were not transduced. The levels of CD69, CD25, and 4-1BB on CD3+ T cells was measured by flow cytometry at 20 and 48 hours (2 replicates per condition).

2) To compare the different activators, isolated pan T cells ($2\times10^6$ cells/mL) were inoculated into anti-CD3 coated bag in OpTmizer™ complete media containing 300 IU/ml IL-2 (Stemcell Technologies) and 1 ug/ml anti-CD28 (Miltenyi). The following soluble activators were tested against the coated anti-CD3 condition: Immunocult™ anti-CD3/CD28 (Stemcell Technologies, Cambridge, MA), and Immunocult™ anti-CD3/CD28/CD2 (Stemcell Technologies), each at 25 uL activator per 1 mL of medium at 2E6 cells/mL, following the manufacturer's instructions. Dynabeads™ Human T-Activator CD3/CD28 (ThermoFisher) at a 1:1 beads:cells ratio, following manufacturer's instructions, was tested in an uncoated bag. The cells/activators were incubated for 20 hours and 48 hours.

3) Isolated pan T cells ($2\times10^6$ cells/mL) were inoculated into anti-CD3 coated gas-permeable bags from above, in OpTmizer™ complete media containing 300 IU/ml IL-2 (Stemcell Technologies) and 1 ug/ml anti-CD28 (Miltenyi). The following activators were tested: 1 ug/mL coated anti-CD3 gas permeable bags from above with 1 ug/mL. Soluble anti-CD28 (Miltenyi), soluble Immunocult™ anti-CD3/CD28/CD2 (Stemcell Technologies), at 25 uL activator per 1 mL of medium, Dynabeads™ Human T-Activator CD3/CD28 (ThermoFisher) at a 1:1 beads:cells ratio, and soluble MACS® GMP T Cell TransAct™ anti-CD3 and anti-CD28 conjugated polymeric nanomatrix, (Miltenyi Biotech) at a concentration of (1:17.5 dilution), were tested in uncoated bags 48 hours after activation, the cells from the coated anti-CD3 bag were transferred to a new bag to remove the stimulation. Following activation, the cells were transduced, as described below. The cells/activators were incubated for 7 days. Engineered TCR expression was assessed by flow cytometry using a dextramer recognizing the peptide-MHC class I complex, gated on CD8+ T cells.

4) Washed leukapheresed cells ($2\times10^6$ cells/mL) were inoculated into the anti-CD3 coated gas-permeable bags from above in OpTmizer™ complete media containing 300 IU/ml IL-2 (Stemcell Technologies) and 1 ug/ml anti-CD28 (Miltenyi). The following activators were tested: 1 ug/mL coated anti-CD3 (Miltenyi) with 1 ug/mL soluble anti-CD28 (Miltenyi) and soluble Immunocult™ anti-CD3/CD28/CD2 (Stemcell Technologies), at 25 uL activator per 1 mL of medium. 48 hours after activation, the cells from the coated anti-CD3 bag were transferred to a new bag to remove the stimulation. Following activation, the cells were transduced, as described below. The cells/activators were incubated for 7 days. Transduction efficiency was assessed by flow cytometry using GFP expression, gating on either CD8+ or CD4+ T cells.

5) The effect of different cytokine cocktails. Fresh cells from the Leukopheresed material (WLPCs) were activated at $2\times10^6$ cells/mL in gas permeable bags with Immunocult™ anti-CD3/CD28/CD2 (Stemcell Technologies) in OpTmizer™ complete media containing 4 different cytokine cocktails: a) 300 IU/ml IL-2, b) 10 ng/mL IL-7 (Stemcell Technologies) and 10 ng/mL IL-15 (Stemcell Technologies), c) 10 uM TWS119 (Stemcell Technologies), 10 ng/mL IL-7 (Stemcell Technologies), and 20 ng/mL IL-21 (Stemcell Technologies), or d) 10 ng/mL IL-7 (Stemcell Technologies) and 20 ng/mL IL-21 (Stemcell Technologies). Engineered TCR expression was assessed by flow cytometry using a dextramer specific to the TCR (Immudex), gating on CD8+ T cells.

6) The effect of starting WLPC density for activation with soluble activator. Cells were activated with Immunocult™ anti-CD3/CD28/CD2 (Stemcell Technologies) in OpTmizer™ complete media containing 300 IU/mL IL-2 or 10 uM TWS119 (Stemcell Technologies) 10 ng/mL, IL-7 (Stemcell Technologies), and 20 ng/mL IL-21 (Stemcell Technologies at 4 different densities: a) $1\times10^6$ cell/mL, b) $2\times10^6$ cell/mL, c) $4\times10^6$ cell/mL, or d) $6\times10^6$ cell/mL. Engineered TCR expression was assessed by flow cytometry using a dextramer specific to the TCR (Immudex), gating on CD8+ T cells.

When transduced, 24 hours following activation, the cells in each bag (from experiments 3, 4, 5, and 6 above) were counted. An amount of a lentivirus vector (comprising a polynucleotide encoding a TCR and GFP) that corresponded to a MOI of 1-2 functional titer was added to the bag and incubated overnight at 37° C., 5% $CO_2$.

The cells were expanded in static culture in the gas-permeable bags, keeping the cell density between 1-3 million cells/mL by splitting every 2-3 days and transferring to larger gas-permeable bags as needed. The expansion was done for 6-9 days. Media with cytokines were replaced every 2-3 days.

Cell counts were taken every 1-3 days.

Results

Figure 25:
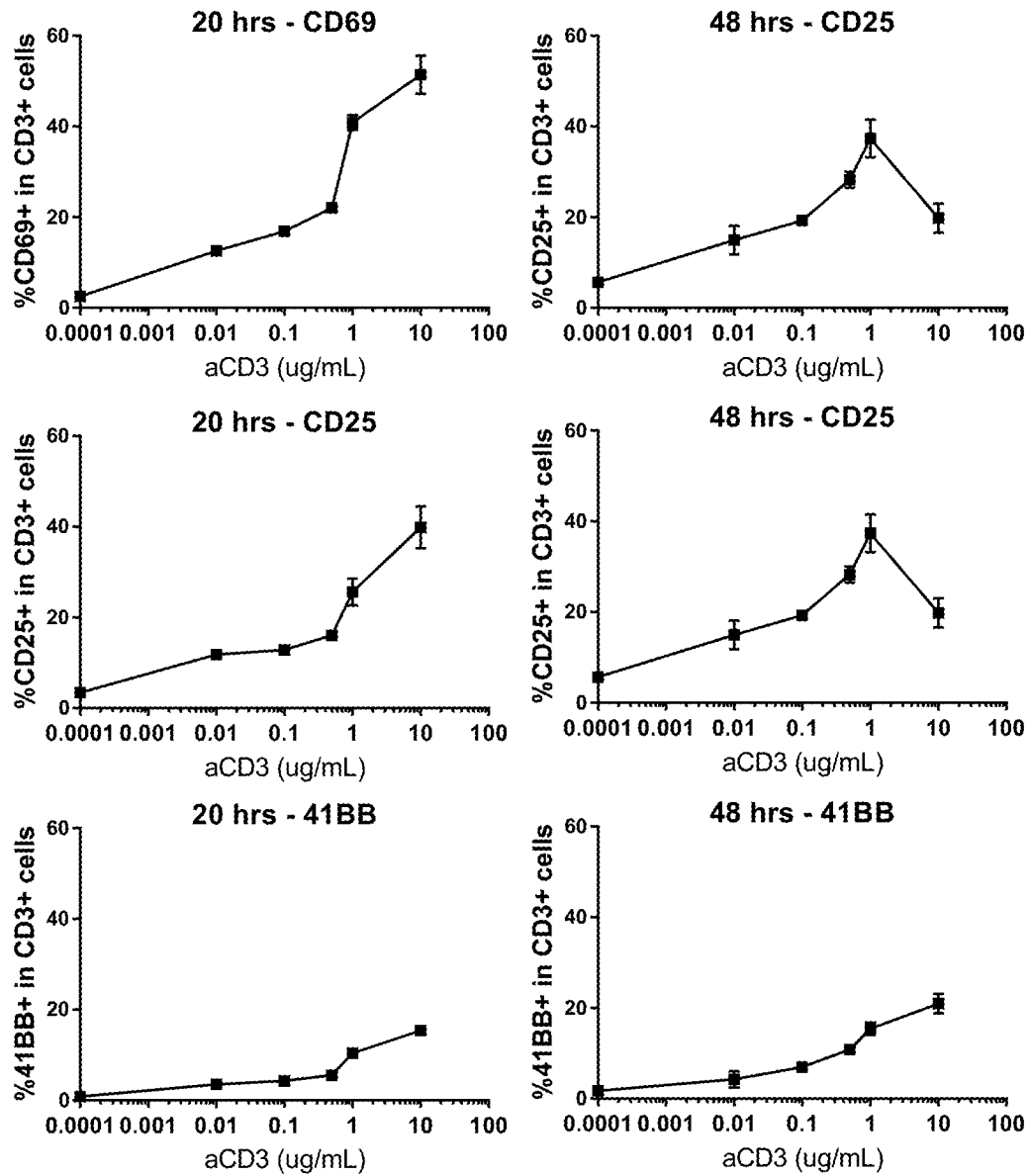
FIG. 25. Results of the titration of coated anti-CD3 (OKT3) antibody and pan T cell activation measured by CD69, CD35, and 4-1BB.

FIG. 25 shows the results of the titration of coated anti-CD3 (OKT3) antibody and pan T cell activation measured by CD69, CD25, and 4-1BB. Based on the stimulation of the T cells, 1 ug/ml anti-CD3 was chosen for comparison with the soluble activators.

Figure 26:
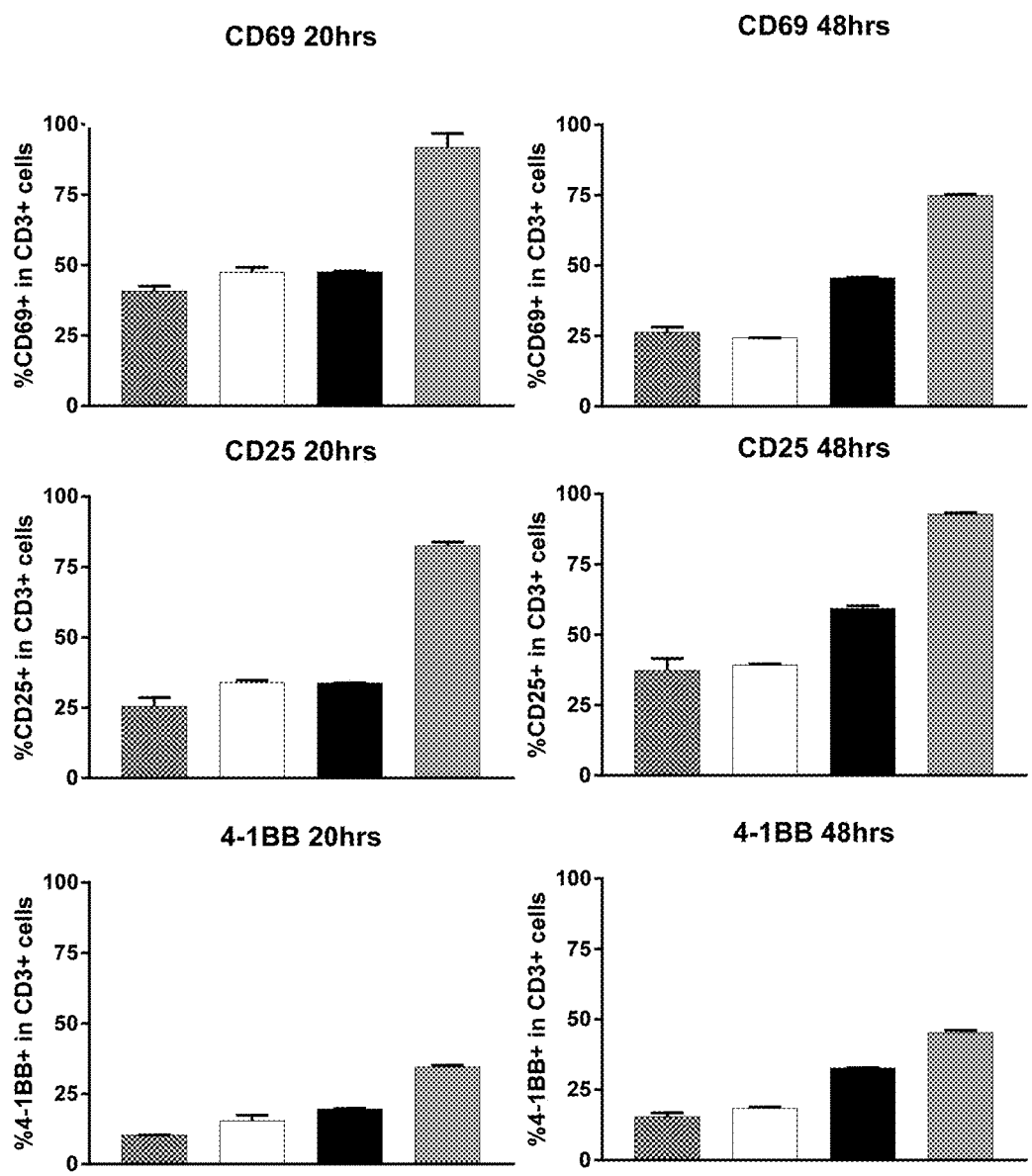
FIG. 26. Results of stimulation of pan T cells with various soluble activators versus coated anti-CD3 as measured by CD69, CD25, and 4-1BB.

FIG. 26 shows the results of stimulation of pan T cells with various soluble activators versus coated anti-CD3 as measured by CD69, CD25, and 4-1BB. Dynabeads™ (anti-CD3/CD28) showed the strongest stimulation, followed by the Immunocult™ anti-CD3/CD28/CD2 at the manufacturer's recommended concentration of 25 µL/mL of cells in media. Interestingly, the soluble Immunocult™ anti-CD3/CD28 activator was comparable to coated anti-CD3.

Figure 27A:
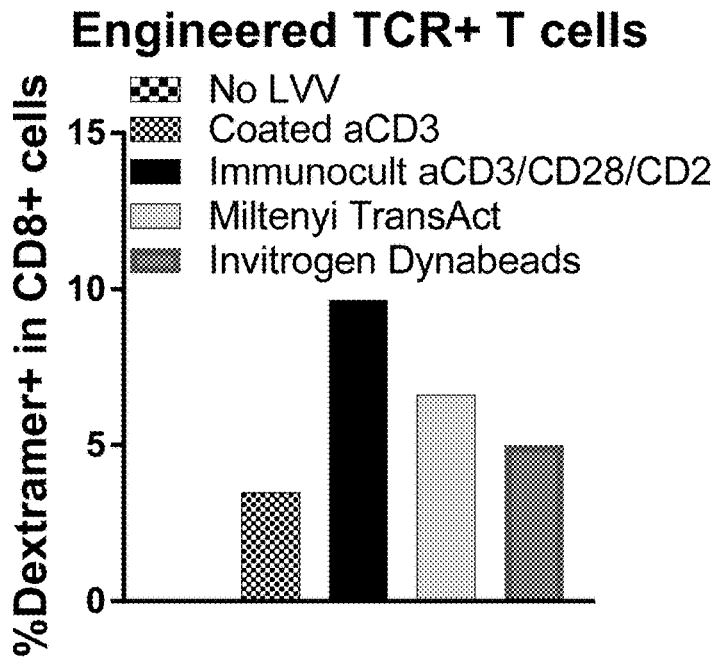
FIG. 27. Transduction efficiency for the engineered T cells, Pan T cells (A) and apheresed donor cells (B).
Figure 27B:
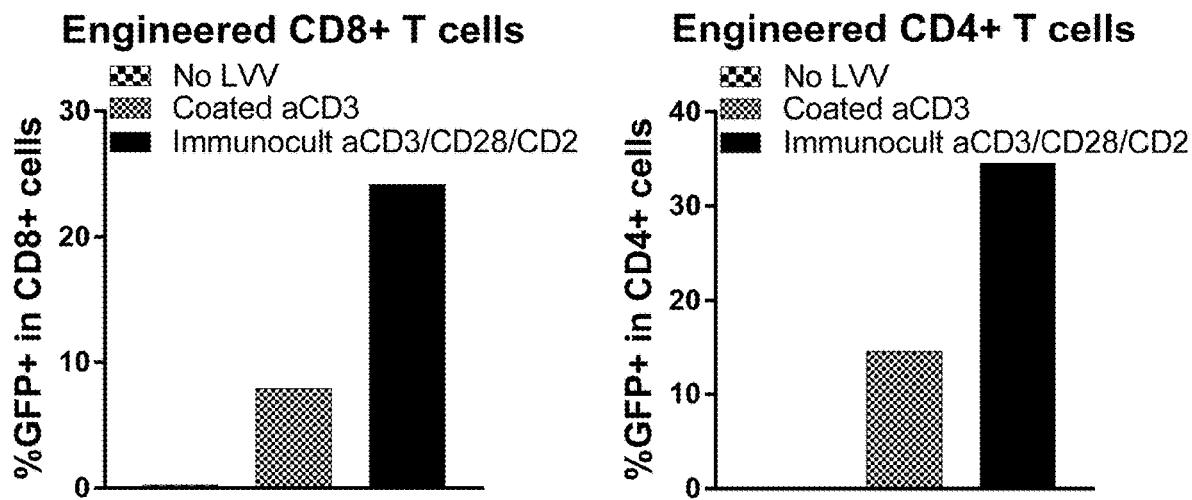

FIG. 27 shows the transduction efficiency of the engineered T cells was dependent on stimulation signal. (A) Starting material: pan T cells. Dextramer staining of the engineered TCR on CD8+ T cells showed Immunocult™ anti-CD3/CD28/CD2 gave the highest transduction efficiency. (B) Starting material: apheresed cells: FACS for GFP expression in transduced CD4+ and CD8+ T cells showed Immunocult™ anti-CD3/CD28/CD2 was superior to coated anti-CD3.

Figure 28:
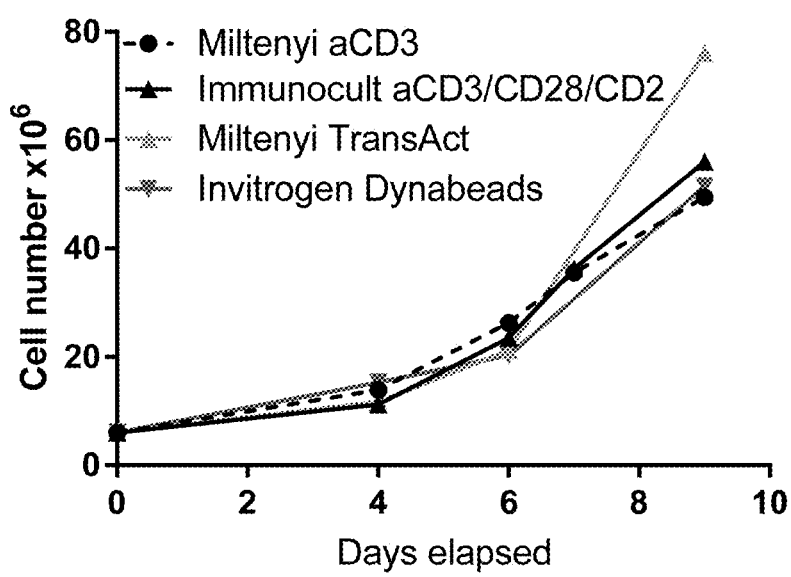
FIG. 28. Cell growth of cells activated by various activators.

FIG. 28 shows cell growth was similar between apheresed cells activated coated anti-CD3/soluble anti-CD28, Immunocult™ anti-CD3/CD28/CD2, TransAct™, and Dynabeads™ for 9 days.

Figure 29:
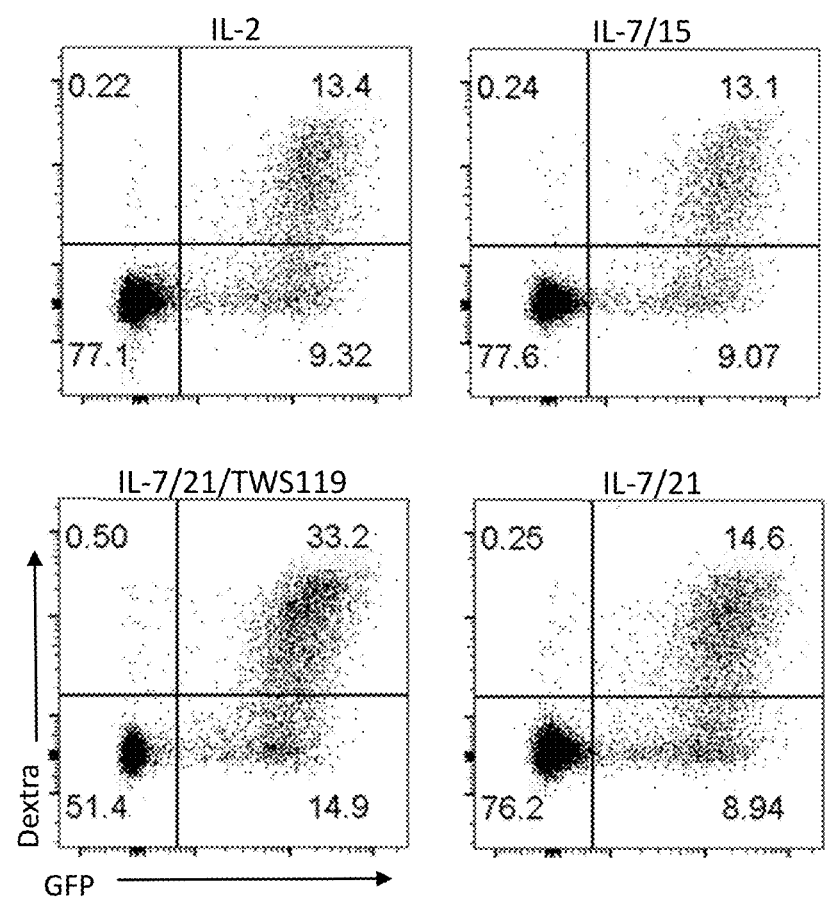
FIG. 29. Effect of culture conditions on transduction efficiency.

FIG. 29 shows culture conditions influenced the transduction efficiency of the engineered T cells. Apheresed cells grown in culture media containing IL-2, the combination of IL-7/15, of the combination of IL-7/21 were similar in transduction efficiency. The cocktail containing IL-7/21/TWS119 improved transduction efficiency.

Figure 30:
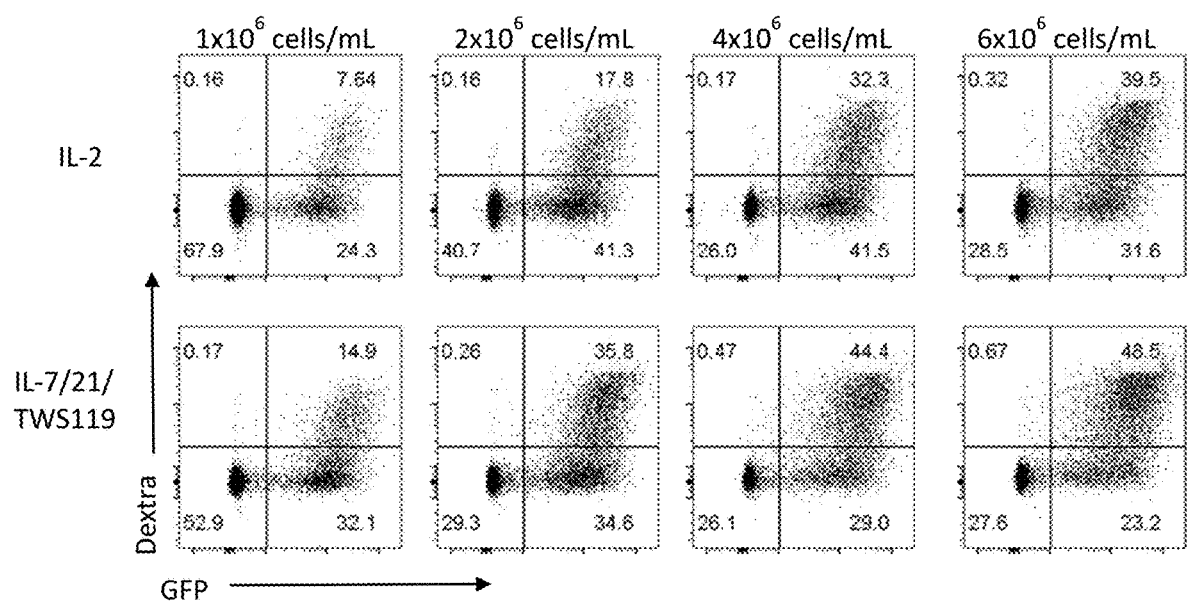
FIG. 30. Cell density and transduction efficiency.
Figure 31A:
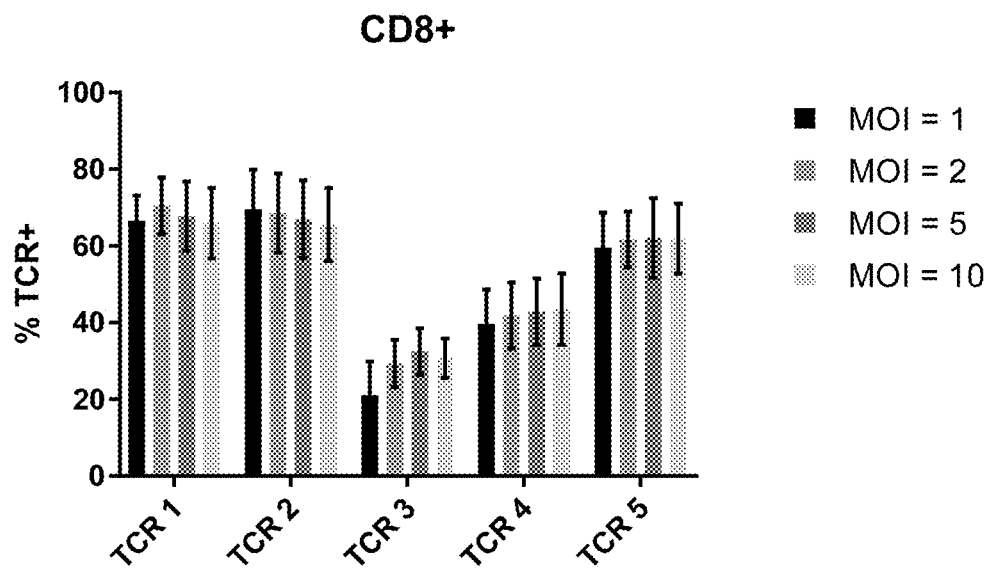
FIG. 31. Multiplicity of infection for TCR transduction. (A) MOI of 1-10, (B) MOI of 0.25 to 2.
Figure 31B:
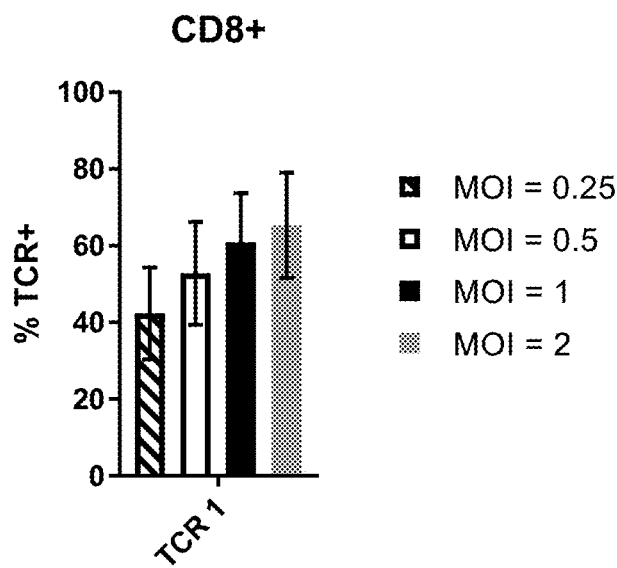

FIG. 30 shows starting cell density had an impact on transduction efficiency. Although there was no effect on the overall growth, higher starting densities of apheresed cells that were activated with Immunocult™ anti-CD3/CD28/CD2 yielded better transduction efficiencies when culture media contained either IL-2 or a cocktail of IL-7/21/TWS119.

This comparison of different T cell activators and cytokines using two different starting cell populations, enriched pan T cells and leukapheresed cells. Activation strength did not appear to correlate with better transduction efficiency, since Dynabeads™ anti-CD3/CD28 (ThermoFisher) did not yield high transduction rates despite providing the highest signal strength Immunocult™ anti-CD3/CD28/CD2 which had a signal strength higher than coated anti-CD3 but lower than Dynabeads™, activated T cells with the highest expression of GFP and the engineered TCR. Activating leukapheresed cells with Immunocult™ anti-CD3/CD28/CD2 in the presence of different cytokine cocktails had an effect on transduction efficiency, however when compared at different cell densities, transduction of cells activated and grow in culture media containing IL-2 or IL-7/21/TWS119 were similar. Cells cultured in IL-2 and IL-7/21/TWS119 were compared and it was found that the IL-7/21/TWS119 condition promoted elevated transduction efficiency. These results have important implications for the use of a soluble activator, such as Immunocult™ anti-CD3/CD28/CD2, in a manufacturing process that leads to high numbers of functional engineered T cells for cell therapy applications.

Example 6 Optimum MOI for TCR Transduction

Figure 7B:
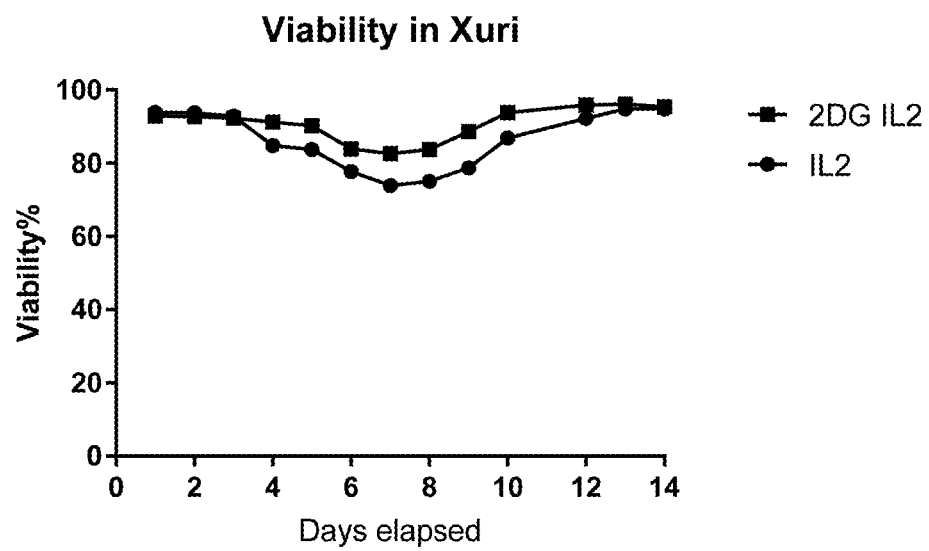

Previously frozen apheresed cells were thawed and activated with Immunocult™ CD3/CD28/CD2 (25 µl/ml of cells, Stemcell Technologies) for 24 hours, as described above. On day 1 post activation, a lentiviral vector comprising a polynucleotide encoding a TRC was added to $1\times10^6$ cells at an increased multiplicity of infection (MOI) (A), equal to or greater than a MOI of 1, or (B) decreasing MOIs of 2 or less. Cells were assayed for TCR expression 7 days post-transduction. No observable MOI effect was observed at MOIs greater than 1. Reported values are averages of TCR expression in CD8+ T cells from 4 different donors. FIGS. 30A and 7B show the MOI of 1 was optimal for lentiviral transduction in large-scale, closed bioprocess.

Example 7 a Closed Continuous Method for Rapidly Producing Genetically Engineered Autologous T Cells Expressing a T Cell Receptor This experiment looked at the effect of increased seeding cell density, increased oxygen supplement through feedback loop dissolved oxygen (DO) control, and increased mass transfer through reducing bioreactor volume while increasing agitation, on cell growth, transduction efficiency, and T cell phenotype.

On day 0, a fresh LEUKOPACK® (Hemacare, Northridge, CA), containing 300 ml fresh enriched leukapheresis product collected from normal peripheral blood was sterile welded to a CD-600.1 Sepax Cell Separation Kit (GE) and processed under Culture Wash-Pro program. The LEUKOPACK® contained leukocytes, erythrocytes, and platelets. The cells were washed in 1 L ClinMACS® PBS/EDTA, 5 ml human serum albumin (Miltenyi Biotec, San Diego, CA) to remove plasma and apheresis buffers using a Sepax CPro equipped with a CS-600.1 Kit (GE Healthcare) according to manufacturer's instructions. Based on the initial white blood cell (WBC) count indicated on the donor information sheet accompanying the LEUKOPACK®, the washed leukapheresed cells were eluted at a cell density of 150E6 WBC/ml with ~50 ml OpTmizer™ complete media.

The nucleated cells in the washed leukapheresed sample were counted using NC200™ Automated Cell Counter, followed by determining total viable cell count, viability, and immunophenotype of the washed leukapheresed cells.

Aliquots of the washed leukapheresed donor cells comprising 1.2E9 (low density (LD)) or 1.4E9 (high density (HC)) nucleated cells were then transferred into separate transfer bags (Charter Medicine) under the Dilute program using the Sepax C-Pro processing system with the same CD-600.1 Kit in ~6.5 ml OpTmizer™ complete media containing 300 IU/ml IL-2 (and was incubated with 7.5 ml ImmunoCult™ Human CD3/CD28/CD2 (2.5 µg/ml, Stemcell Technologies) at room temperature for 1 hour at room temperature to allow saturation of antibody binding.

Five 2 L XURI® SP Perf Cellbag™ bioreactors (GE Healthcare) were each connected to a separate bioreactor (XURI® Cell Expansion System W25). The bags contained 300 ml OpTmizer™ complete media comprising 300 IU/ml IL-2 for the three low density samples (Samples 1-3) or 200 ml OpTmizer™ complete media comprising 300 IU/ml IL-2 for the two high density samples (Samples 4-5), see Table 1. The bioreactors were allowed to equilibrate at 37° C., 5% $CO_2$, gas flow rate of 0.1 L/min at a rocking rate of 6 rpm at a 6° angle.

The three transfer bags containing the 1.2E9 nucleated cells (low density samples) and two transfer bags containing 1.4E9 nucleated cells (high density samples) were each sterile welded to a XURI® Cellbag feed-line and the contents transferred into each of the bioreactors by gravity. The low density samples (1.2e9 cells) were added to the bags containing 300 ml OpTmizer™ complete media containing 300 IU/ml IL-2 to reach seeding density of 3.54E6 cells/ml. The high density samples (1.4E9 cells) were added to the bags containing 200 ml OpTmizer™ complete media containing 300 IU/ml IL-2 to reach a seeding density of 7E6 cells/ml. The cells were then incubated overnight at 37° C., 5% $CO_2$, gas flow rate 0.1 L/min at a rocking rate of 2 rpm at a 2° angle, to facilitate activation.

For Sample 3 the dissolved oxygen (DO) level of the culture was measured with an in-line optical DO sensor at a 10-second interval and controlled at 80% of the saturated DO, calibrated using a feedback loop control program from Unicorn, starting on Day 0.

On Day 1, the nucleated cells in each bag were counted. An amount of a lentiviral vector (comprising a polynucleotide encoding a TCR) that corresponded to a MOI of 1 functional titer was diluted in 10 ml of OpTmizer™ complete media containing 300 IU/ml IL-2 and was placed in a transfer bag, a separate bag was prepared for each of the five samples. The transfer bags were sterile welded on to a XURI® Cellbag feed-line and the lentiviral vector was transferred into each of the bioreactors via gravity. The cells were incubated with the lentiviral vector at 37° C., 5% $CO_2$, gas flow rate of 0.1 L/min, and a rocking rate of 2 rpm at a 2° angle, for 20-24 hours.

On Day 2, about half the volume of the culture media in each bioreactor bag was exchanged for fresh OpTmizer™ complete media that included 300 IU/ml IL-2. This was done with three 50 ml washouts for Samples 1-3 and two 50 ml washouts for Samples 4 and 5. Cell counts were taken daily and viable cell density (VCD) and viability were determined using an NC200™ Automated Cell Counter (ChemMetec), dissolved oxygen, metabolites were also measured. Cell phenotypes were determined for all samples tested. The bags were maintained on the rocking bioreactors at 2 rpm at a 2° angle, 37° C., 5% $CO_2$, gas flow rate of 0.1 L/min, for 24 hours.

On Days 3-10 the Samples 1-5 were subjected to the conditions described in Table 1, increasing the culture volume, rate of agitation and angle in the prescribed stepwise manner until harvest.

TABLE 1

Stepwise increase in bioreactor volume at a specified rate of agitation in revolutions per minute (rpm) and at a specified angle, for low and high cell density samples.

| Samples | Low Density 0.35E6 cells/ml | High Density 0.7E6 cells/ml |
|---|---|---|
| 1 (Control) | 2 rpm at a 2° angle, 0.3 L<br>4 rpm at a 4° angle, 0.6 L<br>6 rpm at a 6° angle, 1.0 L | — |
| 2 | 2 rpm at a 2° angle, 0.3 L<br>3 rpm at a 3° angle, 0.4 L<br>6 rpm at a 6° angle, 0.5 L | — |
| 3 | 2 rpm at a 2° angle, 0.3 L<br>3 rpm at a 3° angle, 0.4 L<br>6 rpm at a 6° angle, 0.5 L<br>DO control at 80% starting at D 0 | — |
| 4 | — | 2 rpm at a 2° angle, 0.2 L<br>3 rpm at a 3° angle, 0.3 L<br>3 rpm at a 3° angle, 0.4 L<br>4 rpm at a 4° angle, 0.5 L |
| 5 | — | 2 rpm at a 2° angle, 0.2 L<br>3 rpm at a 3° angle, 0.3 L<br>3 rpm at a 3° angle, 0.4 L<br>6 rpm at a 6° angle, 0.5 L<br>DO control at 80% starting at maximal bioreactor volume |

On Day 3 the low density cultures (Samples 2-3 and the Control) were maintained at 300 ml OpTimzer complete media containing 300 IU/ml IL-2, by perfusing the culture with culture media at rate of one bag volume per day, with a rocking rate of 2 rpm at a 2° angle, at 37° C., 5% $CO_2$, with gas flow rate of 0.1 L/min, until the cell density reached 4E6 cells/ml. The high density samples (Samples 4-5) were maintained at 200 ml OpTimzer complete media containing 300 IU/ml IL-2, by perfusing the culture with culture media at a rate of one bag volume per day with a rocking rate of 2 rpm at a 2° angle, at 37° C., 5% $CO_2$, with gas flow rate of 0.1 L/min, until the cell density reached 4E6 cells/ml.

At that point, the volume of the culture media was increased to 600 ml with a rocking rate of 4 rpm at a 4° angle for the Control. The volume of culture media was increased to 400 ml with a rocking rate of 3 rpm at a 3° angle for Samples 2-3. The volume of culture media was increased to 300 ml with a rocking rate of 3 rpm at a 3° angle for Samples 4-5. All cultures were perfused at a rate of half a bioreactor volume per day and maintained at 37° C., 5% $CO_2$, with gas flow rate of 0.1 L/min, until the cell density again reached 4E6 cells/ml.

At that point, the volume of the culture media was increased to 1000 ml with a rocking rate of 6 rpm at a 6° angle for the Control. The Control was perfused at a rate of a half bioreactor volume (500 ml) per day, followed by perfusing at a rate of a bioreactor volume per day (1000 ml). For Samples 2-3, the culture volume was increased to 500 ml with a rocking rate of 6 rpm at a 6° angle. Samples 2-3 were perfused at a bioreactor volume (500 ml) per day, followed by perfusing at double the bioreactor volume (1000 ml). The Control and Samples 2-3 were maintained at 37° C., 5% $CO_2$, with gas flow rate of 0.1 L/min, until harvest when the cell yield was about 10 billion cells. The Control sample was harvested on Day 11 and Samples 2-3 were harvested on Day 9.

For Samples 4-5, the culture volume was maintained at 300 ml with an increased rocking rate of 4 rpm at a 4° angle. The cultures were maintained at 37° C., 5% $CO_2$, with gas flow rate of 0.1 L/min. until the cell density again reached 4E6 cells/ml. At that time, the Sample 4 culture volume was increased to 500 ml and the rocking rate of 4 rpm at a 4° angle was maintained until the cell yield reached about 10 billion cells. The culture was maintained at 37° C., 5% $CO_2$ with gas flow rate of 0.1 L/min until harvest on Day 9. For Sample 5, the culture volume was increased to 500 ml with a rocking rate of 6 rpm at a 6° angle. Once the culture volume of Sample 5 reached maximal volume, 500 ml, the dissolved oxygen was measured with an in-line optical DO sensor at a 10-second interval and controlled at 80% of the saturated DO, calibrated using a feedback loop control program from Unicorn. Sample 5 was maintained at 37° C., 5% $CO_2$, with gas flow rate of 0.1 L/min, and DO at 80%, until harvest on Day 9, when the cell yield had reached about 10 billion cells.

Total viable cell density, viability, glucose and lactate measurements were taken each day. Phenotyping was determined on days 3, 5 and 7.

For harvest, a XURI® SP Per bioreactor bag was sterile welded to a Selfia 5200 Cell Processing System using the FlexCell program and CT-800.1 Cell Processing kit (GE Healthcare) for each sample. The T cells were concentrated to ~20 ml at a 75 ml/min flow rate. One wash cycle was performed using 0.9% saline (Baxter, Deerfield, Ill) supplemented with 1% vol human serum albumin (HSA). The wash was performed at 380×g for 5 min.

The cells from all 5 cultures were then eluted at 2E8 cells/ml in saline supplemented with 1% HSA and were further formulated at a 1:1 ratio with HyClone™ Cryopreservation Media (GE Healthcare) supplemented with 5% human serum albumin. Final cell product was then split into two freezing bags and several cryovials, which were finally frozen down in VIA Freeze™ Quad freezer (GE) with a cooling rate of −1° C./min until the temperature reached −80° C. After freezing, cells were transferred to liquid nitrogen for long-term storage.

Results

Figure 32A:
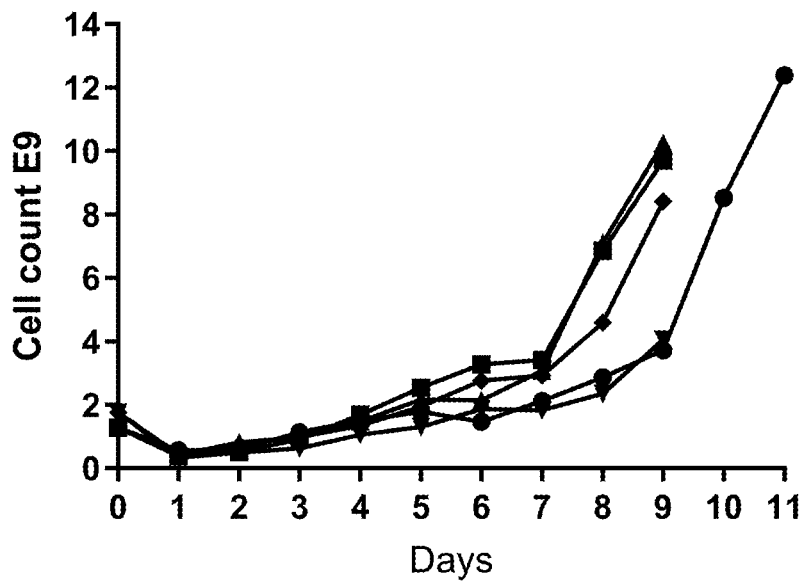
FIG. 32. Cell growth (A) and Viability (B) from day 0 to the day of harvest. Control solid circle, Sample 2 solid upward triangle, Sample 3 solid square, Sample 4 Solid downward triangle and Sample 5 solid diamond.
Figure 32B:
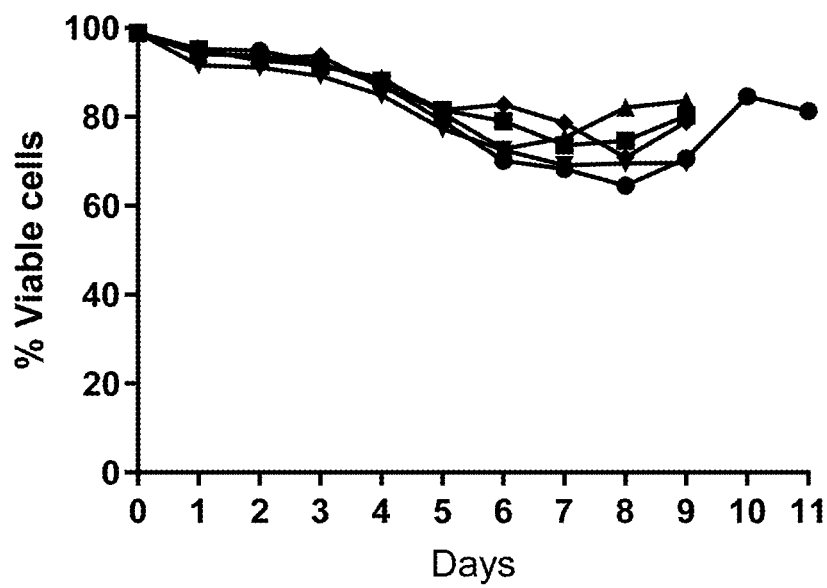

FIG. 32 shows cell growth and viability from day 0 to the day of harvest. Compared to the Control which generated <4 billion engineered T cells at day 9, Samples 2, 3, and 5 all significantly promoted cell growth to around 10 billion cells at day 9 through methods enhancing a greater level of oxygen transfer by either rocking agitation alone or in combination with direct oxygen supplement (DO feedback loop control), FIG. 32 (A) the Control represented by a solid circle, Sample 2 solid upward triangle, Sample 3 solid square, Sample 4 Solid downward triangle and Sample 5 solid diamond.

Moreover, Samples 2, 3, and 5 enhanced in-process cell viability from Day 6 to Day 9 compared to the Control while the end of process cell viability for Samples 2, 3, 5, and the Control were comparable FIG. 32 (B). The dip in viability was likely due to gradual die off of the non-T cells.

All conditions showed a similar dynamic pattern of TCR surface assembly and increased TCR surface expression over time during expansion, as measured by dextramer staining. However, a direct and steady oxygen delivery through a feedback loop control starting at Day 0 compromised transduction efficiency and as a result, Sample 3 showed the lowest TCR surface expression even through cell growth was superior to the Control. Supplying oxygen at a later stage when the bioreactor was fully scaled up (Sample 5) or enhancing a greater level of oxygen transfer through rocking agitation at 500 ml volume (Samples 2, 3) maintained TCR surface level similar to that of the Control. In addition, Sample 4, which had a higher seeding density at 7E6 cells/ml and was maintained at the same agitation level as the Control resulted a dramatic enhancement in transduction efficiency. TCR surface expression for Sample 4 was enhanced to 45.30% compared to the Control at 30.5%. However, cells in Sample 4 grew slower than cells from conditions where greater agitation and oxygen supply were performed (Samples 2, 3, and 5) while comparable to those from the Control. This suggested that cell density and oxygen level at the time of transduction may play important roles in affecting transduction efficiency. See FIG. 33, Control represented by a solid circle, Sample 2 solid upward triangle, Sample 3 solid square, Sample 4 Solid downward triangle and Sample 5 solid diamond.

Figure 33:
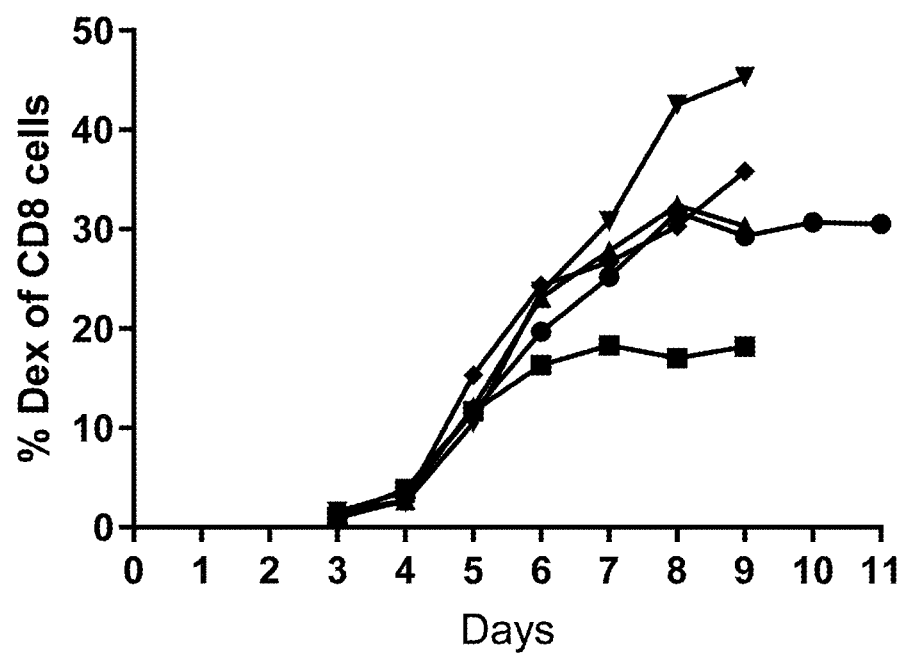
FIG. 33. Time course engineered T cell receptor (TCR) surface expression measured by dextramer staining Control solid circle, Sample 2 solid upward triangle, Sample 3 solid square, Sample 4 Solid downward triangle and Sample 5 solid diamond.
Figure 34:
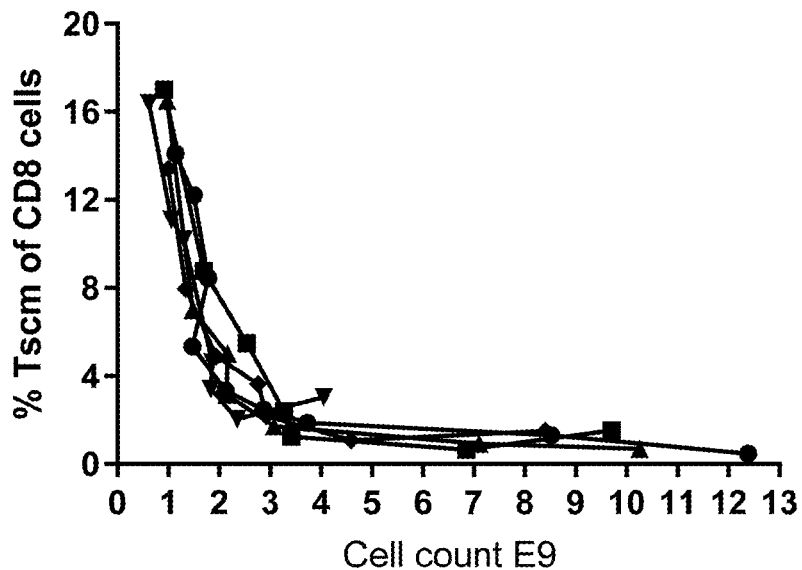
FIG. 34. Differentiation of T cells into stem cell memory (A), central memory (B) and effector memory (C) subsets as a function of cell growth. Control solid circle, Sample 2 solid upward triangle, Sample 3 solid square, Sample 4 Solid downward triangle and Sample 5 solid diamond.
Figure 34B:
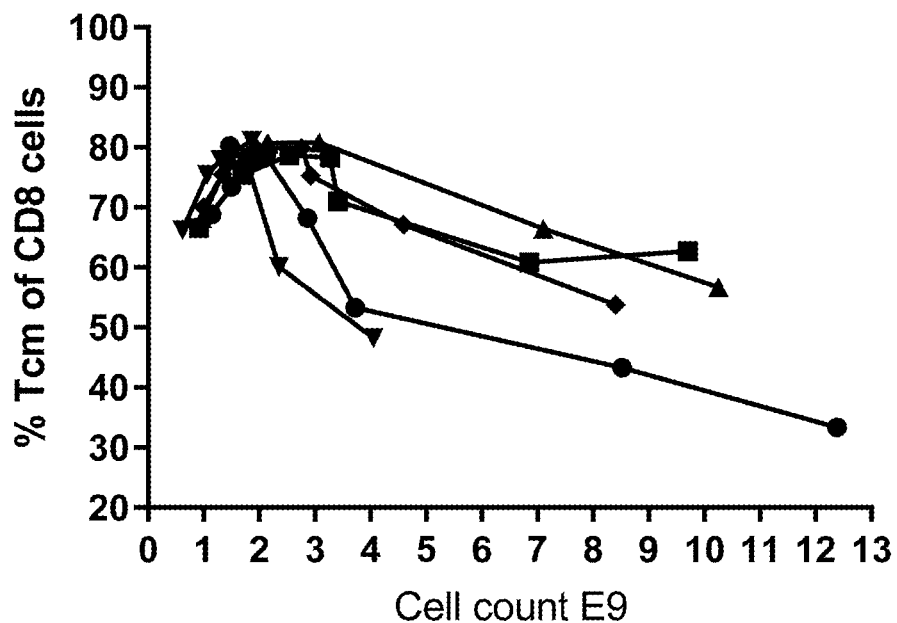
Figure 34C:
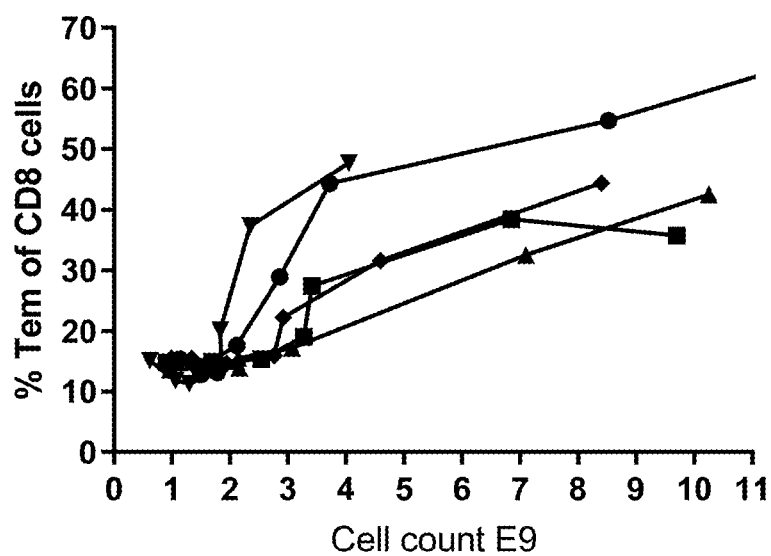

To determine differentiation, T cells subsets stem cell memory (Tscm) (CD45RA+, CD45RO−, CCR7+, CD95+), central memory (Tcm) (CD45RA−, CD45RO+, CCR7+, CD95+), and effector memory (Tem) (CD45RA−, CD45RO+, CCR7−, CD95+) were stained with an antibody cocktail and analyzed by flow cytometry at different timepoints. It is known that T cell activation and expansion is at the expense of continuous differentiation into effector phenotype from stem and central memory pools, a process associated with increased cellular cytotoxicity and diminished live span and overall persistence during cell therapy. Cells from Samples 2, 3, and 5 which employed higher agitation, less culture volume, and/or direct oxygen supply to achieve more sufficient oxygen transfer, contained significantly less % Tem cells than cells from the Control and Sample 4 when compared at the same cell yield. It was also noted that while cells from Sample 4 had the highest TCR surface expression (as seen in FIG. 33) among all the conditions tested, cell growth (as seen in FIG. 32) and % Tcm were only similar to the Control and lower than the rest of conditions tested. On the other hand, while cells from Sample 3 which used direct oxygen supply starting from day 0, showed low differentiation and enhanced cell growth, their TCR surface expression was 3-fold less than cells from Sample 4 (as seen in FIG. 33). This suggests the possible opposing effects of oxygen in achieving high transduction efficiency, cell growth, and T cell phenotype and the level and stage of oxygen delivered to bioreactor may play important roles in optimizing transduction efficiency, cell growth, and T cell phenotype matrix. See FIG. 34 (A) stem cell memory, (B) central memory, and (C) effector memory subsets as a function of cell growth. Control represented by a solid circle, Sample 2 solid upward triangle, Sample 3 solid square, Sample 4 Solid downward triangle and Sample 5 solid diamond.

Figure 35:
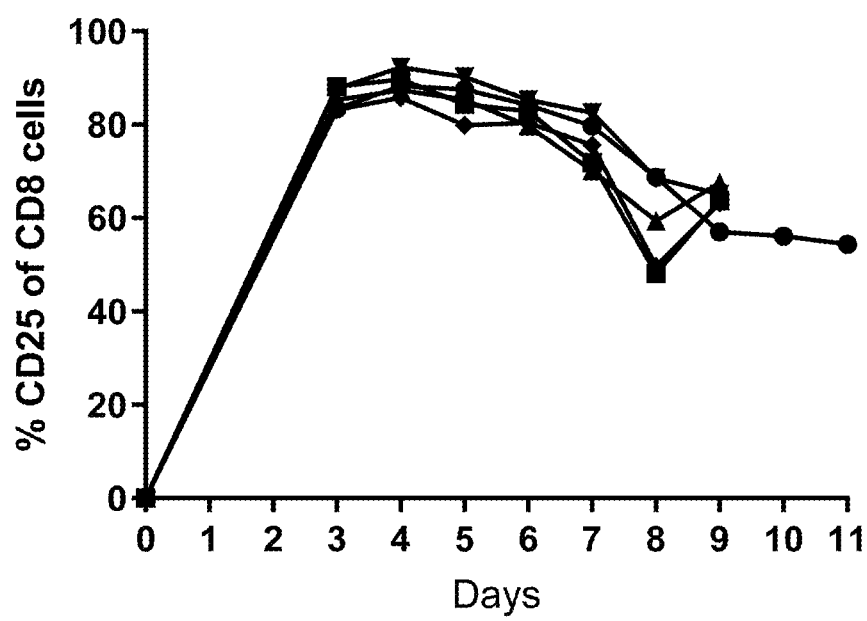
FIG. 35. Activation profile measured by CD25 surface expression. Control solid circle, Sample 2 solid upward triangle, Sample 3 solid square, Sample 4 Solid downward triangle and Sample 5 solid diamond.
Figure 36A:
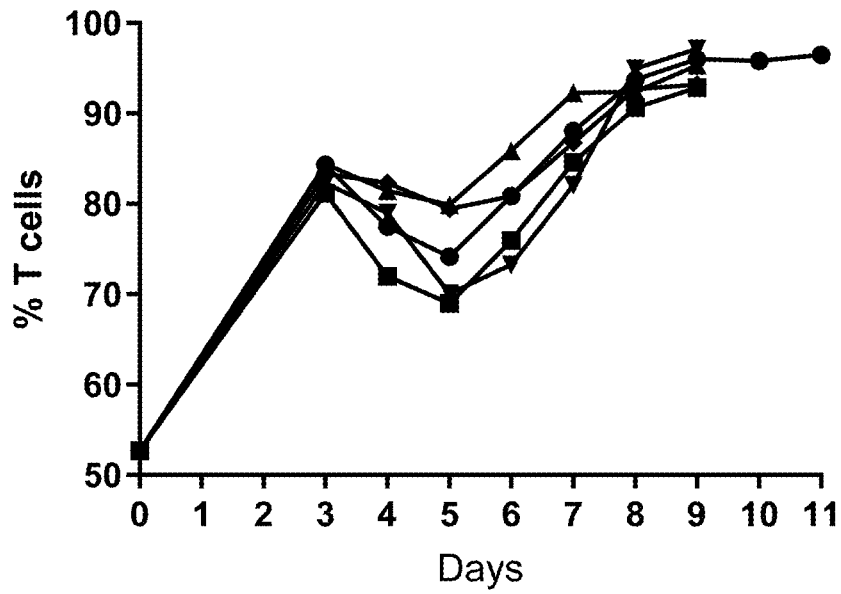
FIG. 36. Time course percentage of leucocytes subsets, including T cells (A), B cells (B), monocytes (C), and NK cells (D). Control solid circle, Sample 2 solid upward triangle, Sample 3 solid square, Sample 4 Solid downward triangle and Sample 5 solid diamond.
Figure 36B:
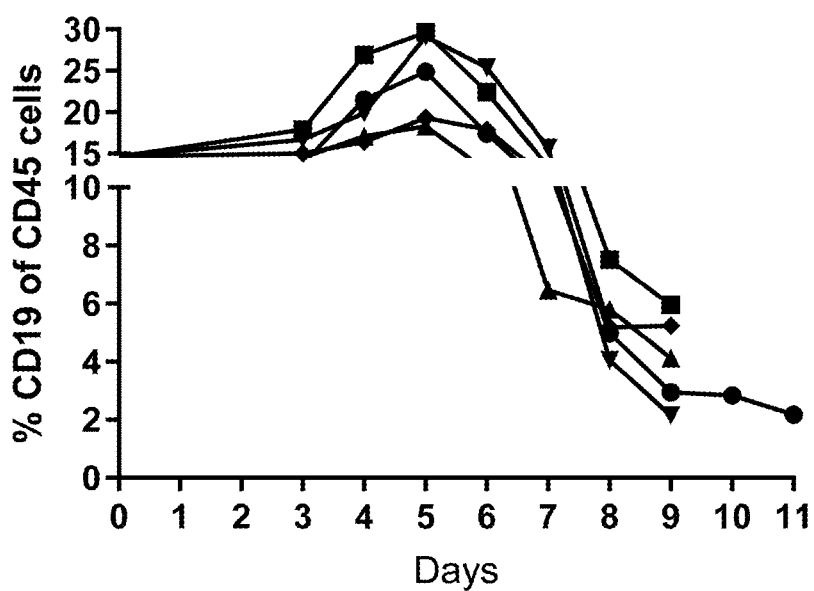
Figure 36C:
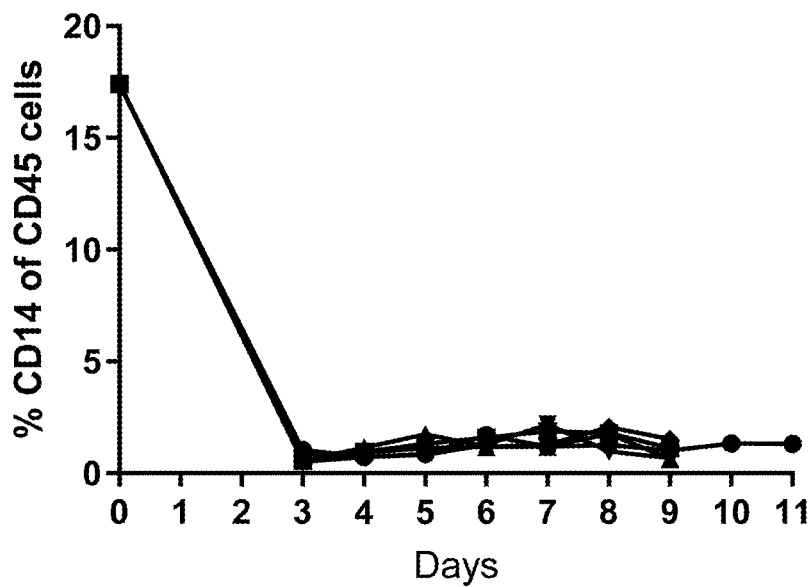
Figure 36D:
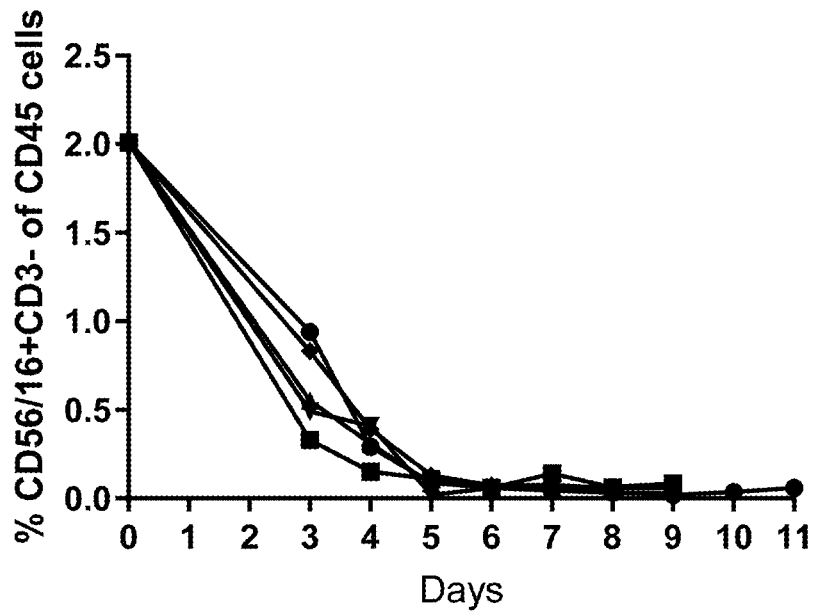

The activation profile was measured by CD25 surface expression. Activation status was similar between different conditions. CD25 surface expression peaked at around day 3 and decreased gradually as cell expanded. See FIG. 35, Control represented by a solid circle, Sample 2 solid upward triangle, Sample 3 solid square, Sample 4 Solid downward triangle and Sample 5 solid diamond.

A time course percentage of leucocytes subsets T cells, B cells, monocytes, and NK cells, was determined. The cells were stained with an antibody cocktail targeting B cells (CD19), Monocytes (CD14), NK cells (CD3−, CD56+), and T cells (CD3+) and analyzed by flow cytometry. Due the nature of CD3 antigen downregulation upon T cell activation and B cell CD3 antigen acquisition from T cells, % T cells was calculated by subtracting % monocytes, % B cells, % NK cells from 100%. All tested conditions showed a similar pattern of leucocyte subsets where B cells enriched slightly in the first 5 days followed by graduate diminishing till the end of process and T cells diluted in the first 5 days as a result of B cell enrichment, continuously enriched starting from Day 5 till the end of process. Overall, T cell purity for all test conditions at the end of process was above 90% with the Control and Sample 4 having the highest T cell purity at 96.47% and 97.15% respectively, followed by Sample 2 having purity at 95.31% and Samples 3 and 5 below 95%. See FIG. 36 T cells (A), B cells (B), monocytes (C), and NK cells (D). Control represented by a solid circle, Sample 2 solid upward triangle, Sample 3 solid square, Sample 4 Solid downward triangle and Sample 5 solid diamond.

Figure 37:
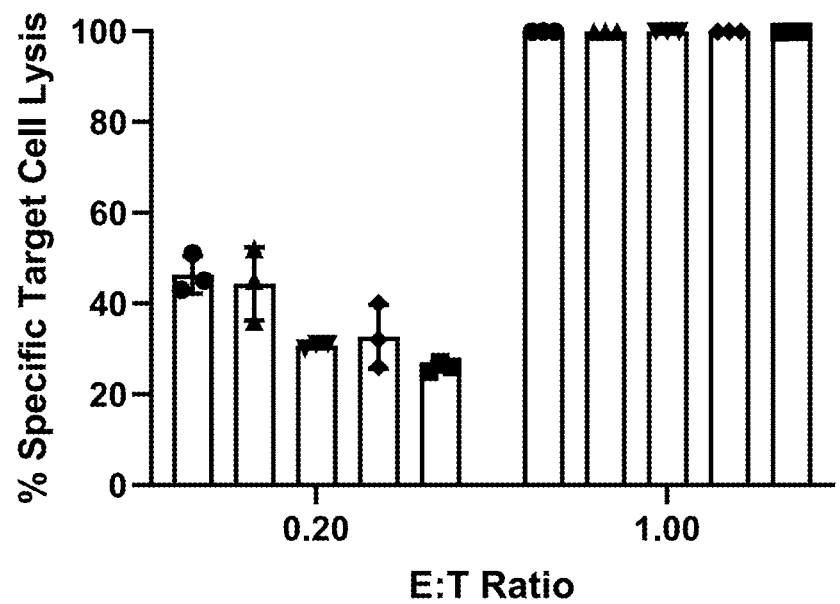
FIG. 37. Percentage of killing of target cells at different effector to target cells (E:T) ratios. Control solid circle, Sample 2 solid upward triangle, Sample 3 solid square, Sample 4 Solid downward triangle and Sample 5 solid diamond.

The percentage of killing of target cells at different effector to target cells (E:T) ratios was determined. Harvested T cells were co-cultured for 24 hours with T2 cells pulsed with and without peptide at an E:T ratio at 1:5 and 1:1. Percentage of killing of target cells was calculated by the percentage of cell death of target cells after 24 hours of co-culture. All tested conditions showed >99% target cell lysis when E:T ratio was at 1. At a lower E:T ratio of 1:5, the Control and Sample 2 had comparable % target cell lysis while the other conditions, Samples 3, 4, and 5, showed slightly lower % target cell lysis. See FIG. 37, the Control is represented by a solid circle, Sample 2 solid upward triangle, Sample 3 solid square, Sample 4 Solid downward triangle and Sample 5 solid diamond.

The experiment described above was repeated with cells from a different donor (Donor #2) at a seeding density of 4E6 cells/ml. Two samples were tested having a step wise increase in bioreactor volume, agitation and angle. Based on the observations from the above that cell doubling time was shorter with a culture volume of 0.5 L at 6 rpm at a 6° angle compared to 0.4 L at 3 rpm at a 3° angle, the intermediate agitation and volume was increased to 5 rpm at a 5° angle (5×5) at 0.4 L for Sample 2. The step wise increase in bioreactor volume, agitation and angle for Sample 2 was 2 rpm at an angle of 2° at a volume of 0.3 L, 5 rpm at an angle of 5° at a volume of 0.4 L, and 6 rpm at an angle of 6° at a volume of 0.5 L. The Control was maintained at 2 rpm at an angle of 2° at a volume of 0.3 L, 4 rpm at an angle of 2° at a volume of 0.6 L, 6 rpm at an angle of 6° at a volume of 1.0 L. Each stepwise increase in bioreactor volume, agitation and angle was made when the cell density in the bioreactor reached 4E6 cells/ml. The cells were harvested when they reached a target yield of ~10 billion cells.

Figure 38A:
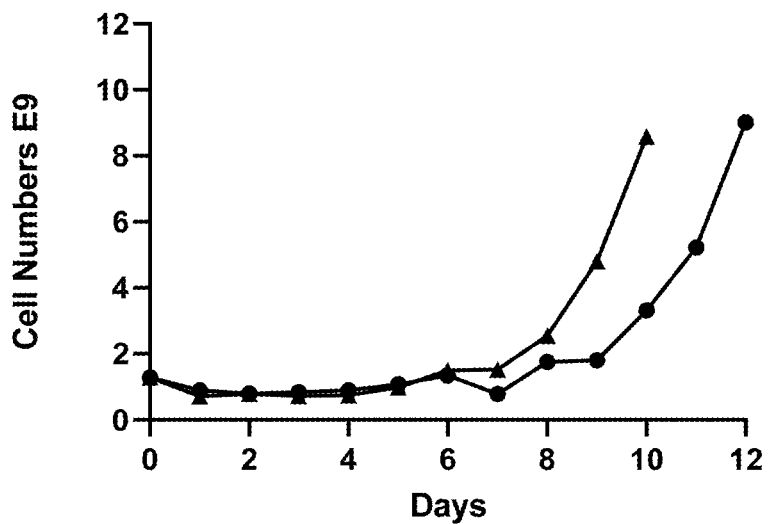
FIG. 38. Cell growth (A) and Viability (B) from day 0 to the day of harvest. Control solid circle. Sample 2 solid upward triangle.
Figure 38B:
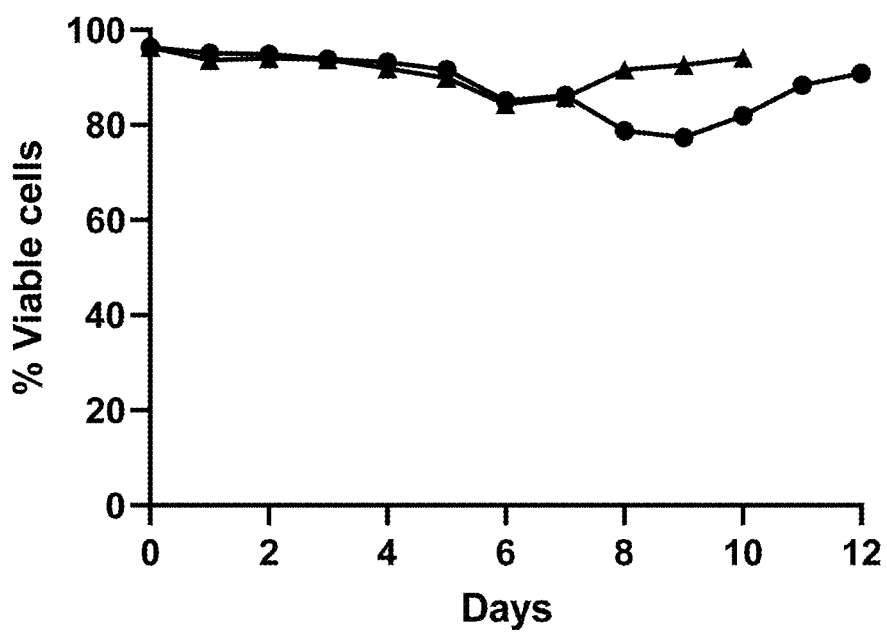

Cells in Sample 2 with enhanced agitation with reduced bioreactor volume showed increased growth compared with cells in the Control, see FIG. 38A, Control (solid circle). For Sample 2 (solid upward triangle), cell numbers increased starting from day 7 to the end of process and reached >9 billion cells in 10 days, while cells from the Control reached >9 billion cells at day 12. Cells from Sample 2 also showed higher viability at Days 8, 9, and 10 than cells from the Control, however, the end of process viability for the Control and Sample 2 were comparable, see FIG. 38B.

Figure 39:
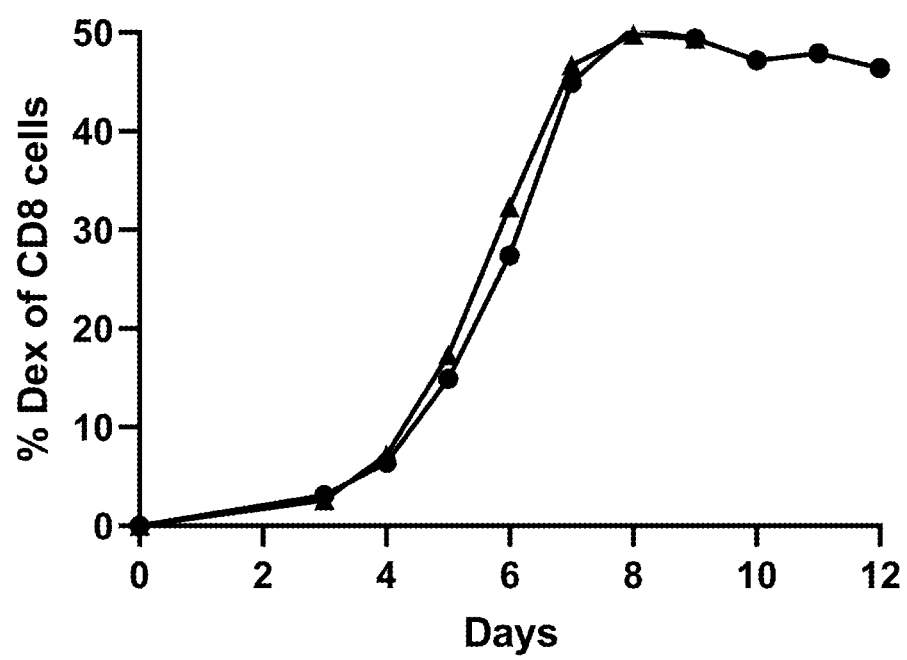
FIG. 39. Time-course engineered T cell receptor (TCR) surface expression measured by dextramer staining Control solid circle. Sample 2 solid upward triangle.

Both the Control and Sample 2 showed a similar dynamic pattern of TCR surface assembly over time and comparable TCR surface expression at the end of process, as determined by dextramer staining, see FIG. 39, Control: solid circle, Sample 2: solid upward triangle.

Figure 40:
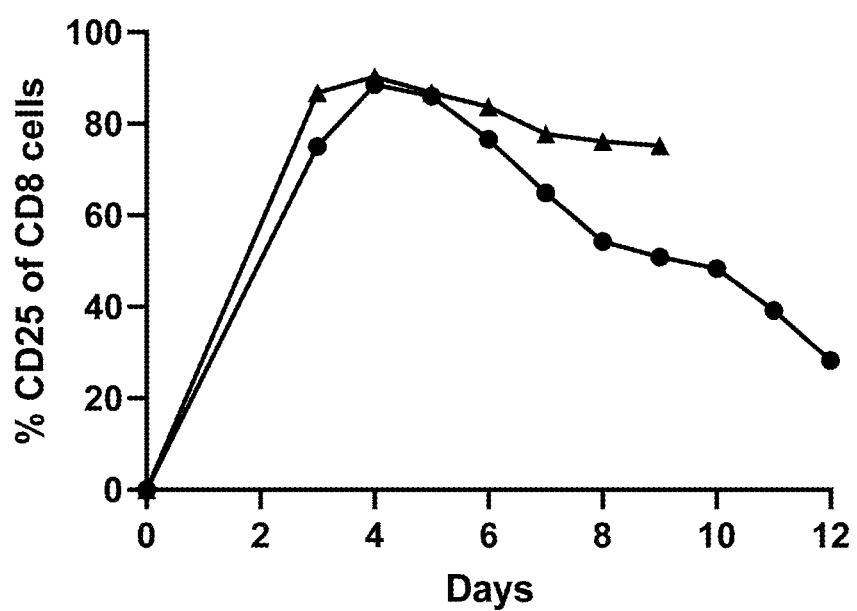
FIG. 40. Activation profile indicated by CD25 surface expression. Control solid circle. Sample 2 solid upward triangle.

An activation profile indicated by CD25 surface expression was determined. CD25 expression decreased more rapidly for cells in the Control than cells in Sample 2, starting from Day 4 and continuing throughout the process. Cells in the Control showed ~50% lower CD25 expression than cells in Sample 2 at the end of process, FIG. 40, Control: solid circle, Sample 2: solid upward triangle.

Figure 41A:
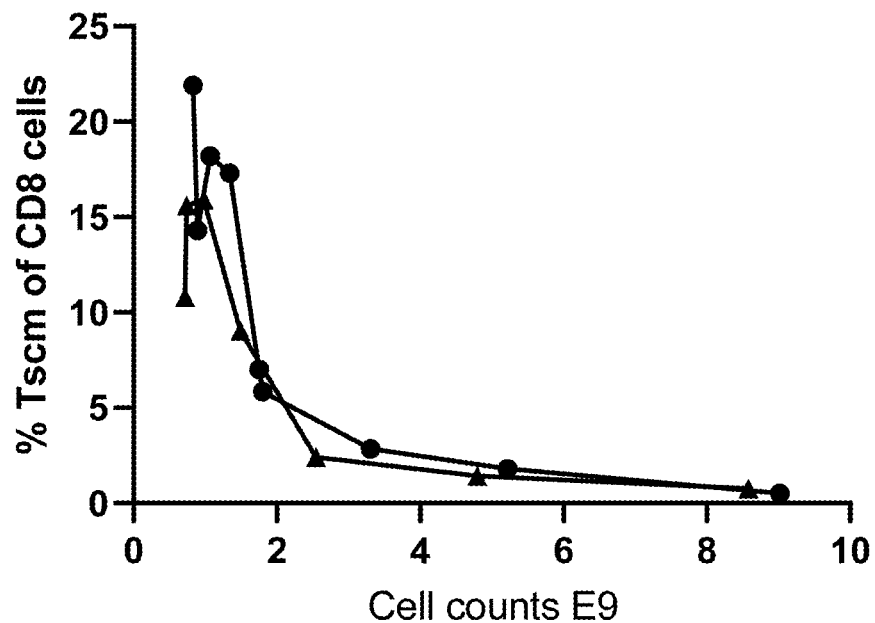
FIG. 41. Differentiation of T cells into stem cell memory (A), central memory (B) and effector memory (C) subsets as a function of cell growth. Control solid circle. Sample 2 solid upward triangle.
Figure 41B:
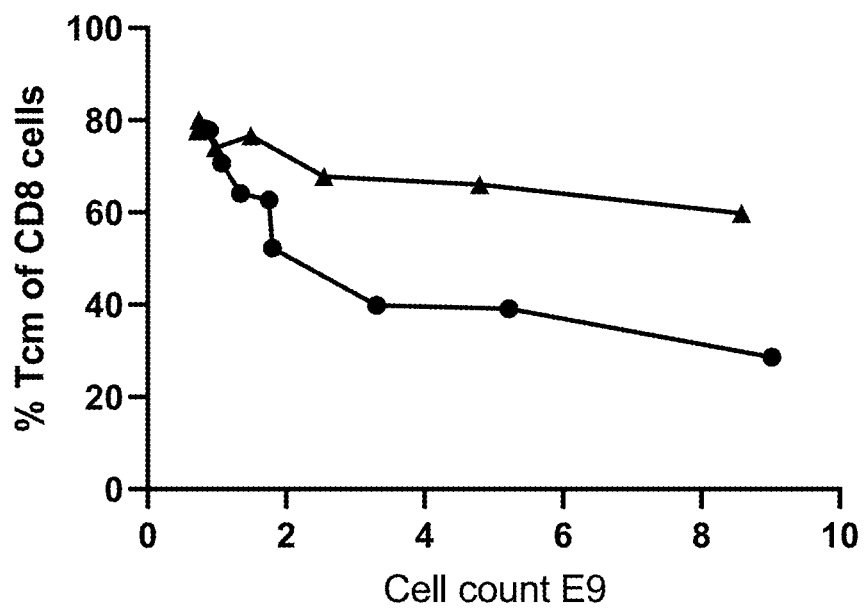
Figure 41C:
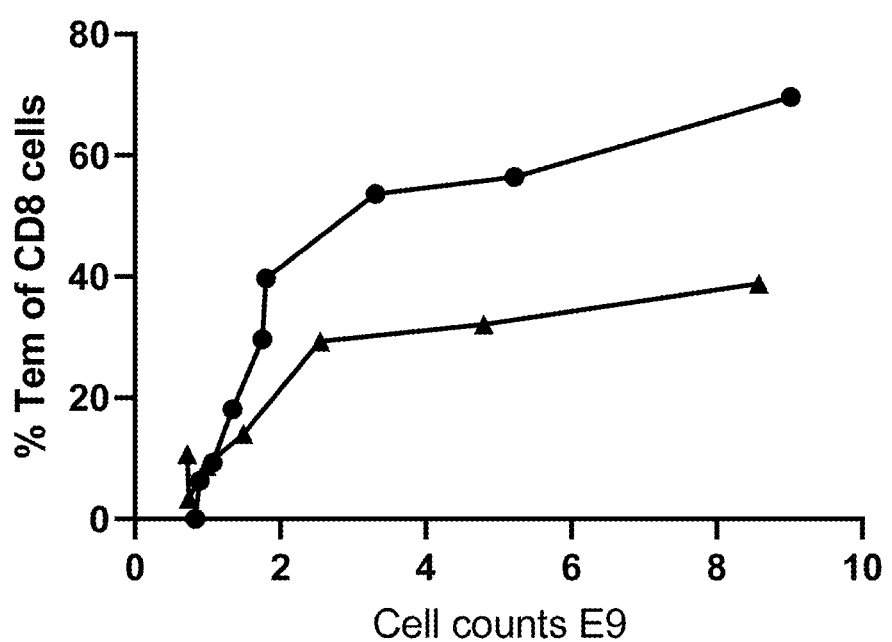
Figure 42A:
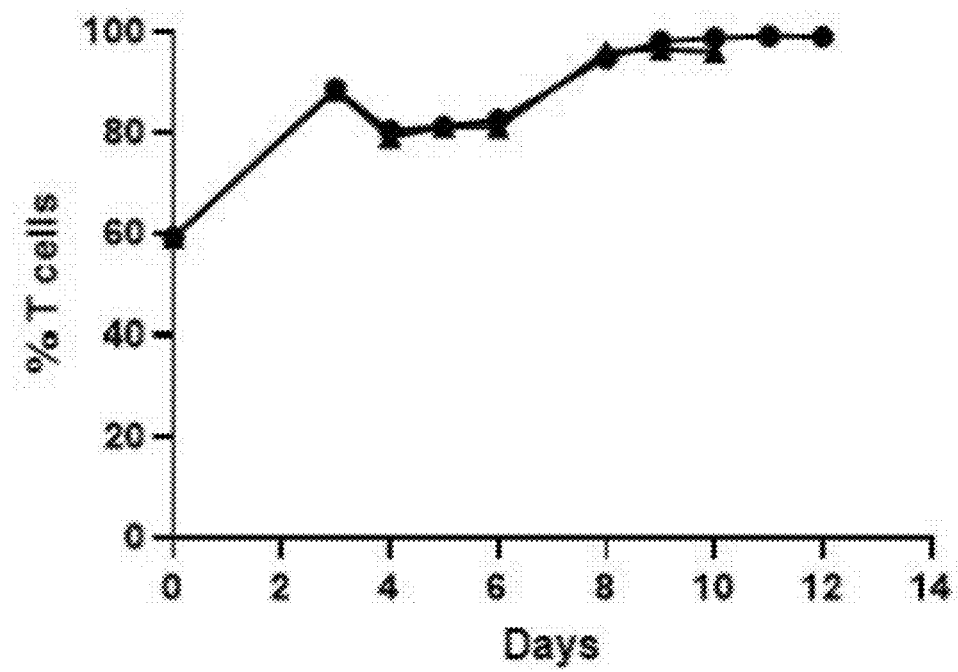
FIG. 42. Time course percentage of leucocytes subsets, including T cells (A), B cells (B), monocytes (C), and NK cells (D). Control solid circle. Sample 2 solid upward triangle.
Figure 42B:
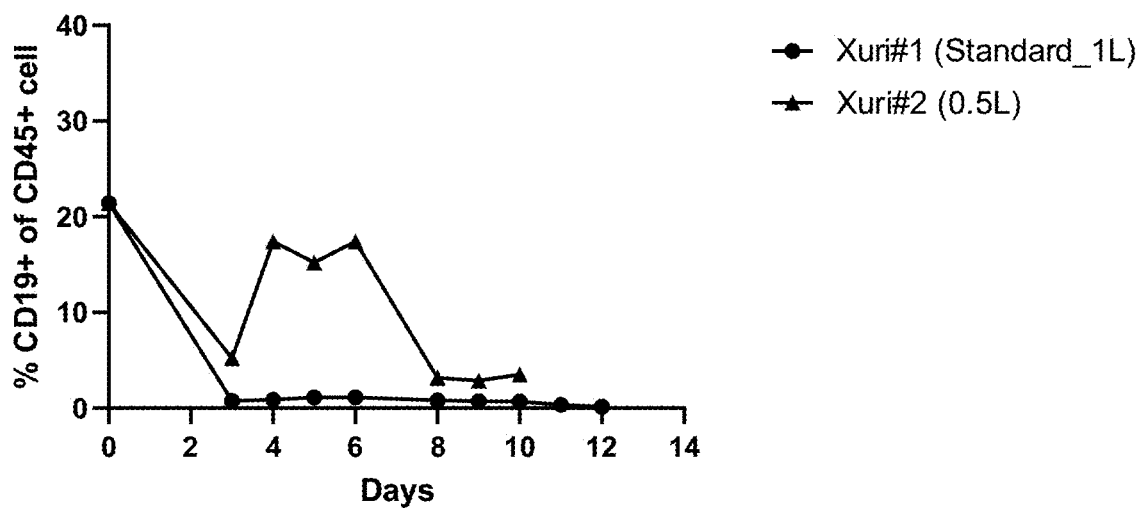
Figure 42C:
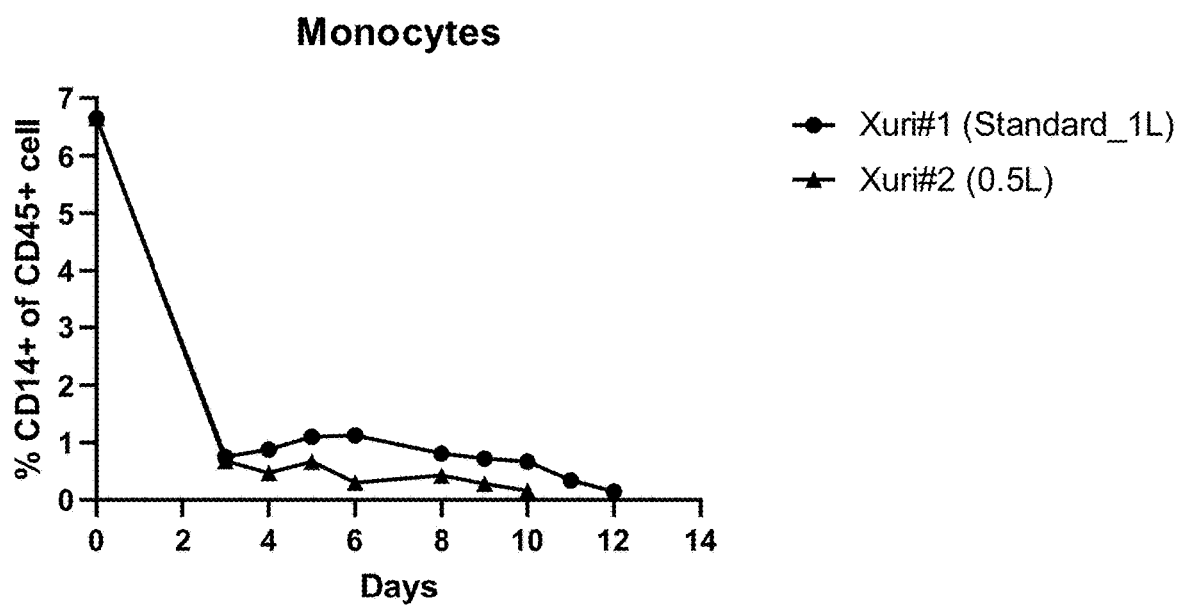
Figure 42D:
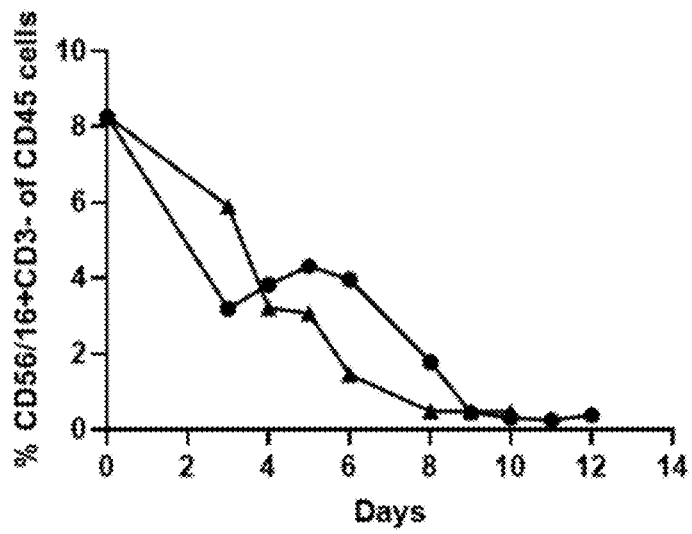

Differentiation of the T cells produced under each condition was also determined. T cell subsets Tscm (CD45RA+, CD45RO−, CCR7+, CD95+), Tcm (CD45RA−, CD45RO+, CCR7+, CD95+), and Tem (CD45RA−, CD45RO+, CCR7−, CD95+) were stained with antibody cocktail and analyzed by flow cytometry at different timepoints. No significant difference in the % of Tscm was observed between two condition tested. However, cells in Sample 2 with enhanced agitation and reduced bioreactor volume showed 30-40% higher level of Tcm (lower level of Tem) subset than the Control cells when compared at the same cell yield, FIG. 41 (A: stem cell memory), (B: central memory) and (C: effector memory), the Control is represented by a solid circle and Sample 2 is represented by a solid upward triangle.

Figure 43:
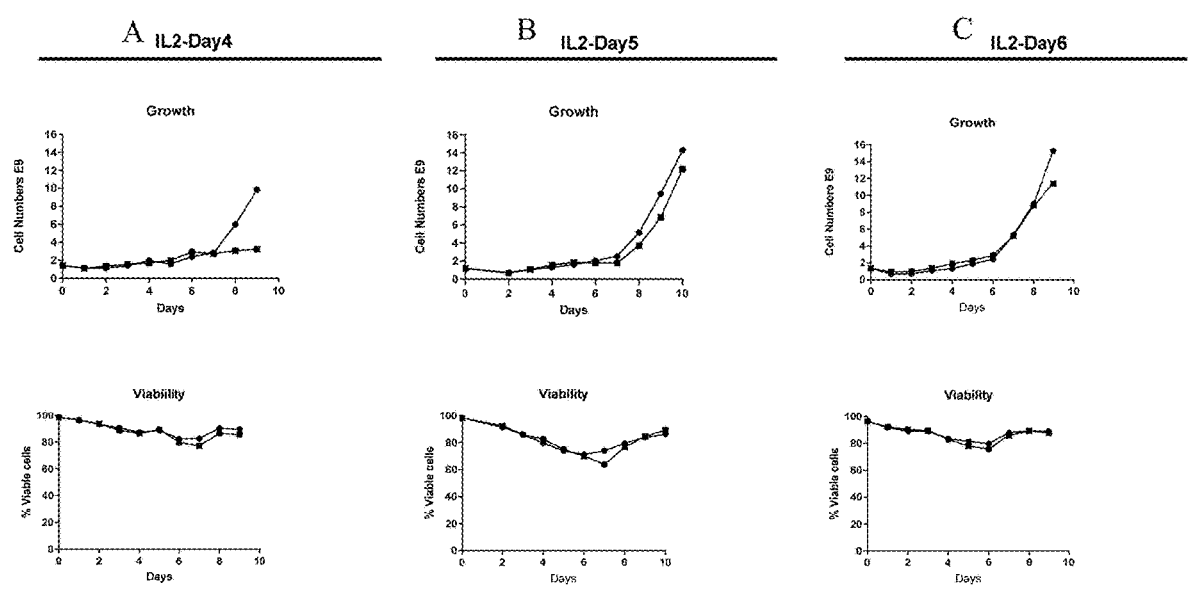
FIG. 43. Cell growth and viability. Control solid circle. Test sample solid square. (A) IL-2 withdrawal on Day 4 of the culture. (B) IL-2 withdrawal on Day 5 of the culture. (C) IL-2 withdrawal on Day 6 of the culture.

The cells were also stained with an antibody cocktail targeting B cells (CD19), Monocytes (CD14), NK cells (CD3−, CD56+), and T cells (CD3+) and analyzed by flow cytometry. Due the nature of CD3 antigen downregulation upon T cell activation and B cell CD3 antigen acquisition from T cells, % T cells was calculated by subtracting % monocytes, % B cells, % NK cells from 100%. While cells from sample 2 had lower monocytes and NK cells in process, the end of process T cell purity are similar between cells from the Control and Sample 2. FIG. 43 shows the time course percentage of leukocytes subsets, T cells (A), B cells (B), monocytes (C), and NK cells (D). The Control is represented by a solid circle and Sample 2 is represented by a solid upward triangle.

The results from Sample 2 from both Donor #1 and Donor #2 demonstrated that appropriate agitation at different bioreactor volumes promoted increased cell growth rate and led to a shorter expansion time and resulted in more desired T cell phenotypes. In addition, higher cell density appeared to play a positive role in affecting lentivirus vector transduction efficiency, as seen with Sample 4. However, this positive effect was abrogated if too much stimuli was introduced via oxygen as seen with Sample 5. Although enhanced agitation to promote air transfer in the system resulted in an increased growth rate and shorter expansion time, direct DO control at 80% of saturated DO via oxygen was not found to further promote cell growth, and in fact adversely affected lentivirus vector transduction efficiency, as was seen with Sample 3. Overall, a stepwise increase in culture volume from 0.3 L to 0.4 L to 0.5 L, and a stepwise increase in agitation and angle from 2 rpm at an angle of 2° to 5 rpm at an angle of 5° to 6 rpm at an angle of 6° over the course of a culture was found to achieve a balanced growth rate, memory T cell phenotype, and transduction efficiency.

Example 8 a Closed Continuous Method for Producing Genetically Engineered Autologous T Cells Receptors that have Minimal Activation Signaling and Peptide Irrelevant Toxicity On day 0, a fresh LEUKOPACK® (Hemacare, Northridge, CA), containing 300 ml fresh enriched leukapheresis product collected from normal peripheral blood was sterile welded to a CD-600.1 Sepax Cell Separation Kit (GE) and processed under Culture Wash-Pro program. The LEUKOPACK® contained leukocytes, erythrocytes, and platelets. The cells were washed in 1 L ClinMACS® PBS/EDTA, 5 ml human serum albumin (Miltenyi Biotec, San Diego, CA) to remove plasma and apheresis buffers using a Sepax CPro equipped with a CS-600.1 Kit (GE Healthcare) according to manufacturer's instructions. Based on the initial white blood cell (WBC) count indicated on the donor information sheet accompanying the LEUKOPACK®, the cells were eluted at a cell density of 150E6 WBC/ml with ~50 ml OpTmizer™ complete media.

The nucleated cells in the washed leukapheresed harvest sample were counted using NC-200™ Automated Cell Counter followed by determining total viable cell count, viability, and immunophenotype of the washed cells.

A sample of the washed apheresed donor cells comprising 1.2E9 nucleated cells was then transferred into a transfer bag (Charter Medicine) under the Dilute program using the Sepax C-Pro processing system with the same CD-600.1 Kit in ~6.5 ml OpTmizer™ complete media containing 300 IU/ml IL-2 and was incubated with 7.5 ml ImmunoCult™ Human CD3/CD28/CD2 (2.5 µg/ml, Stemcell Technologies) at room temperature for 1 hour at room temperature to allow saturation of antibody binding.

Four 2 L XURI® SP Perf Cellbag bioreactors (Cytiva) were each connected to a separate XURI® Cell Expansion System W25. To each bag was added 300 ml OpTmizer™ complete media containing 300 IU per ml IL-2 which was allowed to equilibrate at 37° C., 5% $CO_2$, gas flow rate of 0.1 L/minute, rocking at a rate of 6 rpm at a 6° angle. One XURI® SP Perf Cellbag bioreactor was prepared for each of the conditions to be tested:

"Control" IL-2 at a concentration of 300 IU/ml was maintained in the culture media from Day 0 until harvest.

"Day 4", IL-2 at a concentration of 300 IU/ml was maintained in the culture media at a concentration of 300 IU/ml from Day 0 to Day 3 of the culture, on Day 4 of the culture IL-2 was withdrawn from the perfusion media.

"Day 5", IL-2 at a concentration of 300 IU/ml was maintained in the culture media at a concentration of 300 IU/ml from Day 0 to Day 4 of the culture, on Day 5 of the culture IL-2 was withdrawn from the perfusion media.

"Day 6", IL-2 at a concentration of 300 IU/ml was maintained in the culture media at a concentration of 300 IU/ml from Day 0 to Day 5 of the culture, on Day 6 of the culture IL-2 was withdrawn from the perfusion media.

Each transfer bag was then sterile welded to a XURI® Cellbag feed-line and the contents transferred into one of the equilibrated bioreactors by gravity. The cells were then incubated overnight at 37° C., 5% $CO_2$, gas flow rate 0.1 L/min at a rocking rate of 2 rpm at a 2° angle, to facilitate activation.

On Day 1, the nucleated cells in each bag were counted. An amount of a lentiviral vector (comprising a polynucleotide encoding a TCR) that corresponded to a MOI of 1 functional titer was diluted in 10 ml of OpTmizer™ complete media containing IL-2 at a concentration of 300 IU/ml and was placed in a transfer bag. The transfer bag was sterile welded on to the XURI® Cellbag feed-line and lentiviral vector was transferred into the bioreactor via gravity. The cells were incubated at 37° C., 5% $CO_2$, gas flow rate of 0.1 L/min, and a rocking rate of 2 rpm at a 2° angle, for 20-24 hours.

On Day 2, about half the volume of the culture media in the bioreactor bag was exchanged for fresh OpTmizer™ complete media including IL-2 at a concentration of 300 IU/ml using three 50 ml washouts. Cell counts were taken daily and viable cell density (VCD) and viability were determined using NC200, dissolved oxygen, metabolites were also measured. Cell phenotypes were determined for all samples tested. The bags were maintained on the rocking bioreactors at 2 rpm at a 2° angle, 37° C., 5% $CO_2$, gas flow rate of 0.1 L/min, for 24 hours.

Starting on Day 3 the culture was maintained at 300 ml OpTimzer™ complete media including IL-2 at a concentration of 300 IU/ml by perfusion feeding at a rate of one bag volume per day, with a rocking rate of 2 rpm at a 2° angle, at 37° C., 5% $CO_2$, with gas flow rate of 0.1 L/min, to allow for culture expansion until the cell density reached 4E6 cells/ml.

At that point, the volume of the culture media was increased to 400 ml, perfusing at a rate of half bioreactor volume (200 ml) per day, with a rocking rate of 5 rpm at a 5° angle, at 37° C., 5% $CO_2$, with gas flow rate of 0.1 L/min, to allow for culture expansion until the cell density again reached 4E6 cells/ml.

At that point the volume of the culture media was increased to 500 ml, perfusing at a rate of half bioreactor volume (250 ml) per day, with a rocking rate of 6 rpm at a 6° angle, at 37° C., 5% $CO_2$, with gas flow rate of 0.1 L/min to allow for culture expansion. The perfusion rate increased at 24 hour intervals from half bioreactor volume (250 ml) to one bioreactor volume (500 ml), and finally to double the bioreactor volume (1000 ml) and maintained at a perfusion rate of 1000 ml until harvest.

IL-2, at a concentration of 300 IU/ml, was included in the perfusion media of all four cultures at the start of the culture expansion. On Day 4 of the culture ("Day 4"), IL-2 was withdrawn from the perfusion media of one culture. On Day 5 of the culture ("Day 5"), IL-2 was withdrawn from the perfusion media of a second culture. On Day 6 of the culture ("Day 6"), IL-2 was withdrawn from the perfusion media of a third culture. A control culture ("Control") continued to receive IL-2 in the perfusion media until harvest.

Total viable cell density, viability, glucose and lactate measurements were taken each day. Phenotyping was determined on Days 3, 5 and 7.

The cells from all of the bioreactors were harvested on Day 10. The XURI® SP Per bioreactor bags were sterile welded to a Selfia 5200 Cell Processing System using the FlexCell program and CT-800.1 Cell Processing kit (Cytiva). The T cells from each bioreactor were concentrated to ~20 ml at a 75 ml/min flow rate. One wash cycle was performed using 0.9% saline (Baxter, Deerfield, Ill) supplemented with 1% vol human serum albumin (HSA). The wash was performed at 380×g for 5 min.

The cells were then eluted at 2E8 cells/ml in saline supplemented with 1% HSA and were further formulated at a 1:1 ratio with HyClone™ Cryopreservation Media (GE Healthcare) supplemented with 5% human serum albumin. Final cell product was then split into two freezing bags and several cryovials, which were finally frozen down in VIA Freeze™ Quad freezer (GE) with a cooling rate of −1° C./min until the temperature reached −80° C. After freezing, cells were transferred to liquid nitrogen for long-term storage.

Results

Cell growth and viability for cells cultured in the presence of IL-2 from Day 0 to Day 4 (Day 4) (A) (Solid Square), from Day 0 to Day 5 (Day 5) (Solid Square) (B), or from Day 0 to Day 6 (Day 6) (Solid Square) (C), compared to a Control that received IL-2 continuously from Day 0 until harvest (Solid circle) is shown in FIG. 43. Withdrawing IL-2 at a later stage (e.g. Day 5 and Day 6) had minimal or no impact on cell growth or viability, however, IL-2 withdrawal at an earlier stage, Day 4, inhibited cell expansion significantly but did not affect cell viability.

Figure 44:
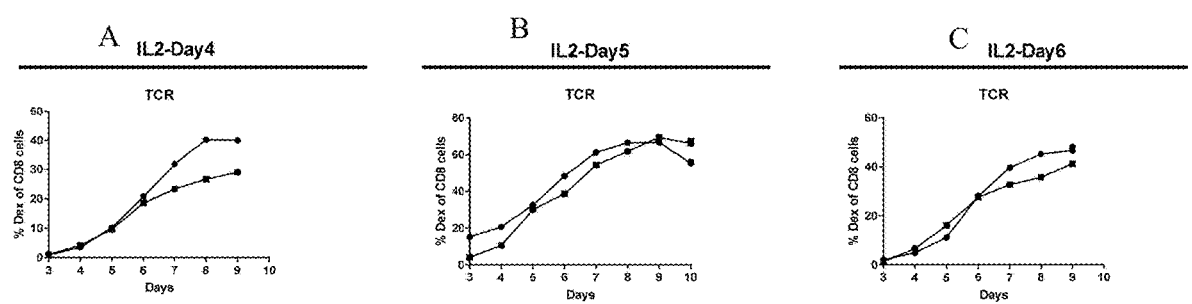
FIG. 44. Engineered T cell receptor (TCR) surface expression measured by dextramer staining at different timepoint. Control solid circle. Test sample solid square. (A) IL-2 withdrawal on Day 4 of the culture. (B) IL-2 withdrawal on Day 5 of the culture. (C) IL-2 withdrawal on Day 6 of the culture.

Engineered T cell receptor (TCR) surface expression was determined at different timepoints. Dextramer staining was performed to measure surface expression of T cell receptor on transduced and untransduced T cells. IL-2 withdrawal at Day 5 (B) or Day 6 (C) (Solid square) led to similar or higher TCR surface expression compared to the Control that received 300 IU/ml IL-2 continuously, see FIG. 44 (Control, Solid circle). However, IL-2 withdrawal at Day 4 (A) (Solid square) resulted in reduced TCR surface expression.

Figure 45:
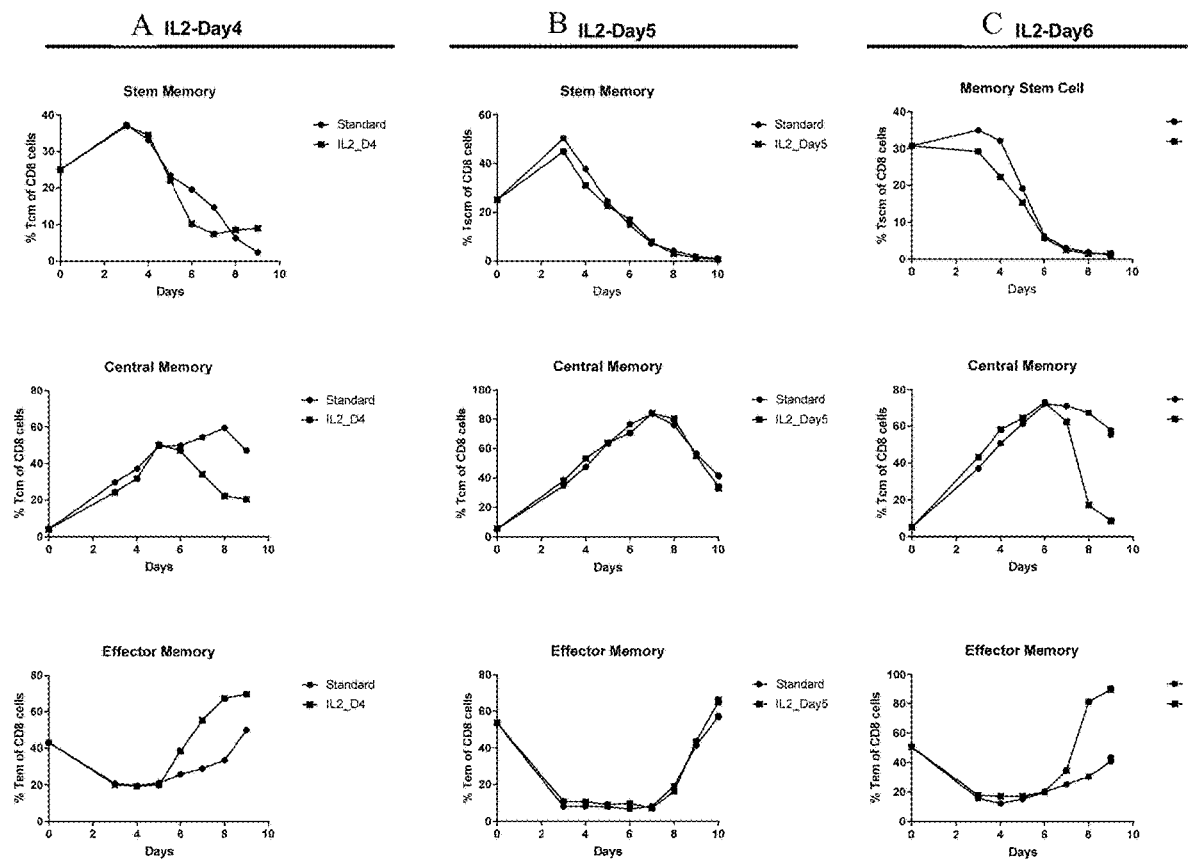
FIG. 45. Differentiation of T cell into stem cell memory, central memory, and effector memory subsets at different timepoint. Control solid circle. Test sample solid square. (A) IL-2 withdrawal on Day 4 of the culture. (B) IL-2 withdrawal on Day 5 of the culture. (C) IL-2 withdrawal on Day 6 of the culture.

FIG. 45 shows differentiation of T cell into stem cell memory, central memory, and effector memory subsets at different timepoints. T cells subsets Tscm (CD45RA+, CD45RO−, CCR7+, CD95+), Tcm (CD45RA−, CD45RO+, CCR7+, CD95+), and Tem (CD45RA−, CD45RO+, CCR7−, CD95+) were stained with an antibody cocktail and analyzed by flow cytometry. IL-2 withdrawal at (A) Day 4 (Solid square) and (C) Day 6 (Solid square) resulted in more advanced T cell differentiation recovering a higher percentage of T subset in effector memory phenotype, Day 5 (B, Solid square) IL-2 withdrawal was able to maintain T cell differentiation at the same level as the Control that was supplemented with IL-2 at 300 IU/ml continuously (Control, Solid circle), recovering a mixed pool of central memory and effector memory T cells.

Figure 46:
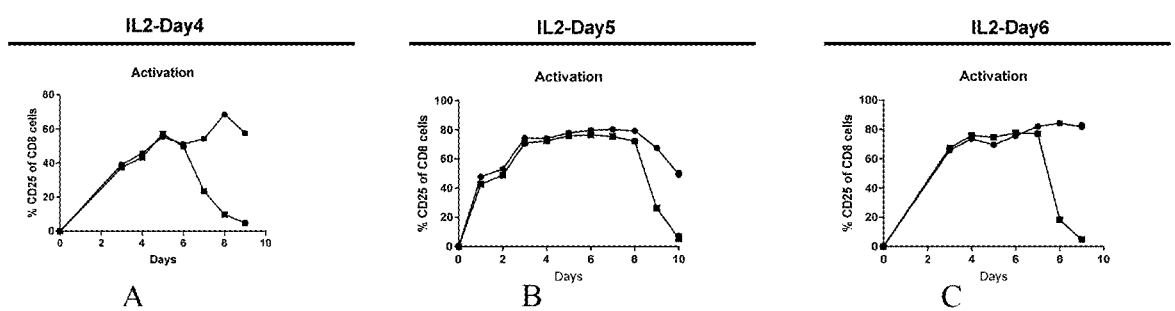
FIG. 46. Activation profile measured by CD25 surface expression. Control solid circle. Test sample solid square. (A) IL-2 withdrawal on Day 4 of the culture. (B) IL-2 withdrawal on Day 5 of the culture. (C) IL-2 withdrawal on Day 6 of the culture.

Withdrawal of IL-2 from the culture media resulted in T cells with reduced background activation or minimal activation signaling. Activation profiles were determined by CD25 surface expression. IL-2 withdrawal at Day 4 (A), Day 5 (B), and Day 6 (C) (Solid squares) potently reduced the expression of activation marker CD25 to a minimal level (<10%) upon harvest while the Control (Solid circle) that was continuously supplemented with IL-2 had significantly higher CD25 expression (50-80%) upon harvest, see FIG. 46.

Figure 47:
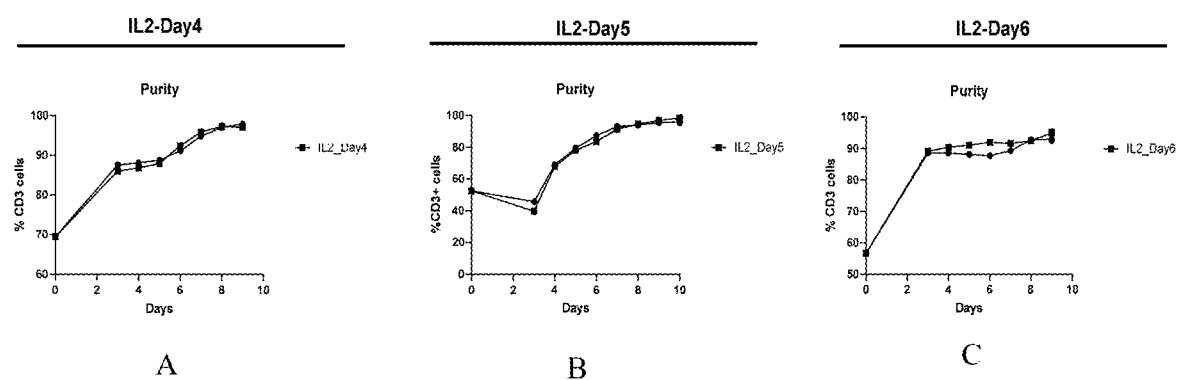
FIG. 47. T cell purity at different timepoints. Control solid circle. Test sample solid square. (A) IL-2 withdrawal on Day 4 of the culture. (B) IL-2 withdrawal on Day 5 of the culture. (C) IL-2 withdrawal on Day 6 of the culture.

FIG. 47 shows T cell purity at different timepoints. Cells were stained with an antibody cocktail targeting B cells (CD19), Monocytes (CD14), T cells (CD3+, CD56/16−), and NK cells (CD3−, CD56+) and analyzed by flow cytometry. Due to B cell absorption of CD3 antigen that leads to B cells expressing CD3 on their surface and being identified as T cells, the percentage of T cells was calculated by subtracting the percentage of CD19+B cells, CD14+ monocytes, and CD56/16+NK cells from 100%. IL-2 withdrawal at Day 4 (A), 5 (B), or 6 (C) (Solid squares) had no impact on CD3+ cell purity compared to the Control that was continuously supplemented with IL-2, (Control, Solid circle).

Figure 48:
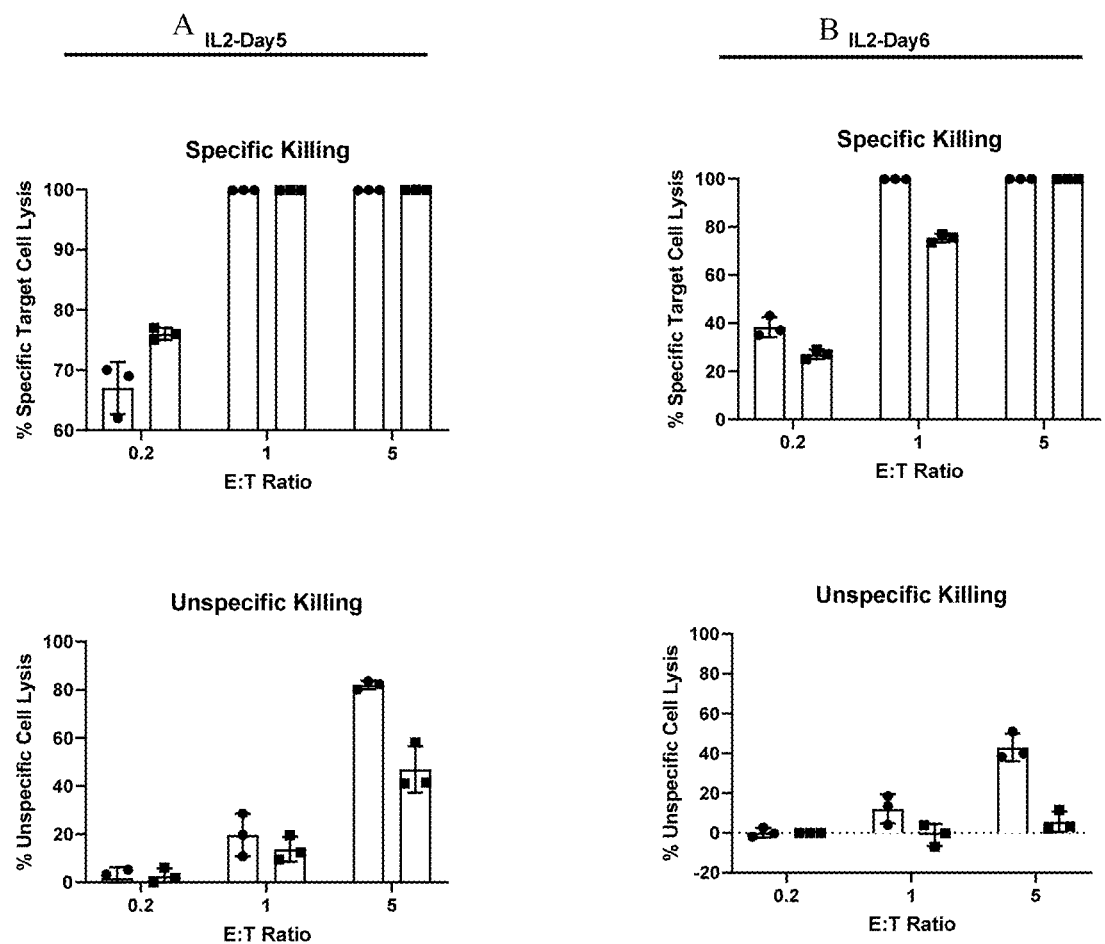
FIG. 48. Specific target cell lysis and unspecific cell lysis of T cells from different IL-2 conditions. Control solid circle. Test sample solid square. (A) IL-2 withdrawal on Day 5 of the culture. (B) IL-2 withdrawal on Day 6 of the culture.

Specific target cell lysis and unspecific cell lysis of T cells from the Day 5, Day 6, and Control test cultures is shown in FIG. 48. Harvested T cells were co-cultured with T2 cells pulsed with and without target peptide for 24 hours at E:T ratio at 1:5 (0.2), 1:1 (1), and 5:1 (5). T2 cells alone were also set up in culture as a background control. Percentage of specific killing of target cells was calculated by the percentage of cell death of peptide pulsed T2 cells normalized to no peptide pulsed T2 cells after 24 hours of co-culture. Unspecific cell lysis was calculated based on the percentage of cell death of T2 cells co-cultured with T cells for 24 hours normalized to T2 cell cultured alone. IL-2 withdrawal did not affect the percentage of specific target cells lysis but significantly reduced the percentage of unspecific killing (target irrelevant killing) of harvested T cells by ~40%, compared to the Control. (Control, Solid circle. Day 5 (A) and Day 6 (B) test samples, Solid squares).

This example demonstrated a reduction of target irrelevant activation of TCR-engineered T cell upon harvest by withdrawing IL-2 cytokine from culture media during expansion.

What is claimed is:

1. A method for producing genetically engineered autologous T cells that have reduced background activation and target irrelevant toxicity, the method comprising
   a) adding culture media comprising about 300 IU per ml IL-2 to a closed single use bioreactor bag;
   b) inoculating the bioreactor bag with apheresed donor cells and one or more soluble T cell activators, wherein at least one soluble T-cell activator is bound to at least one donor cell at the time of inoculation and the bioreactor bag is part of a rocking bioreactor platform;
   c) culturing the apheresed donor cells in the closed single use bioreactor bag containing culture media comprising about 300 IU per ml IL-2 and continuously rocking the bag at a rate of 2 rpm at a 2° angle;
   d) transducing the cells in the bioreactor bag with at least one soluble viral vector comprising a polynucleotide which encodes a protein of interest, the bioreactor bag containing culture media comprising about 300 IU per ml IL-2 and continuously rocking the bioreactor bag at a rate of 2 rpm at a 2° angle; and
   e) expanding the transduced cells in the bioreactor bag by feeding the transduced cells in the bioreactor bag with culture media comprising about 300 IU per ml IL-2 until Day 5 or Day 6 of the culture, after which the culture is fed with culture media comprising no IL-2, increasing the culture volume and the rocking rate as needed to maintain the culture until harvest,
   wherein harvested genetically engineered autologous T cells have reduced background activation and target irrelevant toxicity compared to engineered autologous T cells expressing the same protein of interest from the same apheresed donor cells produced by the same method in which IL-2 is maintained in the culture media at a concentration of about 300 IU per ml until harvest.

2. The method of claim 1, wherein the apheresed donor cells comprise cells from peripheral blood.

3. The method of claim 2, wherein the apheresed donor cells comprise nucleated and non-nucleated cells.

4. The method of claim 1, wherein the apheresed donor cells comprise leukocytes and erythrocytes.

5. The method of claim 4, wherein the apheresed donor cells also comprise granulocytes and/or platelets.

6. The method of claim 1, wherein the apheresis is leukapheresis.

7. The method of claim 1, wherein the apheresed donor cells are washed and resuspended in a culture media.

8. The method of claim 1, wherein at least one T cell activator is an anti CD3 antibody or binding fragments thereof.

9. The method of claim 1, wherein the T cell activator comprises an anti CD3 antibody and an anti CD28 antibody, or binding fragments thereof.

10. The method of claim 1, wherein the T cell activator comprises at least an anti CD3 antibody, an anti CD28 antibody, and an anti CD2 antibody, or binding fragments thereof.

11. The method of claim 1, wherein the T cell activator comprises at least an anti-human CD3 monospecific tetrameric antibody complex, an anti-human CD28 monospecific tetrameric antibody complex, and an anti-human CD2 monospecific tetrameric antibody complex.

12. The method of claim 1, wherein the concentration of at least one soluble T cell activator is at least 0.001 µg/ml to at least 10 µg/ml.

13. The method of claim 12, wherein the concentration of at least one soluble T cell activator is at least 0.1 µg/ml to at least 5 µg/ml.

14. The method of claim 1, wherein the number of nucleated cells within the apheresed donor cells is about 1.0E9 to about 1.4E9.

15. The method of claim 14, wherein the number of nucleated cells within the apheresed donor cells is about 1.2E9 to about 1.4E9.

16. The method according to claim 1, wherein the bioreactor bag contains at least 300 ml of culture media at inoculation.

17. The method according to claim 1, wherein the apheresed donor cells are cultured in the bioreactor bag for about 12-24 hours in part c).

18. The method of claim 1, wherein the viral vector is a retroviral vector.

19. The method of claim 1, wherein the viral vector is a lentiviral vector.

20. The method of claim 19, wherein the lentiviral vector is added at a MOI of 0.25-10.

21. The method of claim 19, wherein the lentiviral vector is added at a MOI of 1.

22. The method of claim 1, wherein the cells are transduced for about 20-24 hours.

23. The method of claim 1, following transduction half of the culture media is removed from the bioreactor bag and replaced with an equal volume of fresh culture media.

24. The method of claim 1, wherein during expansion the culture is fed by fed batch and/or perfusion.

25. The method of claim 24, wherein during expansion the culture is perfused at a rate is one half to double the bioreactor bag volume per day.

26. The method of claim 1, wherein during expansion the volume of the culture media in bioreactor is incrementally increased to 500 ml to maintain a cell density of at least 4E6 nucleated cells/ml.

27. The method of claim 1, wherein at harvest the volume of culture media in the single use closed bioreactor bag is 500 ml rocking at a rate of 4 rpm at a 4° angle to 6 rpm at a 6° angle.

28. The method according to claim 1, wherein the expansion begins at a culture volume of about 300 ml of culture media at a rocking rate of about 2 rpm at a 2° angle until the cells reach a predetermined cell density, the cell expansion is continued at a second culture volume of about 400 ml of culture media at a rocking rate of about 5 rpm at a 5° angle until the cells reach a predetermined cell density, and the cell expansion is continued at a third culture volume of about 500 ml at a rocking rate of about 6 rpm at a 6° angle until the cells reach a predetermined cell density after which the culture is maintained until harvest.

29. The method according to claim 28, wherein the predetermined cell density is 4E6 cells/ml.

30. The method of claim 1, wherein the cells are expanded for until they reach a target harvest cell density.

31. The method of claim 30, wherein the target harvest cell density is about 10 billion cells.

32. The method of claim 1, wherein the culture, transduction, and/or expansion steps are performed at 34-37° C.

33. The method of claim 1, wherein the protein of interest is a cell surface receptor.

34. The method of claim 33, wherein the cell surface receptor a T cell receptor, or chimeric antigen receptor.

35. The method of claim 33, wherein the cell surface receptor recognizes an antigenic target associated with a target cell.

36. The method of claim 35, wherein the target cell is a cancer cell.

37. The method of claim 1, wherein the genetically engineered autologous T cells are used to treat an indication in a patient in need.

* * * * *